US008653049B2

(12) United States Patent
Hipler et al.

(10) Patent No.: US 8,653,049 B2
(45) Date of Patent: Feb. 18, 2014

(54) NORMURAMYL GLYCOPEPTIDE COMPOUNDS

(75) Inventors: Karsten Hipler, Basel (CH); Andrew Miller, London (GB); Jaroslav Turanek, Brno (CZ); Miroslav Ledvina, Prague (CZ)

(73) Assignees: Imuthes Limited, London (GB); Institute of Organic Chemistry and Biochemistry AV CR, V.V.I., Prague (CZ); Vyzkumny USTAV Veterinarniho Lekarstvi, V.V.I., Brno (CZ)

( * ) Notice: Subject to any disclaimer, the term of this patent is extended or adjusted under 35 U.S.C. 154(b) by 424 days.

(21) Appl. No.: 12/922,663

(22) PCT Filed: Mar. 17, 2009

(86) PCT No.: PCT/GB2009/000703
§ 371 (c)(1), (2), (4) Date: Sep. 15, 2010

(87) PCT Pub. No.: WO2009/115782
PCT Pub. Date: Sep. 24, 2009

(65) Prior Publication Data
US 2011/0002983 A1  Jan. 6, 2011

(30) Foreign Application Priority Data
Mar. 17, 2008  (GB) .................................. 0804989.2

(51) Int. Cl.
A01N 43/04 (2006.01)
A61K 31/70 (2006.01)

(52) U.S. Cl.
USPC ............... 514/62; 514/23; 514/25; 514/53; 536/17.2; 536/18.5; 536/18.6; 536/18.7; 536/55.2

(58) Field of Classification Search
None
See application file for complete search history.

(56) References Cited

U.S. PATENT DOCUMENTS 4,369,178 A * 1/1983 Yamamura et al. .......... 514/20.9

FOREIGN PATENT DOCUMENTS

| WO | WO 91/11172 | 8/1991 |
| WO | WO 94/02518 | 2/1994 |
| WO | WO 98/55148 | 12/1998 |
| WO | WO 02/48170 | 6/2002 |
| WO | WO 03/047549 | 6/2003 |
| WO | WO 2006/016097 | 2/2006 |

OTHER PUBLICATIONS

Ledvina et al. Collect. Czech. Chem. Commun. (1998), vol. 63, pp. 577-589.*
Moroder et al. Biol. Chem. Hoppe-Seyler (1989), vol. 370, pp. 365-375.*
Anna Rohlenova, Synthesis of Muramyl Glycopeptides Modified in Both Peptide and Sugar Part of the Molecule, Diploma Thesis, Charles University, Faculty of Science, Department of Organic and Nuclear Chemistry 2000, Prague.
A. Rohlenova, Preparation of analogues of norAbu-MDP & norAbu-GMDP . . . , Abstracts of lectures & posters, Cukrblik 2000, Inst. of Microbiology AS CR, 2000 Prague.

* cited by examiner

*Primary Examiner* — Patrick Lewis
(74) *Attorney, Agent, or Firm* — Notaro, Michalos & Zaccaria P.C.

(57) ABSTRACT

The invention provides a compound (which can act as an adjuvant) of Formula I or Formula (II), wherein $R_1$ $R_4$ $R_5$ $R_6$ and $R_7$ are each independently selected from hydrogen, acetyl, hydrocarbyl, a lipid moiety and a lipid acyl moiety; $R_2$ is a hydroxyl, a hydrocarbyl, a lipid moiety, a lipid acyl moiety; or an amino hydrocarbyl group optionally substituted with a hydrocarbyl, a lipid moiety or a lipid acyl moiety; $R_3$ and $R_8$ are each independently selected from acetyl, a hydrocarbyl, a lipid moiety and a lipid acyl moiety; X is a peptide chain; The above normuramylglycopeptide compounds can be located in liposomes and micelles and can function as immunomodulators, along with a desired antigen (or DNA enclosing the antigen), in (e.g. DNA) vaccines.

30 Claims, 22 Drawing Sheets

NORMURAMYL GLYCOPEPTIDE COMPOUNDS

The present invention relates to novel normuramyl glycopeptide compounds, compositions comprising such compounds and their uses (e.g. as adjuvants and immunomodulators).

Adjuvants augment the effects of vaccines in protecting against fungal, viral or bacterial infections. They typically utilise or mimic specific sets of evolutionarily conserved molecules that act as signals of infection in the activation of the inate immune system, such as lipopolysaccharides (LPS), components of bacterial cell walls, and endocytosed nucleic acids, such as double-stranded RNA, single-stranded DNA, and unmethylated CpG motifs containing DNA.

Changes in the environment that result in a reduction in the immune capacity of an organism can cause serious medical problems. For example, an organism's immune capacity can be affected by changes such as an increase in the occurrence of pathogenic microorganisms resistant to antibiotics, an increase of infections damaging immunity (e.g. AIDS), and the use of immunosuppressive therapeutic procedures, such as radio- and chemotherapy of tumor diseases. To combat these problems, considerable attention is being given to the development of substances with immunostimulatory activity, such as adjuvant compounds that are non-specific stimulators of the immune response. When mixed with an antigen, adjuvant compounds may help to deposit or sequester the antigen and can cause a dramatic increase in the resultant antibody response.

One area of interest concerns synthetic compounds derived from consensus peptidoglycan fragments of the bacterial cell wall, namely from the minimal immunoadjuvant unit, "muramyldipeptide" (MDP), or the minimal repeat unit glucosaminylmuramyl dipeptide (GMDP), together or individually referred to as "muramyl glycopeptides".

anaemia; lymphomas (acute, non-Hodgkin, Hodgkin, and other); HIV infection; prevention of fungal and microbial infections in HIV positive patients, chemo- and radiation therapy or other situations in which patients are immunocompromised; Crohn's Disease; septic shock; radiation accidents.

Co-treatment with muramyl glycopeptides may allow higher effective doses and/or less side-effects in chemo and radiation therapy. Muramyl glycopeptides may also be used synergistically, or as a replacement, in conditions that have been implicated with a depletion in GM-CSF, such as lung disease, slow wound healing, hypercholesterimia, atherosclerosis, diabetes, obesity and metabolic syndrome. Muramyl glycopeptides predominatly act through internal receptors upstream to to cytokine and colony-stimulating factor release, which can link into negative feedback mechanisms (e.g. to prevent the presence of these cytokines and factors in high doses).

As an additional advantage, muramyl glycopeptides are cheaper to produce, as compared to cytokine and colony stimulating factor peptide drugs.

Many analogues of MDP have been synthesized and tested with the aim of increasing specific therapeutic effects and/or suppressing undesirable side-effects, such as pyrogenicity.

One analogue, MDP-Lys-L18 or Romurtide, comprises an MDP ring structure, but with the peptide chain prolonged with lysine and substituted with a stearoyl residue. Romurtide has been studied as a hemopoietic agent for restoration of leukemia in patients under radio- or chemotherapy. Romurtide increased the number of megakaryocytes and promoted the shift of megakaryocytes towards high ploidy class indicative of the promotion of proliferation and maturation of megakaryocytes. The serum levels of interleukin-6, stem cell factor, and erythropoietin elevated significantly before the enhanced response of megakaryocytes induced by romurtide was observed. Romurtide also enhanced production of colony-stimulating factors (CSFs), such as granulocyte-CSF, macrophage-CSF, and granulocyte-macrophage CSF, by

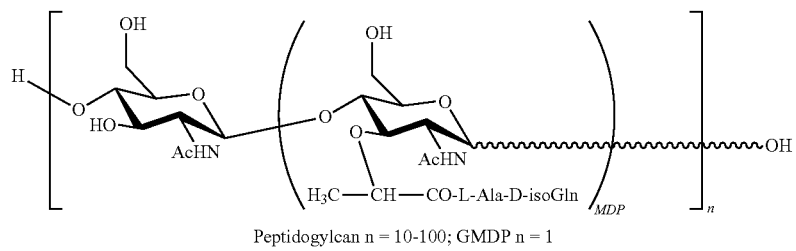

Peptidogylcan n = 10-100; GMDP n = 1

Muramyl glycopeptides may be used as adjuvants, but also to induce certain cytokines or substitute for, or complement, substances that are commonly used to induce certain cytokines or growth of certain cells, such as, in particular granulocyte-macrophage colony-stimulating factor, GM-CSF, and other progenitor cell activating factors. Unlike individual recombinant cytokines, or individual application of these colony-stimulating factors, the application of muramyl glycopeptides can trigger a physiologically balanced cascade of cytokines and the expression of the corresponding cell surface receptors. As a result, muramyl glycopeptides may have fewer side-effects than individual recombinant cytokine or progenitor cell colony-stimulating factor therapy. This can be of importance for indications in which the balance between efficacy and side-effects is very delicate, such as in aplastic monkey mononuclear cells (Vaccine. 1997 March; 15(4): 405-13). In addition, Romurtide has been shown to provide an enhancement of nonspecific resistance to microbial and viral infections and to tumor growth in immunocompetent as well as in immunocompromised animal models. Owing to its marked adjuvant activity, Romurtide has been used for the construction of experimental vaccines capable of eliciting both humoral and cellular immune responses. Romurtide is less pyrogenic than MDP. In a phase I clinical study, the only noticeable subjective or objective symptoms that were detected was a slight increase in body temperature and a transient local reaction at the injection site. Although Romurtide induces a number of cytokines, it causes less serious side effects as compared to recombinant cytokines when used in isolation or combination.

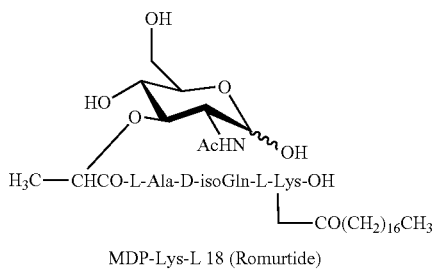

MDP-Lys-L 18 (Romurtide)

Glucosaminyl-murannyldipeptide (GMDP), the basic disaccharide-dipeptide repeat unit of peptidoglycan, can have an even higher immunoadjuvant activity than MDP and can be less pyrogenic. It also has been found to provide an enhancement of nonspecific resistance to infections and anti-tumor effects.

A lipophilic analogue of GMDP called disaccharidetripeptide-glyceroldipalmitate (DTP-GDP) has also been developed. DTP-GDP is more effective as an adjuvant and macrophage activator inducing anti-tumor activities in vivo and in vitro than MDP. However, DTP-GDP was found to be pyrogenic in rabbits and caused fever, chills, nausea and hypertension as its major systemic side-effects in a phase I clinical trial.

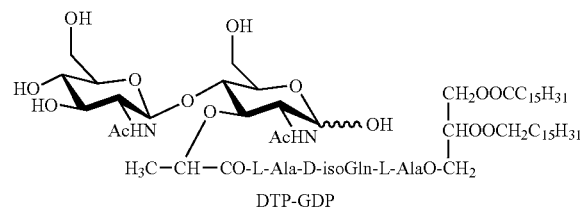

DTP-GDP

Analogues of MDP and GMDP have also been reported that contain modifications both in the saccharide as well as in the peptide part of the molecule. Specifically, the muramic acid and L-alanine components of MDP have been replaced with normuramic acid and L-2-aminobutyric acid, respectively, to produce norAbu-MDP. Similarly, making analogous structural changes in GM DP has provided an analogue, norAbu-GMDP.

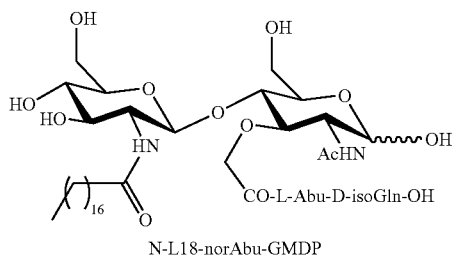

N-L18-norAbu-GMDP

The compound N-L18-norAbu-GMDP has been obtained by introducing a bulky stearoyl residue onto the $NH_2$ group of the glucosamine subunit of norAbu-GMDP.

The introduction of a bulky acyl residue onto the primary OH group of norAbu-MDP[23,24] or norAbu-GMDP, for example in B30-norAbu-MDP or L18-norAbu-GMDP GMDP, has also been taught.

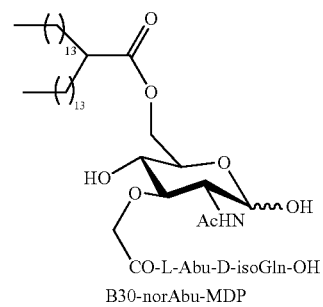

B30-norAbu-MDP

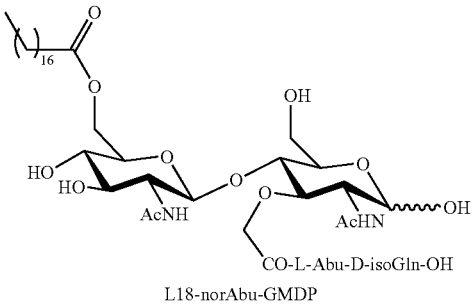

L18-norAbu-GMDP

Various analogues of norAbu-MDP and norAbu-GMDP have been examined as regards their pyrogenicity, their immunostimulatory activity, and their ability to restore the hemopoietic and immune systems in an artificially immunocompromised host.

Despite the improvements that some of these compounds have shown over MDP and GMDP, there is a continuing need for compounds with further reduced side effects and increased therapeutic activity.

INVENTION

The present invention seeks to alleviate the problems in the prior art.

In one aspect the present invention thus provides a compound of Formula I or Formula II Formula I

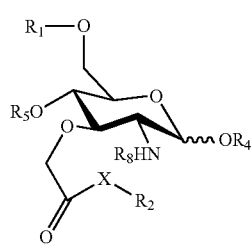

Formula II

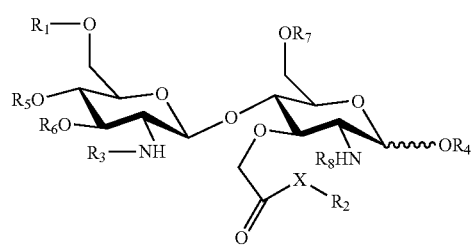

wherein $R_1$, $R_4$, $R_5$, $R_6$ and $R_7$ are each independently selected from hydrogen, acetyl, hydrocarbyl (preferably acyl or alkyl), a lipid moiety and a lipid acyl moiety;

$R_2$ is a hydroxyl, a hydrocarbyl (preferably acyl or alkyl), a lipid moiety, a lipid acyl moiety; or an amino hydrocarbyl group optionally substituted with a hydrocarbyl (preferably acyl or alkyl), a lipid moiety or a lipid acyl moiety;

$R_3$ and $R_8$ are each independently selected from acetyl, a hydrocarbyl (preferably acyl or alkyl), a lipid moiety and a lipid acyl moiety;

X is a peptide chain;

wherein at least one hydrocarbyl (preferably acyl or alkyl), lipid moiety or lipid acyl moiety is present.

Preferably, the compound is other than one or more of the following:

(i) a compound of formula I where $R_1$ is stearoyl, $R_2$ is —OH, $R_4$ and $R_5$ are hydrogen, $R_8$ is acetyl; and X is -L-Abu-D-isoGln-;

(ii) a compound of formula II where $R_1$ is stearoyl, $R_2$ is —OH; $R_3$ and $R_8$ are acetyl, $R_4$, $R_5$, $R_6$ and $R_7$ are hydrogen; and X is -L-Abu-D-isoGln-;

(iii) a compound of formula I where $R_1$ is 2-tetradecylhexadecanoyl, $R_2$ is —OH, $R_4$ and $R_5$ are hydrogen, $R_8$ is acetyl; and X is -L-Abu-D-isoGln-;

(iv) a compound of formula II where $R_1$ is 2-tetradecylhexadecanoyl, $R_2$ is —OH; $R_3$ and $R_8$ are acetyl, $R_4$, $R_5$, $R_6$ and $R_7$ are hydrogen; and X is -L-Abu-D-isoGln-;

(v) a compound of formula II where $R_1$ is hydrogen, $R_2$ is —OH; $R_3$ is stearoyl, $R_4$, $R_5$, $R_6$ and $R_7$ are hydrogen, $R_8$ is acetyl; and X is -L-Abu-D-isoGln-;

(vi) a compound of formula I where $R_1$ is palmitoyl, stearoyl, 2-tetradecylhexadecanoyl or adamantyl-carbonyl, $R_2$ is —OH, $R_4$ and $R_5$ are hydrogen, $R_8$ is acetyl; and X is -L-Abu-D-isoGln-;

(viii) a compound of formula I where $R_1$ is a group of formula $R_{10}$—(CO)— wherein $R_{10}$ is a C10 to C30 hydrocarbon group, $R_2$ is —OH, $R_4$ and $R_5$ are hydrogen, $R_8$ is acetyl; and X is -L-Abu-D-isoGln-;

(ix) a compound of formula I where $R_1$ is a linear, branched, cyclic or polycyclic lipophilic acyl radical having 4 to 70 carbon atoms, such as palm itoyl, stearoyl, adamantyl-carbonyl, 2-tetradecylhexadecanoyl or a linear, branched, cyclic or polycyclic lipophilic acyl radical having 23 to 70 carbon atoms, $R_2$ is —OH, $R_4$ and $R_5$ are hydrogen, $R_8$ is acetyl; and X is -L-Abu-D-isoGln-;

(x) a compound of formula I where $R_4$ is benzyl;

(xi) a compound of formula I where $R_2$ is an unmodified peptide or peptide chain, such as D-isoGln, H-Thr-Lys-Pro-Arg-OH, H-Thr-Lys-Pro-Arg($NO_2$)—OH or Arg-Pro-Lys-ThrOMe.

(xii) a compound of formula I where $R_2$ is a nitrogen or nitrogen and oxygen-containing tricyclic hydrocabon group;

(xiii) a compound of formula I where $R_2$ is an acridine or acridone group (e.g. a tricyclic fused ring system, each ring being 6 carbon atoms) or derivative thereof; and/or (xiv) a compound of formula I where $R_2$ is aminoalkylamino-1-nitroacridine wherein alkyl is C2, C3, C4 or C5 alkyl or $(CH_2)_2NH(CH_2)_2$ or aminoalkyl-4-nitro-acridinone wherein alkyl is C2, C3, C4 or C5 alkyl.

In one embodiment, the compound is other than:

(i) a compound of formula I where $R_1$ is stearoyl, $R_2$ is —OH, $R_4$ and $R_5$ are hydrogen, $R_8$ is acetyl; and X is -L-Abu-D-isoGln-;

(ii) a compound of formula II where $R_1$ is stearoyl, $R_2$ is —OH; $R_3$ and $R_8$ are acetyl, $R_4$, $R_5$, $R_6$ and $R_7$ are hydrogen; and X is -L-Abu-D-isoGln-;

(iii) a compound of formula I where $R_1$ is 2-tetradecylhexadecanoyl, $R_2$ is —OH, $R_4$ and $R_5$ are hydrogen, $R_8$ is acetyl; and X is -L-Abu-D-isoGln-;

(iv) a compound of formula II where $R_1$ is 2-tetradecylhexadecanoyl, $R_2$ is —OH; $R_3$ and $R_8$ are acetyl, $R_4$, $R_5$, $R_6$ and $R_7$ are hydrogen; and X is -L-Abu-D-isoGln-; and (v) a compound of formula II where $R_1$ is hydrogen, $R_2$ is —OH; $R_3$ is stearoyl, $R_4$, $R_5$, $R_6$ and $R_7$ are hydrogen, $R_8$ is acetyl; and X is -L-Abu-D-isoGln-.

In one preferred aspect, the present invention provides a compound of Formula Ia or Formula IIa wherein

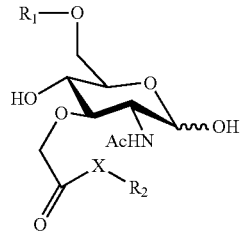

Formula Ia

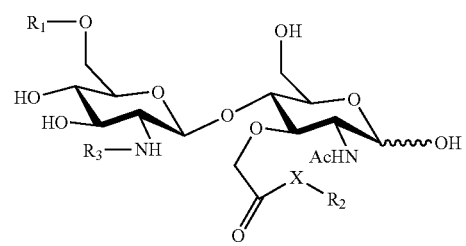

Formula IIa $R_1$ is hydrogen, acetyl, acyl or alkyl;

$R_2$ is a hydroxyl, acyl, alkyl; or an amino hydrocarbyl group optionally substituted with an acyl or alkyl;

$R_3$ is acetyl, acyl or alkyl; and/or

X is a peptide chain;

wherein at least one acyl or alkyl is present.

Preferably, the compound is other than one or more of (i) to (xiv) as set out above.

In one embodiment, the compound is other than:

a compound of formula Ia where $R_1$ is stearoyl, $R_2$ is —OH; and X is -L-Abu-D-isoGln-;

(ii) a compound of formula IIa where $R_1$ is stearoyl, $R_2$ is —OH; $R_3$ is acetyl; and X is -L-Abu-D-isoGln-;

(iii) a compound of formula Ia where $R_1$ is 2-tetradecylhexadecanoyl, $R_2$ is —OH; and X is -L-Abu-D-isoGln-;

(iv) a compound of formula IIa where $R_1$ is 2-tetradecylhexadecanoyl, $R_2$ is —OH; $R_3$ is acetyl; and X is -L-Abu-D-isoGln-; and (v) a compound of formula IIa where $R_1$ is hydrogen, $R_2$ is —OH; $R_3$ is stearoyl; and X is -L-Abu-D-isoGln-.

In Formula I and Formula II, preferably, $R_1$ is hydrogen, acetyl or acyl;

$R_2$ is a hydroxyl, acyl; or an amino hydrocarbyl group substituted with acyl;

$R_3$ is acetyl or acyl;

$R_4$, $R_5$, $R_6$ and $R_7$ are each hydrogen; and/or $R_8$ is acetyl.

At least one hydrocarbyl (preferably acyl or alkyl), lipid moiety or lipid acyl moiety is present. Thus, for example, one, two, three or more hydrocarbyls (preferably acyl or alkyl), lipid moieties or lipid acyl moieties may be present. In one embodiment, the compound contains one hydrocarbyl (preferably acyl or alkyl), lipid moiety or lipid acyl moiety.

In one embodiment, the present invention provides a compound of Formula I wherein:
$R_1$ is selected from hydrocarbyl (preferably acyl or alkyl), a lipid moiety and a lipid acyl moiety;
$R_2$ is hydroxyl;
$R_4$ and $R_5$ are each hydrogen;
$R_8$ is acetyl; and
X is a peptide chain.

In one embodiment, the present invention provides a compound of Formula I wherein:
$R_1$ is hydrogen;
$R_2$ is a hydrocarbyl (preferably acyl or alkyl), a lipid moiety, a lipid acyl moiety; or an amino hydrocarbyl group optionally substituted with a hydrocarbyl (preferably acyl or alkyl), a lipid moiety or a lipid acyl moiety;
$R_4$ and $R_5$ are each hydrogen;
$R_8$ is acetyl; and
X is a peptide chain.

In one embodiment, the present invention provides a compound of Formula II wherein:
$R_1$ is selected from hydrocarbyl (preferably acyl or alkyl), a lipid moiety and a lipid acyl moiety;
$R_2$ is hydroxyl;
$R_3$ is acetyl;
$R_4$, $R_5$, $R_6$ and $R_7$ are each hydrogen;
$R_8$ is acetyl; and
X is a peptide chain.

In one embodiment, the present invention provides a compound of Formula II wherein:
$R_1$ is hydrogen;
$R_2$ is a hydrocarbyl (preferably acyl or alkyl), a lipid moiety, a lipid acyl moiety; or an amino hydrocarbyl group optionally substituted with a hydrocarbyl (preferably acyl or alkyl), a lipid moiety or a lipid acyl moiety;
$R_3$ is acetyl;
$R_4$, $R_5$, $R_6$ and $R_7$ are each hydrogen;
$R_8$ is acetyl; and
X is a peptide chain.

In one embodiment, the present invention provides a compound of Formula II wherein:
$R_1$ is hydrogen;
$R_2$ is hydroxyl;
$R_3$ is selected from hydrocarbyl (preferably acyl or alkyl), a lipid moiety and a lipid acyl moiety;
$R_4$, $R_5$, $R_6$ and $R_7$ are each hydrogen;
$R_8$ is acetyl; and
X is a peptide chain.
$R_2$ In one embodiment, $R_2$ is an amino group substituted with one or more alkoxycarbonyl groups or with one or more alkyl groups optionally bearing a carboxyl, alkoxycarbonyl, hydroxyl or mercapto functional group.

In one preferred embodiment, $R_2$ is a substituent of formula V

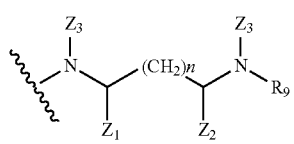

Formula V wherein
$Z_1$ and $Z_2$ are each independently hydrogen, a carboxyl group optionally substituted with an alkyl group, or a carbamoyl group optionally substituted with one or more alkyl substituents at the nitrogen atom;
$Z_3$ is hydrogen or a hydrocarbyl group;
$R_9$ is hydrocarbyl, preferably acyl; and
n is an integer from 1 to 10.

Preferably, $Z_1$ is alkoxycarbonyl group or free or mono- or disubstituted carbamoyl group at the nitrogen atom, or carboxyl-, alkoxycarbonyl- or aminocarbonyl-lower alkylaminocarbonyl group.

Preferably, $Z_2$ is alkoxycarbonyl group or free or mono- or disubstituted carbamoyl group at the nitrogen atom, or carboxyl-, alkoxycarbonyl- or aminocarbonyl-lower alkylaminocarbonyl group.

Preferably, where $Z_3$ is a hydrocarbyl group, that group is a lower (C1 to C10) alkyl group.

Preferably $Z_3$ is hydrogen or a C1 to C7 alkyl group.
More preferably $Z_1$ is —$CO_2H$.
Preferably $Z_2$ is hydrogen.
Preferably $Z_3$ is hydrogen.
Preferably n is an integer from 1 to 9; 1 to 8: 1 to 7; 1 to 6; 1 to 5; 1 to 4; 1 to 3; and/or 1 to 2.
Preferably n is 3.
Thus, in one embodiment, $Z_1$ is —$CO_2H$, n is 3, $Z_2$ is hydrogen and/or $Z_3$ is hydrogen.

Hydrocarbyl R Groups/Substituents

In one embodiment, the hydrocarbyl is a C10 to (C40 or C50 or) C80 saturated or unsaturated and linear or branched hydrocarbon. Preferably, the hydrocarbyl is an alkyl, preferably a C10 to (C40 or C50 or) C80 saturated or unsaturated and linear or branched alkyl.

In another embodiment, the hydrocarbyl is, or comprises, an acyl.
Preferably the acyl is selected from:
a) a group of formula $R_{10}$—C(O)— wherein $R_{10}$ is a C10 to (C20, C30 or C40 or) C80 saturated or unsaturated and linear, branched, cyclic or polycylic hydrocarbyl group; and
b) a mycolic acid compound of formula VI

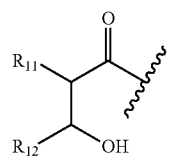

Formula VI wherein
$R_{11}$ is a C10 to C30 hydrocarbon group; and
$R_{12}$ is a C20 to C70 hydrocarbon group optionally bearing one or more carbon-carbon double bonds, cyclopropane rings, keto, hydroxyl, alkoxy, acyloxy, and carboxylic ester groups.

Preferably $R_{10}$ is a C10 to C20 or C30 hydrocarbon group. Thus, for example, $R_{10}$ may be C10 to C30 hydrocarbon group.

In one embodiment, $R_{10}$ is selected from:
a) a C10-C80 saturated or unsaturated and linear or branched alkyl group;
b) a saturated or unsaturated cycloalkyl- or polycycloalkyl-group;
c) a saturated or unsaturated cycloalkyl alkyl- or polycycloalkyl alkyl-group;
d) a saturated or unsaturated alkyl-, cycloalkyl-, polycycloalkyl-, cycloalkylalkyl- or polycycloalkylalkyl- oxycarbonylalkylene-group; and e) a saturated or unsaturated alkyl-, cycloalkyl-, polycycloalkyl-, cycloalkylalkyl- or polycycloalkylalkyl- oxyalkylene-group.

In one embodiment, the acyl is derived from a long-chain aliphatic carboxylic acid, cycloalkyl carboxylic acid, polycycloalkyl carboxylic acid (for example adamantyl carboxylic acid or etienic acid), cycloalkyl alkyl carboxylic acid (for example retinoic acid), poly-cycloalkyl alkyl carboxylic acid (for example cholic acid), or aryl or arylalkyl carboxylic acids or optionally substituted carboxylic, especially by alkanol mono-esterified dicarboxylic acid or etherified hydroxylcarboxylic acid with alcohols specified below (for example, cholesteryl, dihydrocholesteryl, or retinol hemisuccinate, cholesterol or retinol etherified γ-hydroxybutyric acid, natural or synthetic mycolic acids), or from vitamin E or its analogues, including tocopherol or tocotrienol derivatives.

Adamantane residue, for example, may help improve penetration into cell membranes. As another example, vitamin E or its analogues (including tocopherol or tocotrienol derivatives and redox-silent analogues of tocotrienol, such as 6-O-carboxypropyl-alpha-tocotrienol (T3E)) have the advantage of being cheap, biocompatible (being a natural component of cells) and may help boost the immune response.

More preferably the acyl is selected from a C10-C80 aliphatic carboxyl substituent, adamantyl carboxyl, cholic acid, stearoyl (L18), tetradecylhexadecanoyl (B30), cholesteryl or dihydrocholesteryl hemisuccinyl, retinol hemisuccinate, cholesterol etherified γ-hydroxybutyric acid, retinol etherified γ-hydroxybutyric acid and tocopherol or tocotrienol derivative.

In one embodiment, preferably the acyl is a C10-C30 aliphatic carboxyl group, such as stearoyl (L18).

In another preferred embodiment, the acyl is an α-branched fatty acid derivative of formula VII:

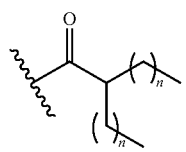

VII and n is an integer from 10 to 40. Preferably n is an integer from 10 to 13, 15 or 20, such as from 12-14.

In one preferred embodiment, the present invention relates to a compound of Formula I or Formula II, wherein at least one acyl is present and is of formula VII, wherein n is 13 (B30). In one embodiment, $R_3$ is of formula VII wherein n is 13.

In one embodiment, the acyl is a ω-adamantylalcanoyl acid derivative of formula VIII

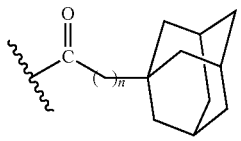

VIII and n=1, 2, 3, 4 or 5.

In one embodiment, the acyl is a retinoic acid derivative of formula IX:

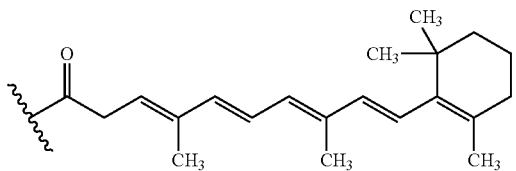

IX

In one embodiment, the acyl is a tocopherol or tocotrienol derivative of the following formulae:

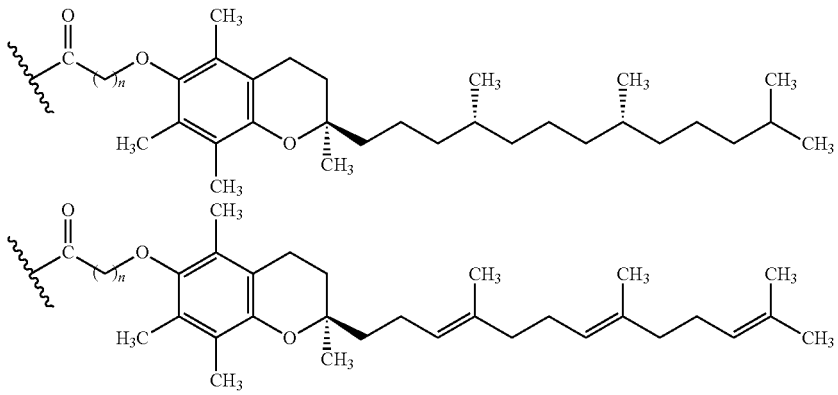

wherein n=1, 2, 3, 4 or 5.

In one embodiment, the acyl is a cholesteryl (or dihydro cholesteryl) hemisuccinate of formula X:

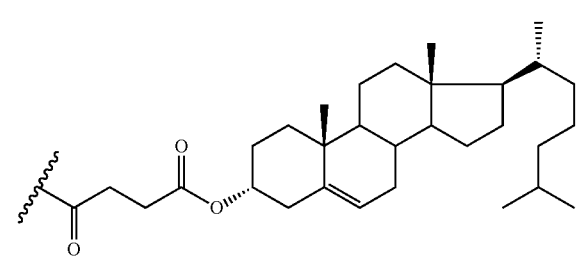

X

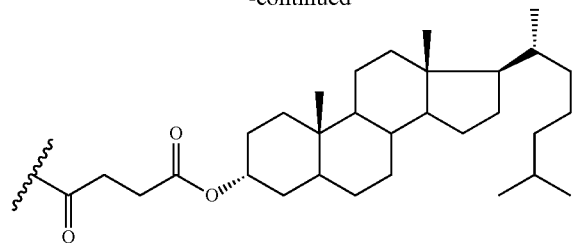

In one embodiment, the acyl is a cholesteryl-hydroxy acid derivative of the following formula:

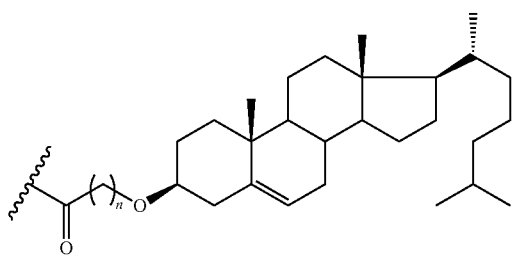

wherein n=1, 2, 3, 4 or 5, such as a cholesteryl-glycolyl acid derivative of formula XI:

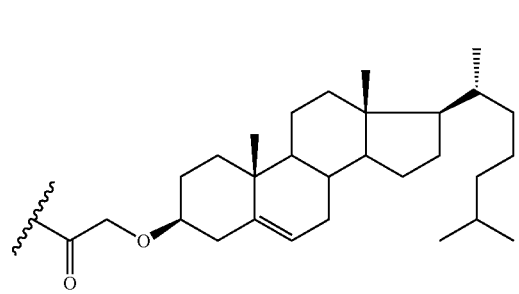

XI

Lipid and Lipid Acyl R Groups/Substituents

As used herein, "lipid" refers to fatty acids and their derivatives, and substances related biosynthetically or functionally to these compounds. The lipid moiety may thus be a fatty acid (e.g., stearic acid, palmitic acid), condensed with a polar head group molecule, for example glycerol or phosphoglycerol. The lipid moiety may also be, for example, a sterol lipid such as cholesterol.

The lipid moiety may be derived from, for example, a neutral lipid, sterol lipid or phospholipid.

Examples of neutral lipids include: lecithins; phosphatidylethanolamines, such as DOPE (dioleoyl phosphatidylethanolamine), POPE (palmitoyloleoylphosphatidylethanolamine) and DSPE (distearoylphosphatidylethanolamine); phosphatidylcholine; phosphatidylcholines, such as DOPC (dioleoyl phosphatidylcholine), DPPC (dipalmitoylphosphatidylcholine) POPC (palmitoyloleoyl phosphatidylcholine) and DSPC (distearoylphosphatidylcholine); phosphatidylglycerol; phospha-tidylglycerols, such as DOPG (dioleoylphosphatidylglycerol), DPPG (dipalmitoylphosphatidylglycerol), and DSPG (distearoylphosphatidylglycerol); phosphatidylserines, such as dioleoyl- or dipalmitoylphosphatidylserine; diphosphatidylglycerols; fatty acid esters; glycerol esters; diacylglycerols, sphingolipids; cardiolipin; cephalin, cerebrosides; glycerol based lipids (e.g. cardiolipid); and ceramides.

Examples of phospholipids include phosphatidylcholine, phosphatidylethanolamine, phosphatidylglycerol, phosphatidylserine, phosphatidic acid and phosphatidylinositol.

Examples of sterol lipids include cholesterol.

The lipid acyl moiety can be represented by the formula L-C(O), wherein L is a lipid moiety. The lipid acyl moiety is linked to the rest of the compound via the acyl group.

Peptide Chain X

In one preferred embodiment, X is a mono-, di- or polypeptide (of up to 5, 10, 20 or 30 peptides) chain or moiety, such as a dipeptide.

In one preferred embodiment, X comprises one or more amino acid units selected independently from L- or D-alanine (Ala), and L-2-aminobutyric acid (Abu), L- or D-serine (Ser), glycine (Gly), L- or D-leucine (Leu) and L- or D-Isoleucine (Ile).

In one preferred embodiment, X comprises one or more amino acid units selected independently from L- or D-glutamine (Gln), L- or D-asparagine (Asn), L- or D-glutamic L- or D-acid (Glu) and L- or D-iso-glutamine (isoGln).

Preferably, X is a dipeptide and comprises one amino acid unit selected independently from alanine (Ala), preferably L-alanine, L-2-aminobutyric acid (Abu), L- or D-serine (Ser), glycine (Gly), L- or D-leucine (Leu) and L- or D-Isoleucine (Ile) and one amino acid unit selected independently from L- or D-glutamine (Gln), L- or D-asparagine (Asn), L- or D-glutamic acid (Glu) and L- or D-iso-glutamine (isoGln).

In another preferred embodiment, X comprises one or more amino acid units selected independently from alanine (Ala, preferably L-alanine) and, L-2-aminobutyric acid (Abu).

Preferably, X is a dipeptide and comprises one amino acid unit selected independently from alanine (Ala, preferably L-alanine) and L-2-aminobutyric acid (Abu), and one amino acid unit selected independently from L- or D-glutamine (Gln), L- or D-asparagine (Asn), L- or D-glutamic acid (Glu) and L- or D-iso-glutamine (isoGln).

Preferably, X is L-Abu-D-isoGln.

In one embodiment, the peptide chain X comprises a sub-unit of the general formula III and/or IV

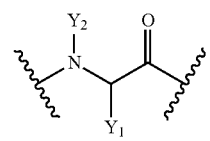

III

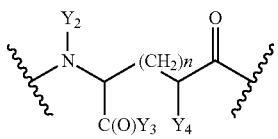

IV wherein $Y_1$ is hydrogen or a hydrocarbyl group, $Y_2$ is hydrogen or a hydrocarbyl group, $Y_3$ is a hydroxyl group optionally substituted with an alkyl group, or an amino group optionally substituted with one or more hydrocarbyl group, $Y_4$ is hydrogen, or an amino group optionally substituted with one or more hydrocarbyl groups, and n is an integer from 1 to 10.

For example, where $Y_1$ is a hydrocarbyl group, that group may be a lower alkyl, free or functionally modified hydroxy-lower alkyl, free or functionally modified amino-lower alkyl, free or functionally modified mercapto-lower alkyl, cycloalkyl, cycloalkyl-lower alkyl, optionally substituted aryl or arylalkyl, nitrogen-containing heterocyclyl or nitrogen-containing heterocyclyl-lower alkyl.

For example, where $Y_2$ is a hydrocarbyl group, that group may be a lower alkyl group.

For example, $Y_3$ may be a free or alkylated hydroxyl group, free or mono- or di-alkylated amino group, lower alkylamino, or carboxyl-, alkoxycarbonyl- or aminocarbonyl-lower alkylamino group.

For example, $Y_4$ may be a free or functionally modified amino group such as mono- or dialkylamino group or acylamino group (for example methylamino, ethylamino, dimethylamino, diethylamino or alkanoylamino group).

Preferably the subunits comprise L- and/or D-amino acid units.

$Y_1$ may be selected from
a) H;
b) a C1 to C7 alkyl group optionally substituted with a hydroxyl, amino or mercapto functional group;
c) a C1 to C7 alkyl group bearing a saturated or unsaturated 5 or 6 membered nitrogen-containing heterocyclic ring, with the ring being optionally substituted with one or more C1 to C7 alkyl groups;
d) a C1 to C7 alkyl group bearing a condensed heterocyclic system containing an unsaturated 5 or 6 membered nitrogen-containing heterocyclic ring, with the system being optionally substituted with one or more C1 to C7 alkyl groups; and
e) a saturated or unsaturated cycloalkyl-, optionally substituted with a C1 to C7 alkyl group; or a saturated or unsaturated polycycloalkyl-, optionally substituted with a C1 to C7 alkyl group.

For example, $Y_1$ may be an aryl group optionally substituted with one or more C1 to C7 alkyl groups.

For example, $Y_1$ may be a saturated or unsaturated 5 or 6 membered nitrogen-containing heterocyclic ring optionally substituted with one or more C1-C7 alkyl groups; or a condensed heterocyclic system containing an unsaturated 5 or 6 membered nitrogen-containing heterocyclic ring, with the system being optionally substituted with one or more C1 to C7 alkyl groups.

$Y_2$ may be hydrogen or C1 to C7 alkyl group.

$Y_3$ may be an amino group substituted with one or more alkoxycarbonyl groups or with one or more alkyl groups optionally bearing a carboxyl, alkoxycarbonyl, hydroxyl or mercapto functional group.

$Y_4$ may be selected from a $Y_4$ is selected from a methylamino, ethylamino, dimethylamino, diethylamino or an alkanoylamino substituent.

n may be, for example, an integer from 1 to 9; 1 to 8; 1 to 7; 1 to 6; 1 to 5; 1 to 4; 1 to 3; 1 to 2.

Compounds

Preferably the compound of the present invention is any one of:

(i) a compound of formula I, in which $R_1$ is cholesteryl (or dihydrocholesteryl) hemisuccinyl, $R_2$ is hydroxyl, $R_4$ and $R_5$ are hydrogen, $R_8$ is acetyl and X is L-Abu-D-isoGln;

(ii) a compound of formula I, in which $R_1$ is hydrogen, $R_4$ and $R_5$ are hydrogen, $R_8$ is acetyl, X is L-Abu-D-isoGln and $R_2$ is

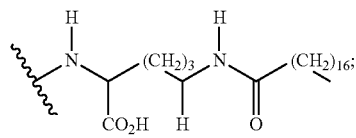

(iii) a compound of formula I, in which $R_1$ is hydrogen, $R_4$ and $R_5$ are hydrogen, $R_8$ is acetyl, X is L-Abu-D-isoGln and $R_2$ is

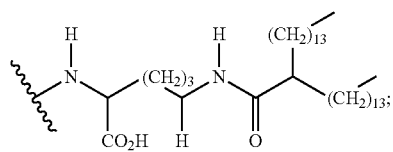

(iv) a compound of formula II, in which $R_1$ is hydrogen, $R_4$, $R_5$, $R_6$ and $R_7$ are each hydrogen, X is L-Abu-D-isoGln, $R_3$ and $R_8$ are acetyl and $R_2$ is

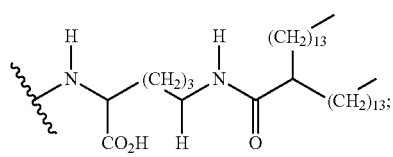

(v) a compound of formula II, in which $R_1$ is hydrogen, $R_4$, $R_5$, $R_6$ and $R_7$ are each hydrogen, X is L-Abu-D-isoGln, $R_3$ and $R_8$ are acetyl and $R_2$ is

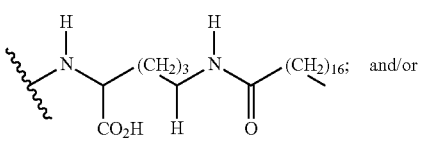

and/or (vi) a compound of formula II, in which $R_1$ is hydrogen, $R_2$ is hydroxyl, $R_3$ is 2-tetradecylhexadecanoyl, $R_4$, $R_5$, $R_6$ and $R_7$ are each hydrogen, $R_8$ is acetyl and X is L-Abu-D-isoGln.

In another embodiment, the compound of the present invention is a compound of formula I, in which $R_1$ is an acyl group. Preferably, such a compound is selected from:

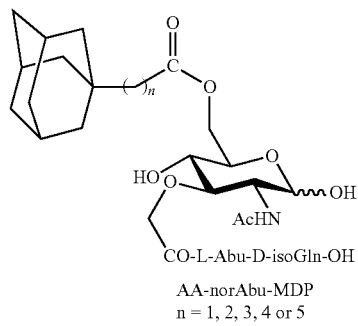

AA-norAbu-MDP
n = 1, 2, 3, 4 or 5

-continued

ChS-norAbu-MDP (or the dihydro equivalent DHChS-norAbu-MDP)

ChHA-norAbu-MDP
and n = 1, 2, 3, 4, or 5, for example:

ChG-norAbu-MDP

RA-norAbu-MDP

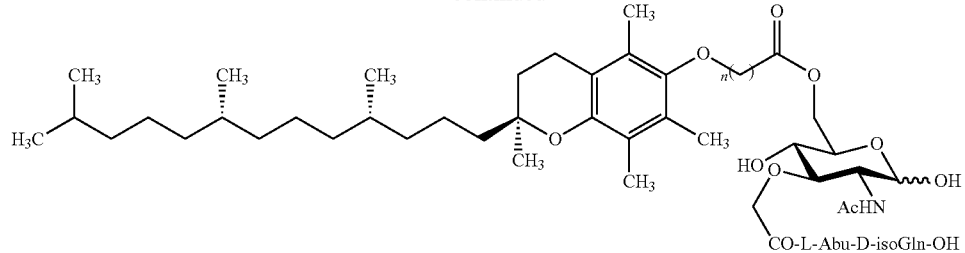
THA-norAbu-MDP
and n = 1, 2, 3, 4 or 5
In another embodiment, the compound of the present invention is a compound of formula II, in which $R_3$ is an acyl group. Preferably, such a compound is selected from:
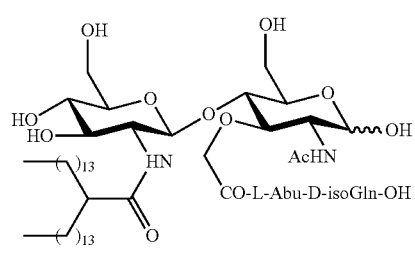
N-B30-norAbu-GMDP
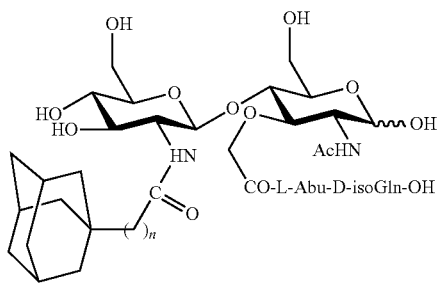
N-AA-norAbu-GMDP
and n = 1, 2, 3, 4 or 5
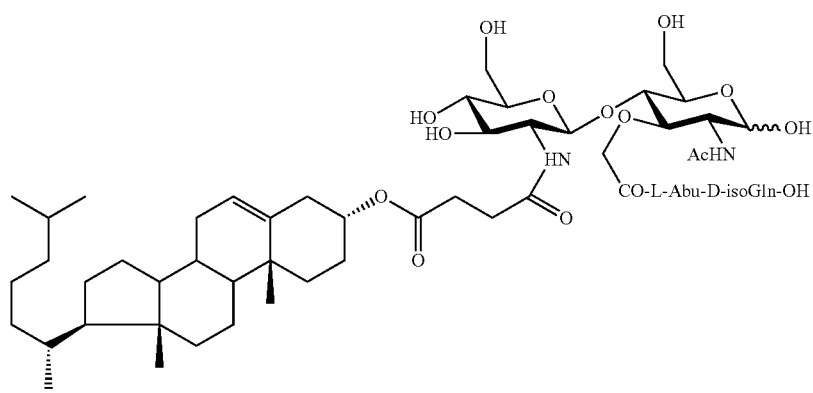
N-ChS-norAbu-GMDP (or the dihydro equivalent N-DHChS-norAbu-GMDP)
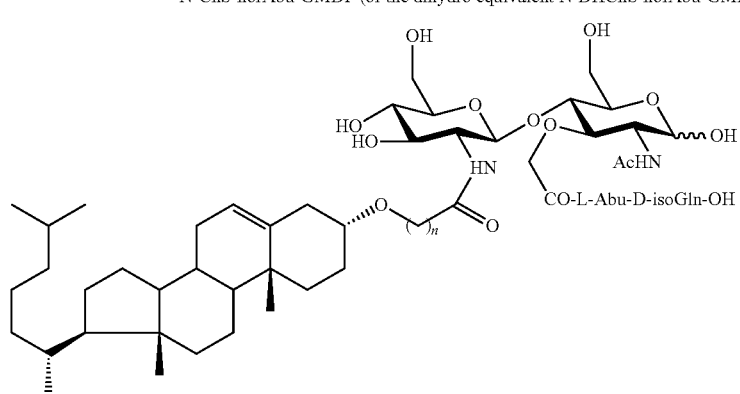
N-ChHA-norAbu-GMDP
and n = 1, 2, 3, 4 or 5, for example:

-continued
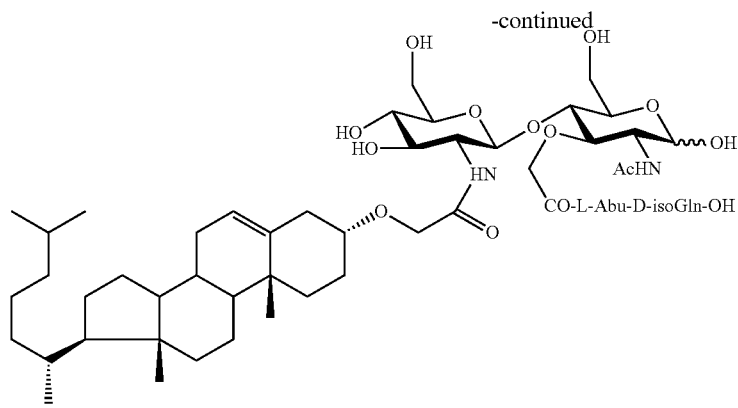
N-ChG-norAbu-GMDP
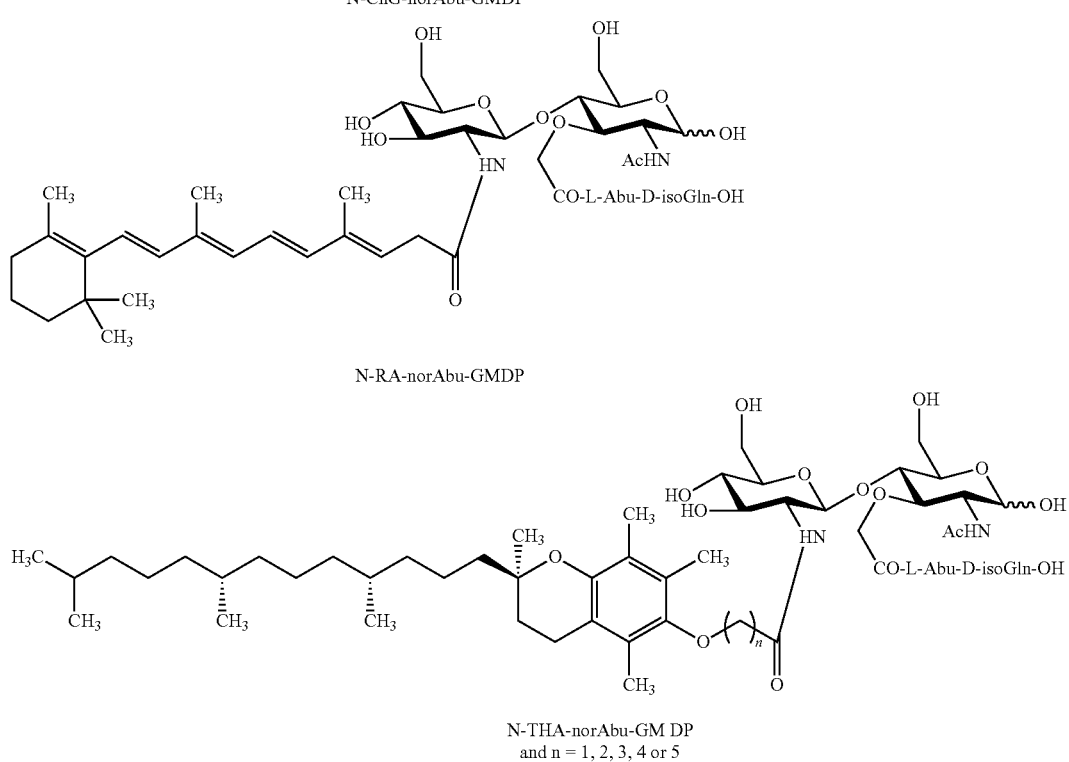
N-RA-norAbu-GMDP
N-THA-norAbu-GMDP
and n = 1, 2, 3, 4 or 5
In another embodiment, the compound of the present invention is a compound of formula I, in which $R_2$ is an acyl group. Preferably, such a compound is selected from:
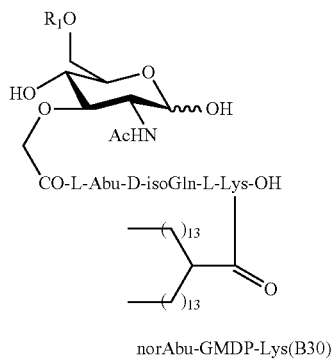
norAbu-GMDP-Lys(B30)
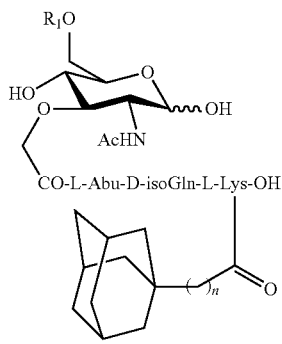
norAbu-MDP-Lys(AA)
and n = 1, 2, 3, 4 or 5

-continued
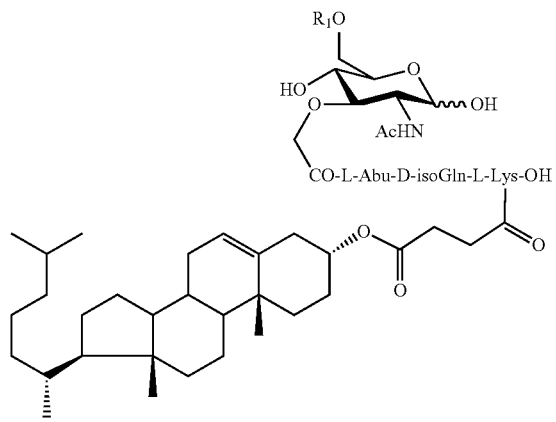
norAbu-MDP-Lys(ChS)
(or the dihydro equivalent norAbu-MDP-Lys(DHChS))
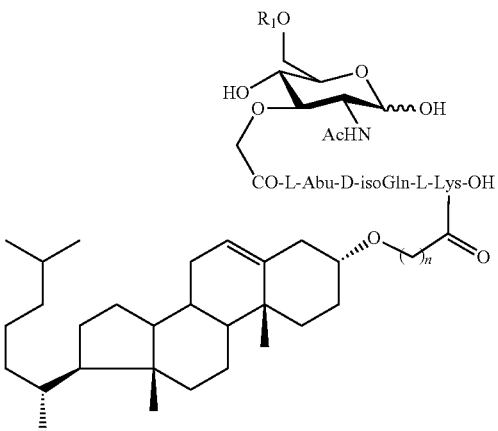
norAbu-MDP-Lys(ChHA)
and n = 1, 2, 3, 4 or 5
(e.g. norAbu-MDP-Lys(ChG))
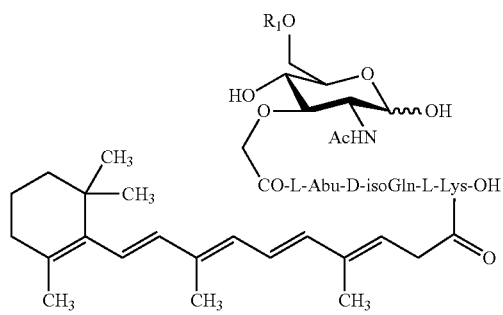
norAbu-GMDP-Lys(RA)
where $R_1$ = hydrogen or a C1 to C5 alkyl group
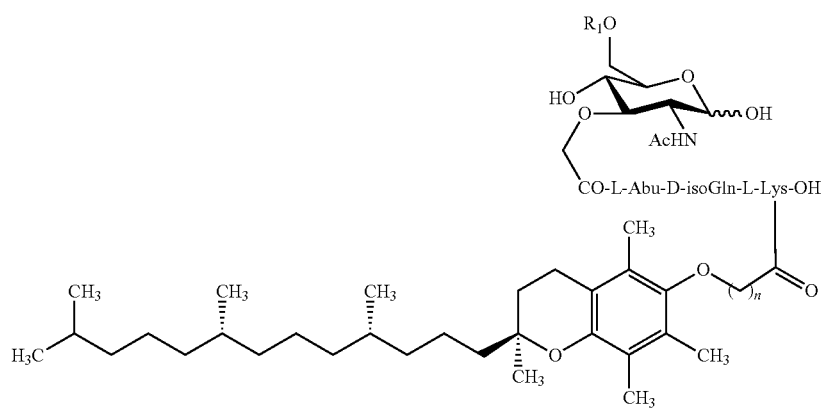
norAbu-GMDP-Lys(THA)
and n = 1, 2, 3, 4 or 5
where $R_1$ = hydrogen or a C1 to C5 alkyl group.

In another embodiment, the compound of the present invention is a compound of formula II, in which $R_2$ is an acyl group. Preferably, such a compound is selected from:
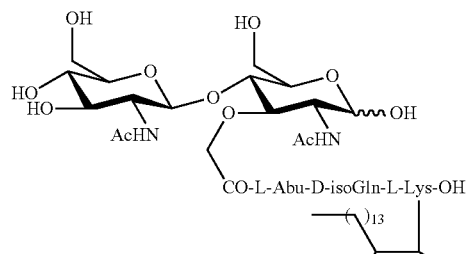
norAbu-GMDP-Lys(B30)
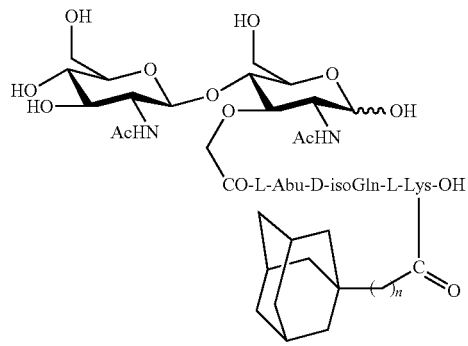
norAbu-GMDP-Lys(AA)
and n = 1, 2, 3, 4, or 5
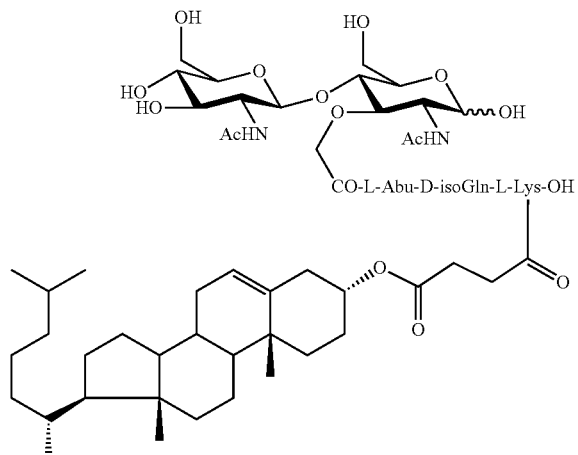
norAbu-GMDP-Lys(ChS)
(or the dihydro ChS equivalent)
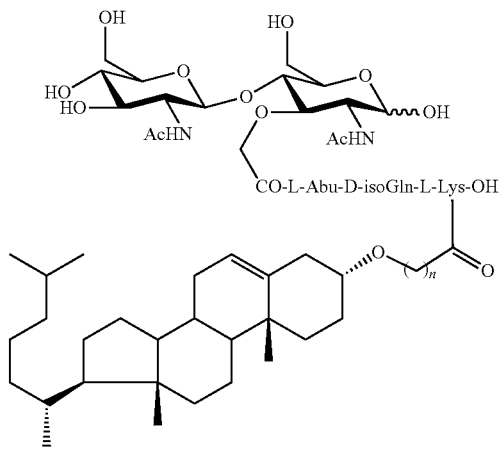
norAbu-GMDP-Lys(ChHA)
and n = 1, 2, 3, 4 or 5
(e.g. norAbu-GMDP-Lys(ChG))
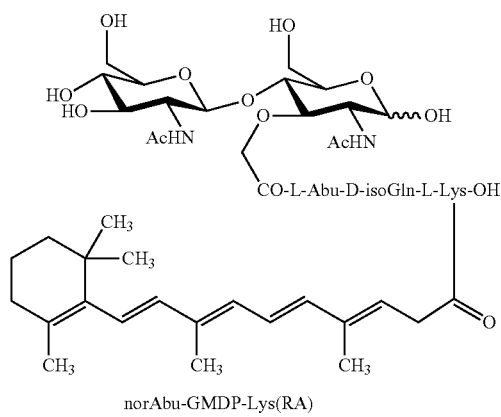
norAbu-GMDP-Lys(RA)

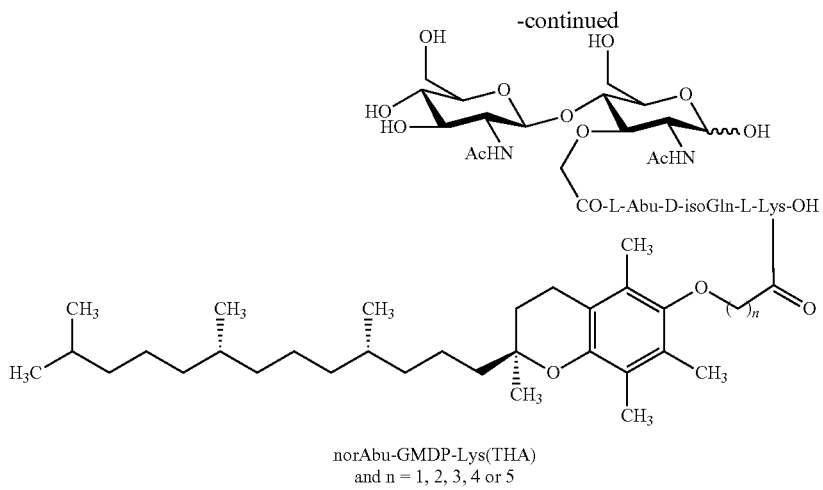

norAbu-GMDP-Lys(THA)
and n = 1, 2, 3, 4 or 5

Immune Modulator (or Immuno Modulator) Composition

In a further aspect, the present invention provides an immune modulator composition comprising:

(i) an antigenic component or source of such a component or source of such a component; and
(ii) an adjuvant comprising a compound of formula I or formula II as described herein, and such as of the first aspect.

The antigenic component may comprise an antigen, or an antigen source, or a precursor thereof or a polynucleotide (e.g. encoding the antigen). The antigen may be isolated or separate or may be on a cell or virus surface. The antigen may thus comprise a virus with an antigen on its surface or a virus, or other vector, or cell, capable of expressing the antigenic component.

In one embodiment, the (source of the) antigenic component comprises a nucleotide sequence (e.g., DNA) capable of expressing (in a host cell) an antigenic amino acid sequence.

In one embodiment, the amino acid sequence (or antigen) comprises, or is part of, a (bacterial or fungal) heat shock protein (or an antigenic fragment thereof), for example that is characteristic for the infection and/or that does not occur in the uninfected host (e.g. a heterologous antigen).

In one embodiment, the present invention thus provides an immune modulator composition comprising:

(i) an antigenic component, such as comprising a (bacterial or fungal) heat shock protein (HSP) or another internal protein or a surface protein or an antigenic fragment thereof; and
(ii) an adjuvant comprising a compound of formula I or formula II wherein $R_1$, $R_2$, $R_3$ and X are as defined herein.

The heat shock protein (or other antigen) may be encoded by a nucleotide sequence capable of being expressed in a host cell (as an antigenic amino acid sequence).

The amino acid sequence (or antigen) may be an antigenic fragment or immunogenic portion of a heat shock protein, such as hsp 60. The heat shock protein hsp 60 may be, or may be derived from, *Trichophyton mentagrophytes*, for example to provide immunity against *Trichophyton* (ringworm) infection.

The components of the immune modulator composition may be administered separately, sequentially or simultaneously, e.g. in combination. If the immune modulator components are administered separately, they may be administered in any order. The antigenic component may be administered first and the adjuvant compound subsequently, or the adjuvant compound may be administered first and the antigenic component may be administered subsequently.

The invention thus also relates to an (immunomodulator) composition comprising an antigenic component (or precursor or source thereof) and an adjuvant, comprising a compound of formula I or formula II, as a combined preparation for simultaneous, separate or sequential use in therapy or prophlyaxis.

Preferably the immune modulator composition further comprises one or more liposomes, which may be the same or different, and preferably contain, comprise or encapsulate (i) the antigenic component and (ii) the compound of Formula I or II, either separately or together.

Preferably the liposomes comprise (a mixture of):
(a) egg-yolk phosphatidylcholine; and
(b) 1-palmitoyl-2-oleoyl-sn-glycero-phosphatidyl glycerol.

In one embodiment, the composition may comprise a compound of formula I, wherein
(i) $R_1$ is stearoyl; X is L-Abu-D-isoGln; and $R_2$ is hydroxyl; or
(ii) $R_1$ is tetradecyl-hexadecanoyl; X is L-Abu-D-isoGln; and $R_2$ is hydroxyl.

In one embodiment, the composition may comprise a compound of formula II, wherein
(i) $R_1$ is stearoyl; X is L-Abu-D-isoGln; $R_2$ is hydroxyl and $R_3$ is acetyl; or
(ii) $R_1$ is tetradecyl-hexadecanoyl; X is L-Abu-D-isoGln; $R_2$ is hydroxyl; and $R_3$ is acetyl; or
(ii) $R_1$ is hydrogen; X is L-Abu-D-isoGln; $R_2$ is hydroxyl; and $R_3$ is stearoyl.

In another embodiment, the composition may comprise a compound of formula Ia or formula IIa, wherein $R_2$ is substituted as described above.

In another embodiment, the composition may comprise a compound of formula Ia or formula IIa, wherein $R_3$ is substituted as described above.

Other Aspects and Features

In a further aspect, the compound of the present invention is provided, as a component of, or contained or comprised in lipidic nano- and/or microparticles. These may be, for example, liposomes, emulsions or micelles. Liposomes, and proteo-liposomes (particles carrying an antigen) are preferable structures for potential application as immunostimulants, adjuvants and/or vaccines. The liposomes may be cationic, neutral, anionic and/or charge-modified, and/or may be functionalized or targeted.

Liposomes (as carriers of muramyl dipeptide analogues, i.e. of compounds of the invention) can play two roles depending on their size. First, large liposomes can stay at the injection site (after the subcutaneous administration) and so may serve as a depot (of the drug, antigenic component or other agent to be delivered). Second, small liposomes, unlike the large ones, can penetrate through the extracellular matrix and reach the lymphatic tissues via the lymphatic capillaries thus delivering the encapsulated drug to the lymphatic tissue macrophages. After phagocytosis of the liposomal component by macrophages or dendritic cells, the drug, antigenic component or other agent can be released into the cytoplasm and interact with intracellular receptors. Targeting of MDP analogues to macrophages can increase the production of various cytokines of therapeutic importance.

Preferably the liposome comprises (a mixture of):
(a) egg-yolk phosphatidylcholine;
(b) 1-palmitoyl-2-oleoyl-sn-glycero-phosphatidyl glycerol; and/or
(c) a compound of the present invention as described herein.

In another aspect, the present invention provides a pharmaceutical composition comprising a composition or a compound as described herein and a pharmaceutically acceptable diluent, carrier or excipient.

In a further aspect, the present invention provides a composition, a liposome or a compound as described herein for use in therapy (or prophylaxis) and/or diagnosis.

In a further aspect, the present invention provides the use of a composition, a liposome or a compound as described herein in the manufacture of a medicament for the treatment (or prophylaxis) of a disorder, condition or disease. The disease may be capable of being modulated by a heat shock protein, as described herein.

Preferably the present invention provides a composition, a liposome or a compound as described herein, suitable for use (and optionally in the manufacture of a medicament) for in at least one of the following:
(a) as an adjuvant, in any form of vaccination, including DNA and other forms of vaccination, for therapeutic and/or preventive purposes, and/or for the treatment and/or prevention of ringworm or dermatophytosis;
(b) up-regulation of antigen-specific Th1 (but not of Th2) responses;
(c) up-regulation of antigen-specific mixed Th1 and Th2 responses;
(d) induction of non-specific resistance to an infection (e.g. bacterial, viral, fungal, parasitic; or for innate immunity), e.g. particularly in an immuno-compromised patient, such as from HIV-infection or immuno-suppression in transplant patients, or in the young or elderly or for hospitalized patients at risk, e.g. in intensive care or after stroke (post-stroke infection, PSI);
(e) treatment (or prevention) of septic shock;
(f) treatment of a radiation accident, illness or disorder;
(g) induction of anti-tumor immunity;
(h) co-therapy in cancer chemo- and/or radiation therapy;
(i) treatment of secondary immunosuppressive states (chemosuppression, radiosupresion), such as by (i) stimulation of hemopoiesis and/or (ii) stimulation of other bonemarrow derived cells and/or (iii) stimulation of mechanisms of innate immunity;
(j) lymphoma, aplastic anaemia or other anaemic condition;
(k) modulation of an autoimmune state, such as Crohn's Disease;
(l) cytokine or hematopoiesis induction, such as for other reasons than in (b-h);
(m) an indication, disease or disorder resulting from, or associated with, GM-CSF low levels or depletion, such as lung disease, slow wound healing, hypercholesterimia, atherosclerosis, diabetes, obesity or metabolic syndrome;
(n) induction of an antibody response (humoral immunity); and/or
(o) induction of cellular immunity.

The present invention also provides (the use of) a composition, a liposome or compound as described herein in the manufacture of a medicament for at least one of the above-listed (a) to (o). The present invention also provides a method of treating, preventing, ameliorating or reducing the incidence of at least one of the above (a) to (o) in a subject, which method comprises the administration to the said subject (in need) of an effective amount of a composition or compound as described herein.

In one embodiment, the vaccination may be DNA vaccination. This may be, for example, for the treatment or prevention of ringworm or of dermatophytosis. In one embodiment, the induction of non-specific resistance to bacterial infections can be used in the treatment or prevention of salmonella. In one embodiment the induction (of non-specific resistance to viral infections) can be used in the treatment or prevention of a viral infection, such as HIV infection or by equine herpes virus.

In another embodiment, the present invention provides a product comprising an immune modulator composition as described herein, containing the antigenic component and adjuvant compound for simultaneous, separate or sequential use in at least one of (a) to (o) above.

Post-stroke infection (PSI) is responsible for the majority of the mortality occurring between 1 week and 1 month after stroke, peaking towards the end of the second week. The effects of PSI on longer-term outcome and other aspects of recovery, such as cognition, mood and quality of life, are largely unknown. The cerebrovascular event itself may result in a systemic immunosuppressed state.

An advantage of the compounds of the present invention is that they may be non-pyrogenic.

Embedding of normuramyl glycopeptide in liposomes may lead to preferential uptake into antigen preventing cells (APCs). Liposome embedded normuramyl glycopeptides may trigger a number of events associated with innate immunity and the overcoming of stress, infection and injury situations.

The liposome (carrying the normuramyl glycopeptides) can have immomodulating material, such as drugs, reversibly attached.

The antigenic material can be proteins or protein fragments or other molecules or other molecule fragments or nucleic acid encoding for proteins or protein fragments.

The antigenic material may be administered at the same or at different times, allowing for the 'boosting' of the immune reaction which can be (a) before or (b) after the administration of the antigen(s). The latter could be important in the case of DNA vaccines, particularly if a more elaborate construct is used to combat hidden or dormant or cryptic viral infections (HBV, HIV, etc.), such as:

inoculation of cells (e.g., muscle) with a plasmid that encodes for (i) viral proteins or protein fragments, (ii) co-stimulatory molecules that results in transfected cells processing the sequence according to (i) in the Golgi apparatus and presenting it in the context of their MHC-I complex and processsing the sequence according to (ii) such that it is presented on the surface, thus resulting in an APC-like cell that can activate $CD8^+$ cells that are specific for the antigen.

As transfection and processing of the sequences may take about one day, there could be a case for transfection and for activation of the immune system at different time points.

Some of the compounds described herein may elicit cellular (Th1) responses only with low antibody (Th2) response. This is particularly suitable for the destruction of cancerous and virus infected cells, such as when the antigenic material is specific for the cancerous cell or virus particle.

These latter applications are suitable for therapeutic use, whereas vaccines otherwise are typically for preventative use.

Process for Preparation of Compounds

In one embodiment, the present invention relates to a process for the preparation of a compound according to Formula I or II. In one embodiment, such a process comprises a step of converting the allyl group of a compound of Formula Ib or IIb,

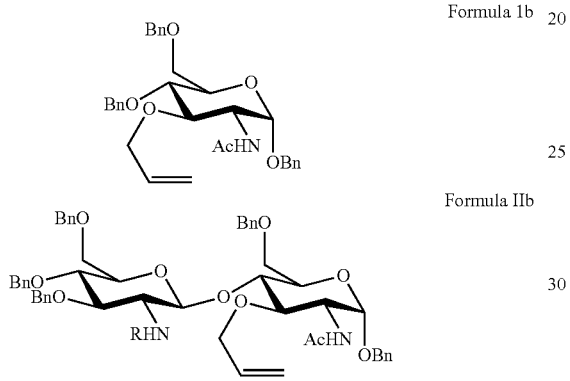

Formula Ib

Formula IIb wherein R is acetyl or trichloroethoxycarbonyl (troc), to a carboxylic acid group, by oxidation, e.g. by reaction with $RuO_4$ generated in situ from a catalytic amount of $RuCl_3$ with less than or equal to 5 mol equivalents, for example 3 to 5 mol equivalents, preferably 4 mol equivalents of sodium periodate ($NaIO_4$) at a temperature of 0-5° C.

The present invention also provides a process for the preparation of a compound of Formula II wherein $R_3$ is an acyl substituent, said process comprising the steps of (i) condensation of a compound of formula IIc with or benzyl ester of peptide chain X,

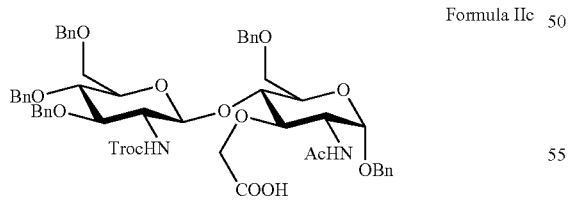

Formula IIc (ii) removal of the Troc protecting group;
(iii) N-acylation of the resulting product with acylchioride derived from the desired fatty acid; and
(iv) hydrogenolysis of the benzyl protecting groups.

The present invention also provides a process for the preparation of a compound of Formula I or Formula II wherein $R_2$ is an amino hydrocarbyl group substituted with an acyl substituent, said process comprising the steps of (i) reacting a compound of Formula Id or IId

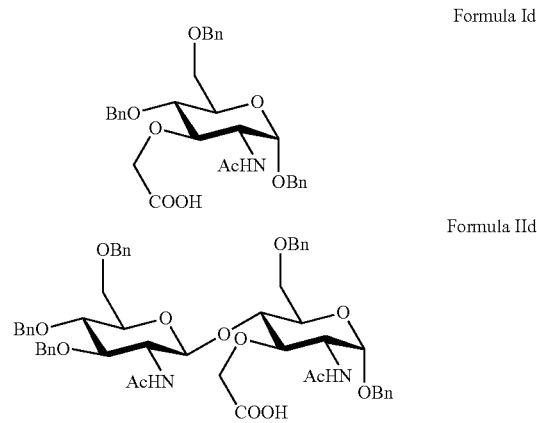

Formula Id

Formula IId with a peptide chain on a solid phase carrier, wherein the peptide chain comprises a ω-amino group in a side chain protected with a 1-(4,4-dimethyl-2,6-dioxocyclohexyliden)-ethyl) group (Dde);

(ii) removing the Dde to provide a carrier-linked glycopeptide synthon with a free ω-amino group;
(iii) N-acylation of the ω-amino group with an appropriate lipophilic carboxylic acid;
(iv) cleavage from the solid phase carrier; and
(v) hydrogenolysis of the benzyl protecting groups.

The present invention also provides intermediate compounds useful in the above processes. Thus, the present invention provides (i) a compound of formula XII

XII (ii) a compound of formula XIII

XIII wherein $R_{13}$ is Troc and $R_{14}$ is —CH═CH$_2$, —COOH, COOCH$_3$ or —CO—X(OBn), wherein X is a peptide chain as defined in claim 1 or in any one of claims 13 to 17, or $R_{13}$ is a substituent of formula VII wherein n is 13 ("B30"), and $R_{14}$ is —CO—X(OBn), wherein X is a peptide chain as defined in claim 1 or in any one of claims 13 to 17;

(iii) a compound of formula XIV

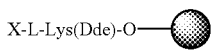     (XIV)

wherein X is a peptide chain as defined in claim 1 or in any one of claims 13 to 17; and

represents a solid phase carrier; and
(iv) a compound of formula XV or XVI

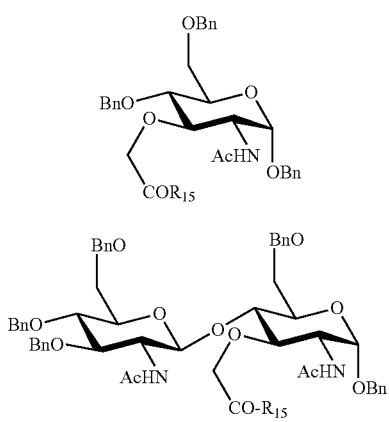

wherein $R_{15}$ is selected from

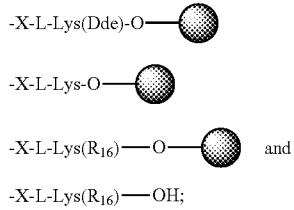

wherein

represents a solid phase carrier; X is a peptide chain as defined in claim 1 or in any one of claims 13 to 17; and $R_{16}$ is

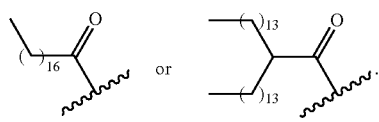

Further aspects of the invention are defined in the appended claims.

Definitions
Hydrocarbyl

As used herein, the term "hydrocarbyl" refers to a group comprising at least C and H that may optionally comprise one or more other suitable substituents. Examples of such substituents may include halo-, acyl, alkoxy-, nitro-, an alkyl group, or a cyclic group. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, silicon and phosphorus.

Hydrocarbon—A typical hydrocarbyl group is a hydrocarbon group. In one embodiment, the hydrocarbyl is a C10 to (C40 or C50 or) C80 saturated or unsaturated and linear or branched hydrocarbon. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some aspects of the present invention, one or more hydrocarbyl groups is independently selected from optionally substituted alkyl group, optionally substituted haloalkyl group, aryl group, alkylaryl group, alkylarylakyl group, and an alkene group.

In some aspects of the present invention, one or more hydrocarbyl groups is independently selected from $C_1$-$C_{10}$ alkyl group, such as $C_1$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_6$ alkyl, $C_7$ alkyl, and $C_8$ alkyl.

In another aspect the hydrocarbyl is preferably a C10 to (C40 or C50 or) C80 saturated or unsaturated and linear or branched alkyl.

In some aspects of the present invention, one or more hydrocarbyl groups is independently selected from aryl groups, alkylaryl groups, alkylarylakyl groups, —$(CH_2)_{1-10}$-aryl, —$(CH_2)_{1-10}$-Ph, $(CH_2)_{1-10}$-Ph-$C_{1-10}$ alkyl, —$(CH_2)_{1-5}$-Ph, $(CH_2)_{1-5}$-Ph-$C_{1-5}$ alkyl, —$(CH_2)_{1-3}$-Ph, $(CH_2)_{1-3}$-Ph-$C_{1-3}$ alkyl, —$CH_2$-Ph, and —$CH_2$-Ph-$C(CH_3)_3$. The aryl groups may contain a hetero atom. Thus the aryl group or one or more of the aryl groups may be carbocyclic or heterocyclic. Typical hetero atoms include O, N and S, in particular N.

In some aspects of the present invention, one or more hydrocarbyl groups are independently selected from alkene groups. Typical alkene groups include $C_1$-$C_{10}$ alkene group, $C_1$-$C_6$ alkene group, $C_1$-$C_3$ alkene group, such as $C_1$, $C_2$, $C_3$, $C_4$, $C_5$, $C_6$, or $C_7$ alkene group. In a preferred aspect the alkene group contains 1, 2 or 3 C=C bonds. In a preferred aspect the alkene group contains 1 C=C bond. In some preferred aspects at least one C=C bond or the only C=C bond is to the terminal C of the alkene chain, that is the bond is at the distal end of the chain to the ring system.

Amino hydrocarbyl—In some aspects of the present invention, one or more hydrocarbyl groups are independently selected from amino hydrocarbyl groups.

The term "amino hydrocarbyl" group as used herein means a group comprising at least C, H and N and may optionally comprise one or more other suitable substituents. Examples of such substituents may include halo-, al koxy-, nitro-, an alkyl group, a cyclic group etc. In addition to the possibility of the substituents being a cyclic group, a combination of substituents may form a cyclic group. If the amino hydrocarbyl group comprises more than one C then those carbons need not necessarily be linked to each other. For example, at least two of the carbons may be linked via a suitable element or group. Thus, the amino hydrocarbyl group may contain hetero atoms. Suitable hetero atoms will be apparent to those skilled in the art and include, for instance, sulphur and nitrogen.

In one embodiment of the present invention, the amino hydrocarbyl group is a amino hydrocarbon group.

Here the term "amino hydrocarbon" means a group comprising N and at least one alkyl group, and/or an alkenyl group, and/or an alkynyl group, which groups may be linear, branched or cyclic, and/or an aryl group. The term amino hydrocarbon also includes those groups but wherein they have been optionally substituted. If the amino hydrocarbon is a branched structure having substituent(s) thereon, then the substitution may be on either the hydrocarbon backbone or on the branch; alternatively the substitutions may be on the hydrocarbon backbone and on the branch.

In one further aspect the term "amino hydrocarbyl" group as used herein means a group of the formula —NR$_8$R$_9$, wherein R$_8$ is H or a hydrocarbyl group (such as a hydrocarbon group) and R$_9$ is a hydrocarbyl group (such as a hydrocarbon group).

Acyl is a group having the formula RC(O)— where R is a hydrocarbyl group.

Alkyl is straight-chain or branched alkyl bonded in any position.

Suitable substituents of optionally substituted alkyl are especially free or functionally modified hydroxyl or mercapto groups, such as etherified or esterified hydroxyl or mercapto groups with alcohols and acids specified below (for example lower alkoxy or lower alkylmercapto groups), free or functionally modified amino group (for example mono- or di-alkylamino group or acylamino group), halogen atoms or free or functionally modified carboxyl groups, such as lower alkoxycarbonyl groups or free or mono- or disubstituted carbamoyl group at the nitrogen atom. The substituted alkyl radical, such as a lower alkyl radical, can carry one, two or more identical or different substituents, especially free hydroxyl groups or halogen atoms.

Aryl radicals are especially monocyclic and bicyclic (phenyl and naphthyl). They can be optionally mono- or poly-substituted (for example by lower alkyl, free, esterified or etherified hydroxyl or mercapto group, functionally modified amino group, and/or halogen atoms).

Arylalkyl is especially aryl-lower alkyl, wherein aryl has the meaning given above. Aryl-lower alkyl represents especially benzyl or phenylethyl, the phenyl nucleus can be mono, di- or poly-substituted.

Optionally substituted arylalkyl radicals are especially those radicals that are optionally mono-, di- or poly-substituted in the aromatic nucleus.

Cycloalkyl is especially cycloalkyl having 5 or 6 carbon atoms, such as cyclopentyl or cyclohexyl, and that may have one or two double bonds, and can also be optionally mono- or poly-substituted.

Cycloalkyl alkyl is a radical wherein the cycloalkyl moiety has the meaning given above and the alkyl moiety may have one or more double bonds, for example retinyl, and in cycloalkyl-lower alkyl the lower alkyl moiety represents especially methyl or ethyl.

Poly-cycloalkyl can be unsubstituted (for example adamantyl), or may have one or more double bonds, and can also be optionally mono- or poly- substituted, as are poly-cycloalkyl radicals of steroid type (for example cholesteryl).

Poly-cycloalkyl alkyl is a radical wherein the poly-cycloalkyl moiety has the meaning given above and the alkyl moiety may have one or more double bonds, and in poly-cycloalkyl-lower alkyl the lower alkyl moiety represents especially methyl or ethyl.

Suitable substituents of optionally substituted aryl, cycloalkyl or polycycloalkyl are especially lower alkyl, free or functionally modified hydroxyl or mercapto groups, such as hydroxyl or mercapto groups etherified or esterified with the alcohols and acids specified below (for example lower alkoxy or lower alkylmercapto groups), free or functionally modified amino groups (for example mono- or di-alkylamino groups or acylamino groups), halogen atoms or free or functionally modified carboxyl groups, such as lower alkoxycarbonyl groups or free or mono- or disubstituted carbamoyl group at the nitrogen atom. The substituted alkyl radical, such as a lower alkyl radical, can carry one, two or more identical or different substituents, especially lower alkyl, free hydroxyl groups or halogen atoms.

Nitrogen-containing heterocyclyl is especially the radical of 5- or 6-membered heterocyclic compounds containing one or two nitrogen atoms in the ring. The radical can be unsaturated or alternatively saturated and can contain, for example, a condensed-on phenyl radical. Such radicals may be, for example, pyrolyl, indolyl, pyridyl or imidazolyl radicals.

Nitrogen-containing heterocyclyl-lower alkyl is a radical wherein the nitrogen-containing heterocyclyl moiety has the meaning given above and the lower alkyl radical is especially methyl or ethyl.

A functionally modified carboxyl group is optionally esterified or amidated carboxyl group, it is especially a carboxyl group esterified by alcohols specified below, or a carbamoyl group that is unsubstituted at the nitrogen atom or mono- or disubstituted by alkyl (especially lower alkyl), by aryl (especially by phenyl), or by arylalkyl (especially by benzyl). The carboxyl group can, however, also carry an alkylene radical, such as tetramethylene or pentamethylene radical.

As functionally modified hydroxyl or mercapto groups special mention may be made of hydroxyl or mercapto groups etherified or esterified by alcohols and acids specified below (for example lower alkoxy, lower alkylmercapto, alkanoyloxy or alkanoylmercapto groups).

A functionally modified amino group is a mono- or di-substituted amino group wherein the substituents can be alkyl, lower alkyl, aryl, aralkyl, cycloalkyl, poly-cycloalkyl cycloalkyl-lower alkyl, poly-cycloalkyl-lower alkyl or acyl.

As functionally modified amino-lower alkyl special mention may by made of mono- or di-lower alkylamino-lower alkyl or acylated amino-lower alkyl (for example methylamino-lower alkyl, ethylamino-lower alkyl, dimethylamino-lower alkyl, diethylamino-lower alkyl and alkanoylamino-lower alkyl).

Carboxyl-, alkoxycarbonyl- or aminocarbonyl-lower alkylamino radical represent aminoacid radical having free or functionally modified carboxyl group (for example free or at carboxyl group functionally modified glycylamino, alanyl, valylamino or isoleucyl radical).

A long-chain aliphatic carboxylic acid is especially one that has from 10 to 80 carbon atoms and that may also have 1 or more double bonds and can be linear or branched. Preferred are those having up to 30 carbon atoms, especially from 18 to 22 carbon atoms, or natural or synthetic mycolic acids.

Suitable substituents of optionally substituted carboxylic acids are especially free or modified hydroxyl or mercapto groups, such as etherified or esterified hydroxyl or mercapto groups (for example lower alkoxy or lower alkylmercapto groups), halogen atoms, or free or functionally modified carboxyl groups, such as lower alkoxycarbonyl groups or free or mono- or disubstituted carbamoyl group at the nitrogen atom. The substituted acyl radical, such as a lower acyl radical, can carry one, two or more identical or different substituents, especially free hydroxyl groups or halogen atoms.

A long-chain aliphatic alcohol is especially an alcohol that has up to 30 carbon atoms, especially from 10 to 22 carbon atoms, and that may also have one or more double bonds and may be straight or branched. Preferred are those alcohols which contain from 12 to 18 carbon atoms and terminal hydroxyl groups.

Cycloalkanol, poly-cycloalkanol, cycloalkyl alkanol and poly-cycloalkyl alkanol are alcohols wherein cycloalkyl, poly-cycloalkyl, cycloalkyl alkyl and poly-cycloalkyl alkyl have the meaning given above.

Those radicals and compounds that are termed "lower" in connection with the present description and patent claims preferably contain up to and including 10 carbon atoms, preferably up to and including 7 carbon atoms and especially up to and including 4 carbon atoms.

Lower alkyl is, for example, n-propyl, n-butyl, isobutyl, sec.-butyl or tert.-butyl, also n-pentyl, n-hexyl, isohexyl or n-heptyl, and especially methyl or ethyl. In aryl-lower alkyl, cycloalkyl-lower alkyl or heterocyclyl-lower alkyl radicals the lower alkyl radical is especially methyl or ethyl, the aryl, cycloalkyl or heterocyclyl radicals have the meaning given above.

Lower alkoxy is, for example, n-propoxy, n-butoxy, isobutoxy, sec.-butoxy or tert.-butoxy and especially methoxy or ethoxy.

Lower alkylmercapto is, for example n-propylmercapto, n-butylmercapto isobutylmercapto, sec.-butylmercapto and especially methylmercapto or ethylmercapto.

Lower alkylendioxy is especially methylendioxy, eyhylendioxy or propylendioxy.

Halogen represents fluorine or bromine but especially chlorine.

Lower alkanoyl is especially propionyl or butyryl but more especially acetyl.

Synthetic mycolic acids are especially α-alkyl-β-hydroxyacanecarboxylic acids, wherein the alkyl radical in the α-position contains from 1 to 20, especially 1 to 14, carbon atoms, and the alkanecarboxylic acid contains from 20 to 80, especially from 30 to 34, carbon atoms. They can also contain further hydroxyl groups, and oxo groups.

Natural mycolic acids are especially those which can be isolated from living organisms, such as bacteria (for example Mycobacteria).

Lipids are fatty acids and their derivatives, and substances related biosynthetically or functionally to these compounds. Thus a lipid may be a fatty acid (e.g., stearic acid, palmitic acid), condensed with a polar head group molecule, for example glycerol or phosphoglycerol. The term "lipid" also encompasses sterol lipids such as cholesterol.

Lipid acyl is a group represented by the formula L-C(O), wherein L is a lipid moiety.

The compounds of the general formulas I and II can be present in the form of isomeric mixtures or as the pure isomers, and the invention relates to both of them. For example the hydroxyl group on the reducing end of the sugar subunit of compounds I and II can have a configuration of the α- or β-anomer.

The invention relates generally also to the salts of compounds of the formulas I, and II having any salt-forming groups, as is for example free carboxyl groups or amino groups, include internal salts (zwitterions).

Heat Shock Proteins

Heat shock proteins (hsps) are suitable antigens and/or adjuvants and can be from prokaryotic and eukaryotic sources.

Hsps—such as hsp60, 70 or 90—are generally found in the cytosol and mitochondria.

In one embodiment, the hsp is hsp60. Preferably, the hsp—such as hsp60—is or is derived from *Trichophyton*, such as *Trichophyton mentagrophytes* (e.g. TM179).

In one embodiment, hsp60 is or is derived from *Trichophyton mentagrophytes* (e.g. TM179) and comprises the sequence set forth in SEQ ID No 1 or 2 or is a variant, homologue, derivative or fragment thereof.

Nucleotide Sequences

The nucleotide sequences may be DNA or RNA. The DNA or RNA may be of genomic or synthetic or of recombinant origin (e.g. cDNA), or combinations thereof. The nucleotide sequence may be double-stranded or single-stranded whether representing the sense strand or the antisense strand or combinations thereof. The nucleotide sequence may be a gene or part thereof of a silencing gene.

Amino Acid Sequence

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

The amino acid sequence may be isolated from a suitable source, or it may be made synthetically or it may be prepared by use of recombinant DNA techniques.

Formulation

The component(s), e.g. adjuvant and/or antigen, may be formulated into a pharmaceutical composition, such as by mixing with one or more of a suitable carrier, diluent or excipient, by using techniques that are known in the art.

Pharmaceutical, Vaccine and Immunomodulator Compositions

Pharmaceutical and other types of compositions of the present invention may comprise a therapeutically effective amount of a compound, as described herein.

The (pharmaceutical) compositions may be for human or animal usage in human and veterinary medicine and will typically comprise any one or more of a (pharmaceutically or veterinarily) acceptable diluent, carrier, or excipient. Acceptable carriers or diluents for such use are well known in the pharmaceutical art. The choice of (pharmaceutical) carrier, excipient or diluent can be selected with regard to the intended route of administration and standard pharmaceutical practice. The (pharmaceutical) compositions may comprise as—or in addition to—the carrier, excipient or diluent any suitable binder(s), lubricant(s), suspending agent(s), coating agent(s), solubilising agent(s). The compound may be coated or located on one or more (e.g. metallic, such as gold) particles.

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered orally or by using a mini-pump or by a mucosal route, for example, as a nasal spray or aerosol for inhalation or ingestable solution, or parenterally. Here the composition may be formulated in an injectable form, for delivery, by, for example, an intravenous, intramuscular (to the muscle) or subcutaneous route. Alternatively, the formulation may be designed to be administered by a number of routes. One can deliver to the muscle cells, such as APCs (by incorporation of co-stimulatory molecules, such as B7) which may be followed by subsequent enhancement of the activation of T-cells.

If the compound is to be administered (e.g. mucosally) through the (gastro)intestinal mucosa, it is preferable that it should be able to remain stable during transit though the gastrointestinal tract. For example, it may be resistant to proteolytic degradation, stable at acid pH and/or resistant to the detergent effects of bile. The compound may be administered through intestinal mucosa (e.g. M-cells or dendritic protrusions through the basal membrane to the interface with the intestinal lumen).

Where appropriate, the (pharmaceutical) compositions may be administered by inhalation, in the form of a suppository or pessary, topically (in the form of a lotion, solution, cream, ointment or dusting powder, or by use of a skin patch), orally (in the form of tablets containing excipients such as starch or lactose, or in capsules or ovules either alone or in admixture with excipients, or in the form of elixirs, solutions or suspensions containing flavouring or colouring agents), or the (pharmaceutical) compositions can be injected parenterally, for example intravenously, intramuscularly or subcutaneously. For parenteral administration, the compositions may be best used in the form of a sterile aqueous solution which may contain other substances, for example one or more (or enough) salts and/or monosaccharides, for example to make the solution isotonic with blood. For buccal or sublingual administration the compositions may be administered in the form of tablets or lozenges which can be formulated in a conventional manner.

The compound(s) may be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Pharmaceutical Combinations

The compounds of the present invention may be administered with one or more other pharmaceutically active substances.

It will be understood that these regimes include the administration of the various substances sequentially, simultaneously, separately or together.

Administration

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components may be administered alone but will generally be administered as a pharmaceutical composition—e.g. when the components are in admixture with a suitable pharmaceutical excipient, diluent or carrier selected with regard to the intended route of administration and standard pharmaceutical practice. The adjuvant compound may be administered later, e.g. after the antigen For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual delivery.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Immune Modulator

The preparation of immune modulators—such as vaccines—which contain one or more substances as an active ingredient(s), is known to one skilled in the art.

Typically, such immune modulators are prepared as injectables, either as liquid solutions or suspensions; solid forms suitable for solution in, or suspension in, liquid prior to injection may also be prepared. The preparation may also be emulsified, or the active ingredient(s) encapsulated in liposomes. The active ingredients are often mixed with excipients, which are pharmaceutically acceptable and compatible with the active ingredient. Suitable excipients are, for example, water, saline, dextrose, glycerol, ethanol, or the like and combinations thereof. Alternatively, the vaccine may be prepared, for example, to be orally ingested and/or capable of inhalation.

In addition, if desired, the vaccine may contain minor amounts of auxiliary substances such as wetting or emulsifying agents and pH buffering agents.

The invention also contemplates a combined preparation comprising:
(i) an antigenic component; and
(ii) an adjuvant comprising a compound of formula I or formula II (such as wherein $R_1$, $R_2$, $R_3$ and X are as defined above),
for simultaneous, separate or sequential use for treating and/or preventing a disease or condition, or for therapy or for diagnosis.

Either the antigenic component may be administered first, or vice versa.

Antigens (and Antigenic Components)

As used herein, an "antigen" or an "antigenic component" may be a pure substance, a mixture of substances or soluble or particulate material (including cells or cell fragments or cell sonicate). In this sense, the term includes any suitable antigenic determinant, cross-reacting antigen, alloantigen, xenoantigen, tolerogen, allergen, hapten, and immunogen, or parts thereof, as well as any combination thereof.

The antigen (or source thereof) may be encoded (and expressed, later, once in the body) by a polynucleotide, e.g. DNA, which may be present in a vector (e.g. a plasmid)

Alternatively the antigen itself may be a polynucleotide (e.g. comprising a CpG motif) since the structure and/or sequence can itself generate an immune response.

Preferably, the antigen is an antigen of an infectious agent that causes an infectious disease.

Thus, in one embodiment, the antigenic determinant is an antigenic determinant that is or is derived from a heat shock protein from *Trichophyton mentagrophytes* (e.g., *Trichophyton mentagrophytes* TM179).

In one embodiment, the antigenic determinant is or is derived from an antigenic determinant from hsp60 from *Trichophyton mentagrophytes* (e.g. *Trichophyton mentagrophytes* TM179).

In one embodiment, the antigenic determinant is or is derived from an antigenic determinant comprising 270 amino acids from hsp60 from *Trichophyton mentagrophytes* (e.g., *Trichophyton mentagrophytes* TM179).

The vaccine may be a "preventative" or "prophylactic" vaccine i.e. a vaccine which is administered to naive individuals to prevent the development of a condition, such as by stimulating protective immunity. The antigens may be administered as part of such a vaccine.

The vaccine may be a "therapeutic" vaccine i.e. a vaccine, which is administered to individuals with an existing condition to reduce or minimise the condition or to abrogate the immunopathological consequences of the condition.

Adjuvant

The term 'adjuvant' as used herein usually means an entity capable of augmenting and/or participating in the influencing of an immune response. An adjuvant can be any substance or mixture of substances that can assist, increase, downregulate, modify or diversify an immune response to an antigen.

The immune modulator composition and/or pharmaceutical composition according to the present invention may comprise one or more adjuvants, which may enhance the effectiveness of the immune modulator composition and/or pharmaceutical compositions.

Preferably, the adjuvant is one or more of the compound(s) described herein, in accordance with the first aspect.

The composition of the invention may be able to provide bacterial, fungal, viral, parasatic and/or innate immunity, or provide protection against invading organisms and/or cancer.

Additional adjuvants may include but are not limited to aluminium hydroxide, aluminium phosphate, aluminium potassium sulphate (alum), beryllium sulphate, silica, kaolin, carbon, water-in-oil emulsion, oil-in-water emulsion, muramyl dipeptide, bacterial endotoxin, lipid X, polyribonucleotides, sodium alginate, lanolin, lysolecithin, vitamin A, interleukins such as interleukin 2 and interleukin-12, saponin, influenza (or flu) or other virus subunits or viroosomes (e.g. Berna, such as Inflexal Berna V) liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Only aluminium hydroxide is approved for human use. Some of the other adjuvants, such as *M. vaccae* for example, have been approved for clinical trials.

The adjuvant, compound of the invention and/or antigen (or precursor thereof) can be attached, adhered to or in contact with metal (e.g. gold) particles. Such (e.g. coated) particles may be fired at or into the skin, such as by a (helium) gun, as part of an efficient vaccine delivery system. However, unlike conventional vaccines, these vaccines may not always require a traditional adjuvant component. The immune modulator composition as defined herein may suitably be used in conjunction with such particles to augment or participate in the influencing of the immune response.

Animal Test Models

In vivo models may be used to investigate and/or design therapies or therapeutic agents to treat cancer. The models could be used to investigate the effect of various tools/lead compounds on a variety of parameters, which are implicated in the development of or treatment of a cancer. The animal test model will be a non-human animal test model.

Liposomes

Liposomes are typically (completely) closed or spherical structures, usually comprising one or more lipid bilayer membranes. They can thus contain, define or form an (encapsulated) aqueous volume. Liposomes may contain many concentric lipid bilayers separated by an aqueous phase (multilamellar vesicles or MLVs), or alternatively, they may comprise a single membrane bilayer (unilamellar vesicles).

Liposomes can be formed when a (thin) lipid film or lipid cake is hydrated, e.g. so and (stacks of) liquid crystalline bilayer(s) may become fluid and swell. The hydrated lipid sheets can detach during agitation and may self-close to form large, multilamellar vesicles (MLVs). This may prevent interaction of water with the hydrocarbon core or the bilayer, e.g. at the edges. Once these particles have formed, reducing the size of the particle may require energy input in the form of sonic energy (sonication) or mechanical energy (extrusion). Unilamellar vesicles can be prepared by a variety of methods, including extrusion, detergent dialysis, reverse evaporation, and ethanol injection.

Typically, a hydrophilic active agent can be encapsulated into a liposome or delivery vehicle, such as by hydrating the dry lipid film with an aqueous solution of active agent. In this manner, the agent can be passively encapsulated in the interlamellar space(s) of the liposome or delivery vehicle. Alternatively, a hydrophilic, water-soluble active agent may be encapsulated in the liposome or delivery vehicle by a reverse loading technique. This method can involve the dispersal of a neutrally charged drug or other active agent in the aqueous phase of a liposome or delivery vehicle preparation. This can allow the uncharged drug or other active agent to permeate via the lipid bilayer. The pH of the liposome or delivery vehicle solution can be adjusted to create a charge on the active agent, e.g. rendering the active agent unable to pass back through the bilayer and into the external medium. One can thereby entrap the active agent in the liposome or delivery vehicle.

A lipophilic active agent (e.g., hydrophobic drug or other active agent or water-insoluble drug) may be incorporated into the liposome or delivery vehicle by partitioning. In this respect, the agent can be dissolved, along with the lipophilic ingredient(s), in a suitable non-polar solvent. The resulting solution can either be dried and mixed with a polar solvent as described above, or directly added to the aqueous phase and extracted. In this manner, the agent can be incorporated into the lipid portion of the liposome or delivery vehicle bilayer. The agent may be dissolved in a third solvent or solvent mix and can be added to the mixture of polar solvent, e.g. with the lipid film, such as prior to homogenising the mixture.

The lipid bilayer may comprise of two lipid monolayers, e.g. having a hydrophobic "tail" region and a hydrophilic "head" region. In the membrane bilayer, the hydrophobic (nonpolar) "tails" of the lipid monolayers can orient toward the centre of the bilayer, whereas the hydrophilic (polar) "heads" can orient toward the aqueous phase.

The lipid components that may be used in the liposomes are generally described in the literature. Generally, these are phospholipids—such as phosphatidylcholine, phosphatidylethanola mine, phosphatidylglycerol, phosphatidylserine, phosphatidic acid, phosphatidylinositol and/or sphingolipids. Additional components, for example, sterols—such as cholesterol—or other components—such as fatty acids (e.g. stearic acid, palmitic acid), dicetyl phosphate or cholesterol hem isuccinate, may be used. Moreover, the liposome membrane can also contain preservatives. The liposome membrane may also contain a component which can modify the dispersion behaviour. They include, for example, PEGylated derivatives of phosphatidylethanolamine, lipids—such as GM 1—or conjugates of sugars and hydrophobic components—such as palmitic or stearic acid esters of dextran. The liposome may be a cationic liposome.

The basic structure of liposomes may be made by a variety of techniques known in the art.

For example, liposomes can be prepared using known processes whereby lipids suspended in organic solvent are evaporated under reduced pressure to a dry film in a reaction vessel. An appropriate amount of aqueous phase is then added to the vessel and the mixture agitated. The mixture is then allowed to stand, essentially undisturbed for a time sufficient for the multilamellar vesicles to form.

Liposomes may be reproducibly prepared using a number of currently available techniques. The types of liposomes which may be produced using a number of these techniques include small unilamellar vesicles (SUVs), reverse-phase evaporation vesicles (REV), stable plurilamellar vesicles (SPLV), and large unilamellar vesicles produced by an extrusion technique Preferably, liposomes can comprise a mixture of: (a) egg-yolk phosphatidylcholine; and (b) 1-palmitoyl-2-oleoyl-sn-glycero-phosphatidyl glycerol.

The liposomes may be adapted to target or be administered to certain cells or tissues (as discussed earlier), for example immune cells, e.g. macrophages, or dendritic cells.

Liposomal Vaccine and Immunomodulator Delivery

The compounds of the invention may thus be located in a liposome, for example (partly or wholly) located or embedded within a bilayer. This may be assisted by one or more parts of the molecule being hydrophobic, e.g. a hydrophobic tail. Alternatively or in addition, the adjuvant compound (and laos the antigen) can be located partially, or wholly, on the surface of the liposome or other delivery vehicle. The molecule(s) could then contact external fluids. This positioning may allow interaction of the molecule(s) with cells, and may assist with causing phagocytosis.

The antigenic component, or nucleic acid producing the antigenic component, may be separate from the adjuvant compound, but in the same composition. This too may be associated with the liposome or other delivery vehicle, for example inside it and/or on the surface. So both the antigenic component, or nucleic acid producing the antigenic component, and the adjuvant compound may be located inside, or (wholly or partially) on the surface of, such a vehicle.

The liposome, or a compound according to the present invention, may also form, be a part of, or be associated with, a delivery vehicle for an agent, alone or together with an antigenic component, for example in an immune modulator composition.

Such vehicles can be ABCD nanoparticles (Kostarelos, K. & Miller, Chem. Soc. Reviews 34, 970-994, 2005). ABCD nanoparticles comprise one or more agents (A), condensed within functional concentric layers of chemical components designed for biological interaction (D), biological stability (C) and cellular entry/intracellular trafficking and overall packaging (B). Component B typically comprises lipids.

Components C and D are optional, such that the nanoparticles may comprise AB core nanoparticles (for example comprising one or more agents encapsulated by liposomes/micelles B in a non-covalent manner), ABC, ABD or ABCD particles.

Component C comprises a chemical component having stealth/biocompatibility properties, typically a polymer, such as mono or bifunctional poly(ethylene glycol) ("PEG"), poly (vinyl alcohol) ("PVA"); other poly(alkylene oxides) such as poly(propylene glycol) ("PPG"); and poly(oxyethylated polyols) such as poly(oxyethylated glycerol), poly(oxyethylated sorbitol), and poly(oxyethylated glucose), and the like.

Advantageously, component C is linked to component B via a covalent interaction between one or more groups (e.g. functional groups) of the respective components. In one embodiment, the covalent interaction may occur between one or more aldehyde and/or ketone groups of the component C (e.g. polymer) and one or more aminoxy functional groups of one or more lipids B of the liposome.

In a preferred embodiment, the polymer is polyethylene glycol (PEG) with a functional aldehyde and/or ketone group or a chemical derivative thereof. Different sizes of PEG may be used, and may include mono-and bis-aldehyde PEG. In a preferred embodiment, the polymer, such as PEG, has a molecular weight of from 1000 to 5000, preferably about 2000.

In one embodiment, the delivery vehicles of the present invention incorporate aminoxy lipids (see, e.g. WO02/48170) coupling to PEG aldehydes (see, e.g. WO2006/016097).

When present, component C, e.g. a polymer such as PEG, is typically incorporated in an amount of 0.1 to 15 mol % of the combined lipid components (B).

Component D can comprise a chemical component designed for biological targeting. Targeted delivery may therefore be achieved by the addition of one or more components D (e.g. targeting moieties)—such as peptides, proteins, carbohydrates, antibodies, antigens and/or other ligands—to the liposome, preferably the surface of the liposome. Advantageously, the component(s) D are coupled to the surface of the liposome via an interaction between the component(s) D and one or more lipids B of the liposome that are exposed at the liposome surface.

Advantageously, this may enable delivery of the agent A to specific cells, organs and tissue that can bind the component(s) D (such as the targeting moiety). Typically, the binding between the cells, organs and tissues will be via a specific binding between cells, organs and/or tissues and the component(s) D.

When present, the amount of component D will depend on the desired application. Typically, component D is incorporated in an amount of 0.05 to 10 mol % of the combined lipid components (B).

The nanoparticles may be made by a "pre-modification" method, wherein a liposome comprising the desired B and optional C components is formulated prior to addition of the one or more agents. ABC nanoparticles comprising PEG may also be formulated using a "post-modification" method, which involves first forming AB core nanoparticles and then mixing with PEG-lipid in the form of micelles. Alternatively, the C component, such as PEG-polymer, may be equipped with reactive functional groups that bioconjugate in aqueous conditions with complementary functional groups presented on the outside surface of the AB nanoparticle. Such a "post-coupling" process may extend by analogy to formulation of ABD or ABCD nanoparticles. Such suitable delivery vehicles are also described in WO 03/047549.

The compounds according to the present invention may be combined with the delivery vehicle by adding the compound to ABCD (or AB, ABC or ABD) nanoparticles, forming an admixture. Alternatively, the nanoparticles may be formulated together with the compound, for example by mixing the compound with the lipids of component B. Thus, the compound of the present invention may reside in the B layer of the nanoparticles to convey immunomodulator action of the compounds on to certain cells as targeted by the D layer of the ABCD nanoparticles. The compounds and/or antigens may also be attached to the D-layer to facilitate interaction with APCs.

Host Cells

As used herein, the term "host cell" refers to any cell that comprises nucleotide sequences or other substances that are of use in the present invention.

Host cells may be transformed or transfected with a nucleotide sequence contained in a vector e.g. a cloning vector. Preferably, said nucleotide sequence is carried in a vector for the replication and/or expression of the nucleotide sequence. The cells will be chosen to be compatible with the said vector and may for example be eukaryotic (e.g. mammalian cells), prokaryotic (for example bacterial), fungal, yeast or plant cells.

Constructs

Nucleotide sequences may be present in a construct.

The term "construct"—which is synonymous with terms such as "conjugate", "cassette" and "hybrid"—includes a nucleotide sequence directly or indirectly attached to a promoter. An example of an indirect attachment is the provision of a suitable spacer group such as an intron sequence, such as the Sh1-intron or the ADH intron, intermediate to the promoter and the nucleotide sequence of the present invention. The same is true for the term "fused" which includes direct or indirect attachment. In some cases, the terms do not cover the natural combination of the nucleotide sequence coding for the protein ordinarily associated with the wild type nucleotide sequence promoter and when they are both in their natural environment.

The construct may even contain or express a marker, which allows for the selection of the nucleotide sequencetic construct. Various markers exist which may be used, such as for example those encoding antibiotic resistance.

DNA Expression Systems (e.g. Vectors)

Aspects of the present invention relate to a vector comprising a nucleotide sequence.

As is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising nucleotide sequences and/or expressing the proteins encoded by the nucleotide sequences. Examples of vectors used in recombinant DNA techniques include, but are not limited to, plasmids, chromosomes, artificial chromosomes or viruses.

The term "vector" includes expression vectors and/or transformation vectors and encompasses viral vectors.

The term "expression vector" means a construct capable of in vivo or in vitro/ex vivo expression.

The term "transformation vector" means a construct capable of being transferred from one species to another.

In some applications, nucleotide sequences are operably linked to a regulatory sequence which is capable of providing for the expression of the nucleotide sequence, such as by a chosen host cell. By way of example, a vector comprising a nucleotide sequence is operably linked to such a regulatory sequence, i.e. the vector is an expression vector.

Expression Vector

Nucleotide sequences may be inserted into a vector that is operably linked to a control sequence that is capable of providing for the expression of the coding sequence by the host cell.

Nucleotide sequences produced by a host recombinant cell may be secreted or may be contained intracellularly depending on the sequence and/or the vector used. As will be understood by those of skill in the art, expression vectors can be designed with signal sequences, which direct secretion of the nucleotide sequence through a particular prokaryotic or eukaryotic cell membrane.

Variants/Homologues/Derivatives/Fragments

The present invention also encompasses the use of variants, homologues, derivatives or fragments of any of the nucleic and/or amino acid sequences described herein and includes any substitution of, variation of, modification of, replacement of, deletion of or addition of one (or more) nucleotides or amino acids from or to the sequence providing the resultant sequence has at least the same activity as the sequence from which it is derived.

Here, the term "homologue" means an entity having a certain homology with the subject amino acid sequences and the subject nucleotide sequences. Here, the term "homology" can be equated with "identity".

In the present context, a homologous sequence is taken to include an amino acid or nucleotide sequence, which may be at least 75, 85 or 90% identical, preferably at least 95 or 98% identical to the subject sequence. Although homology can also be considered in terms of similarity (i.e. amino acid residues having similar chemical properties/functions), in the context of the present invention it is preferred to express homology in terms of sequence identity.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

DRAWINGS

The present invention will now be described in further detail by way of example only with reference to the accompanying figures in which.

Figure 9:
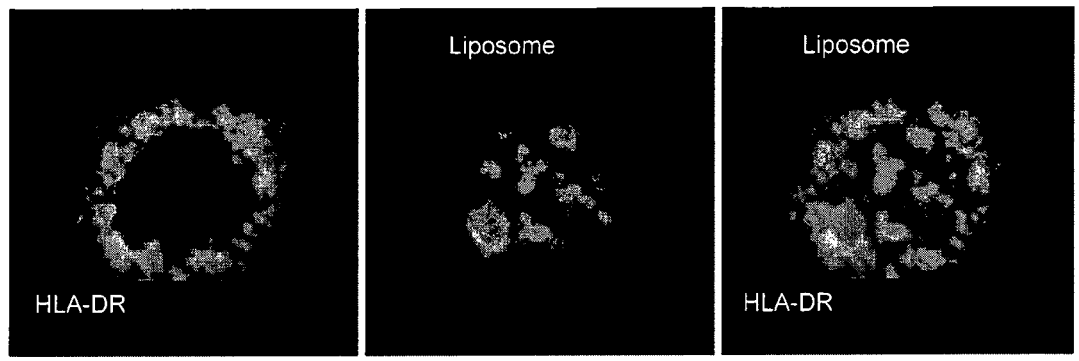
Figure 10:
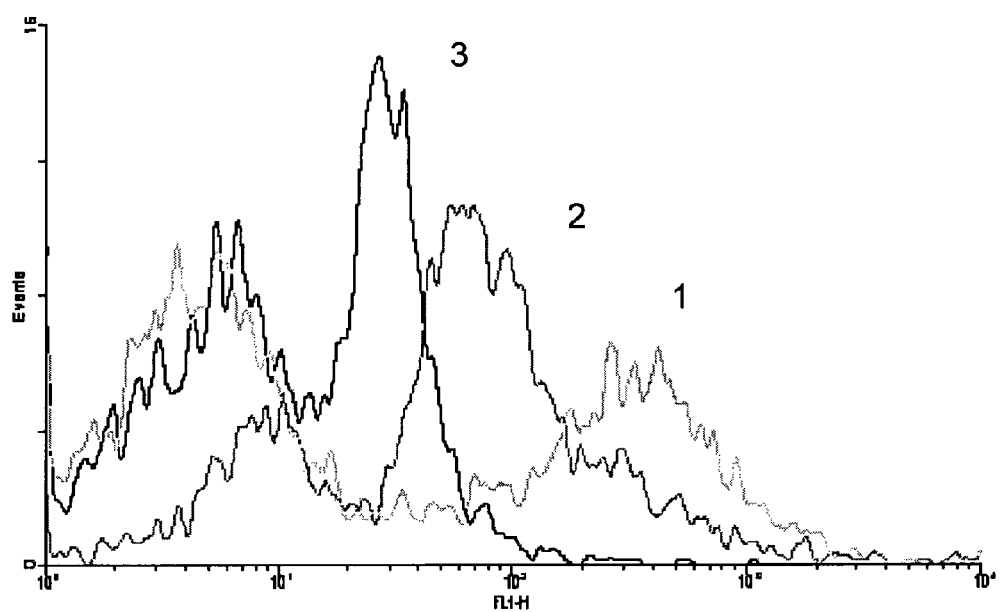
Figure 11:
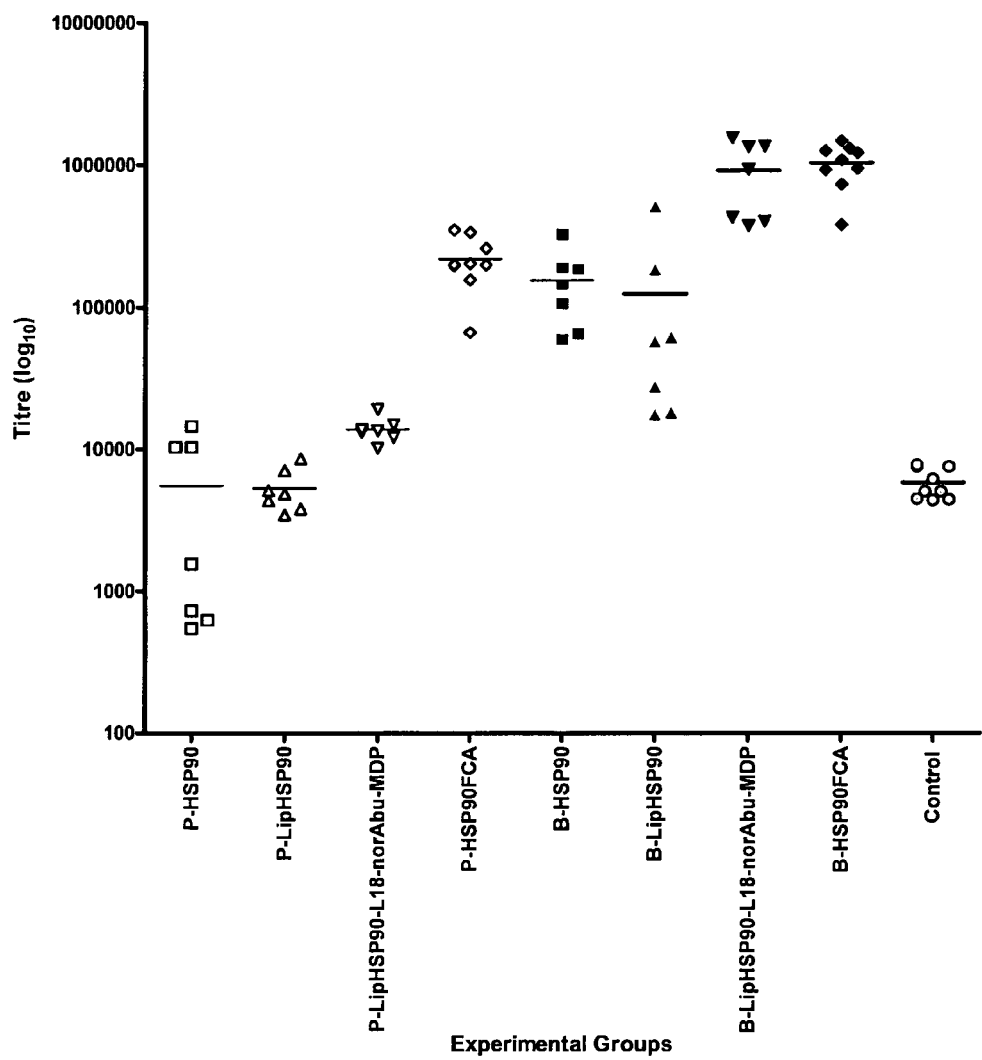
Figure 12:
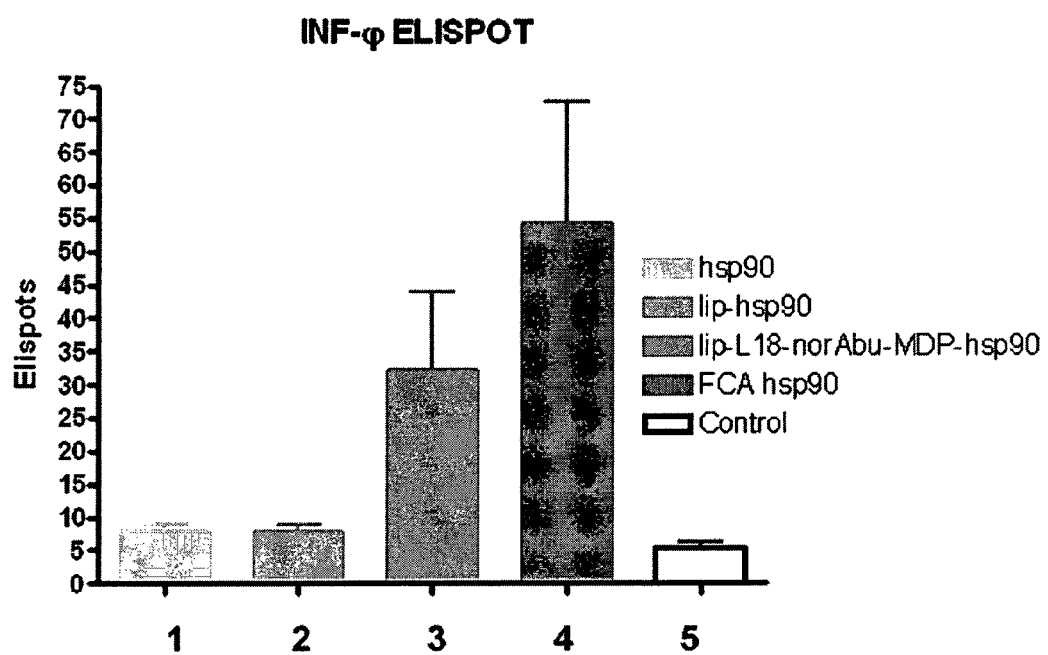
Figure 13:
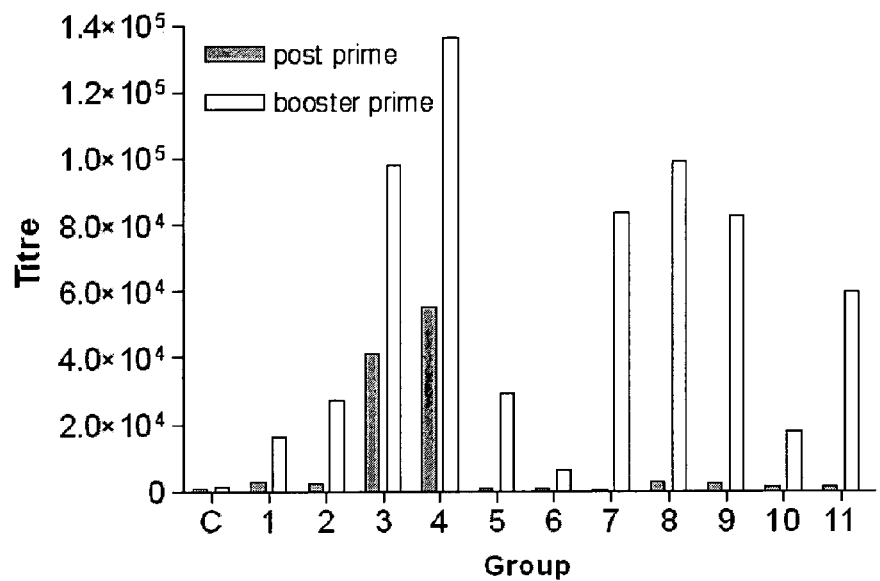
Figure 14:
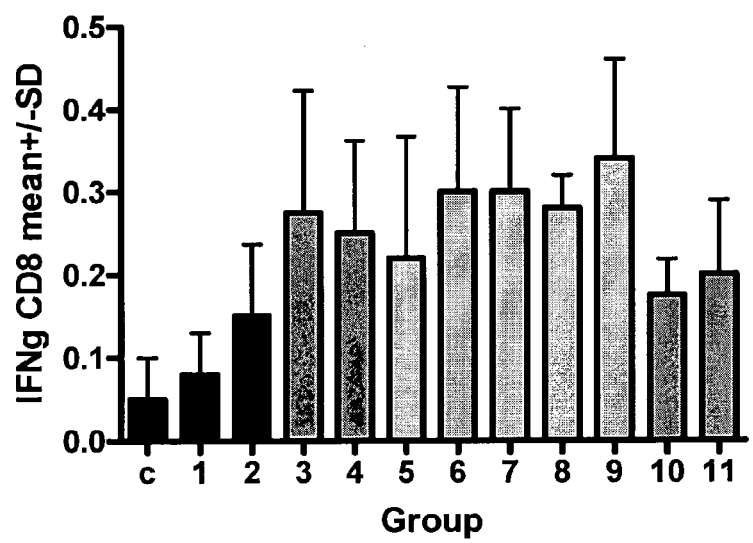
Figure 15:
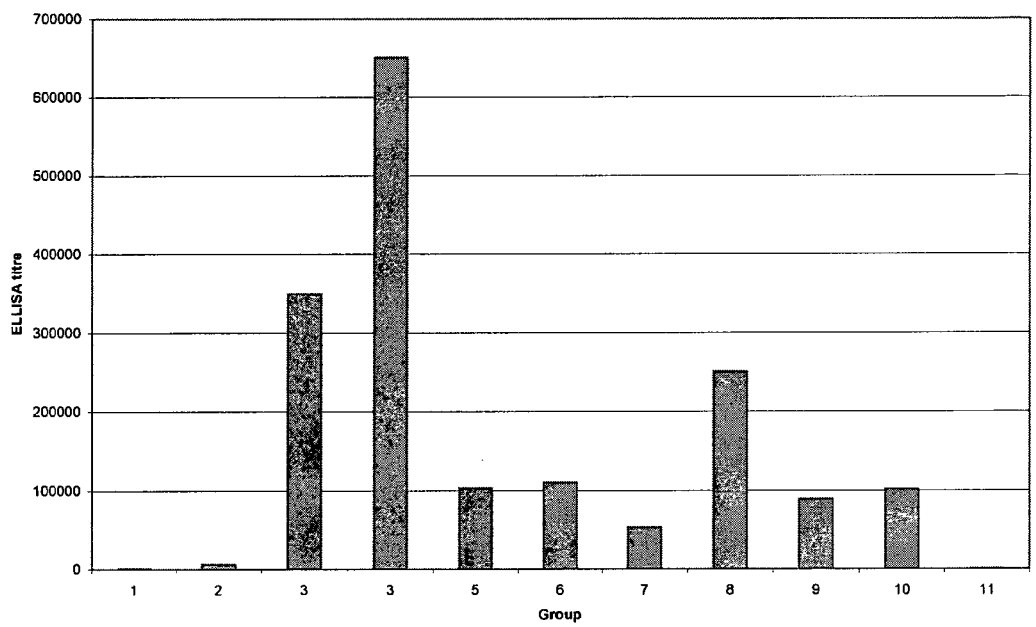
Figure 16:
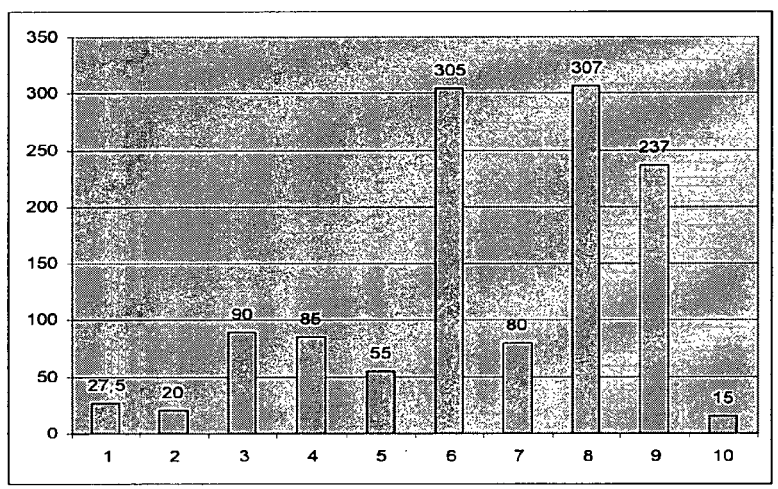
Figure 17:
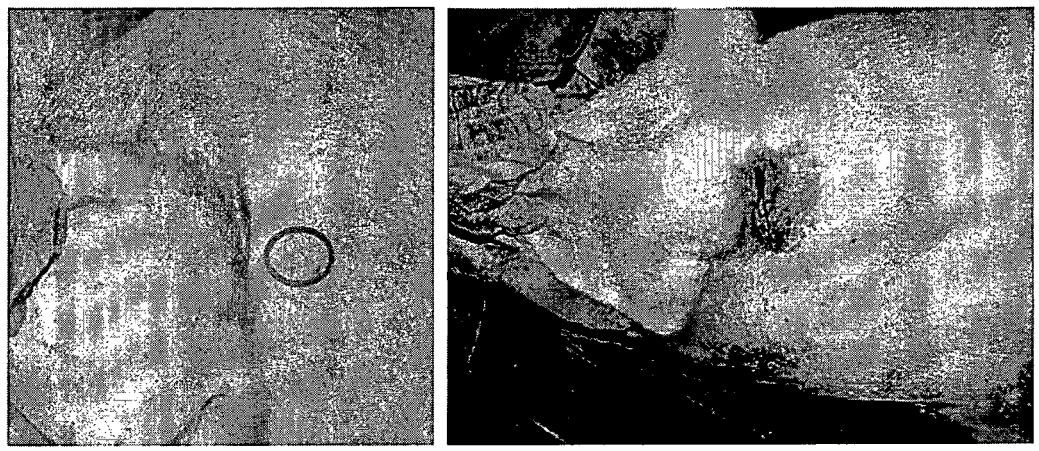
Figure 18:
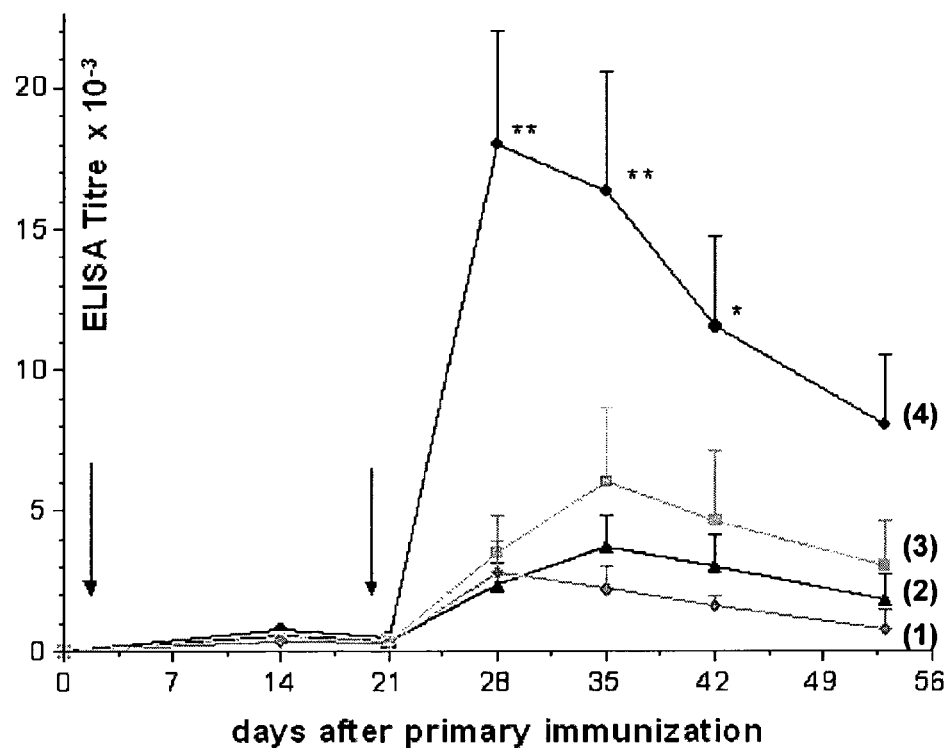
Figure 19:
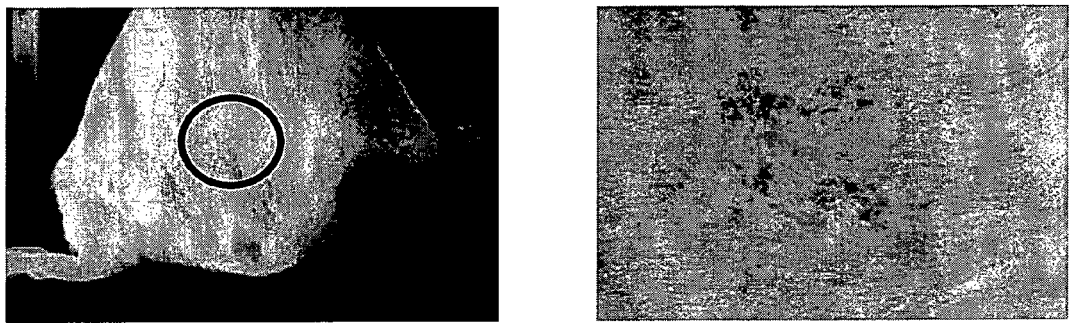
Figure 20:
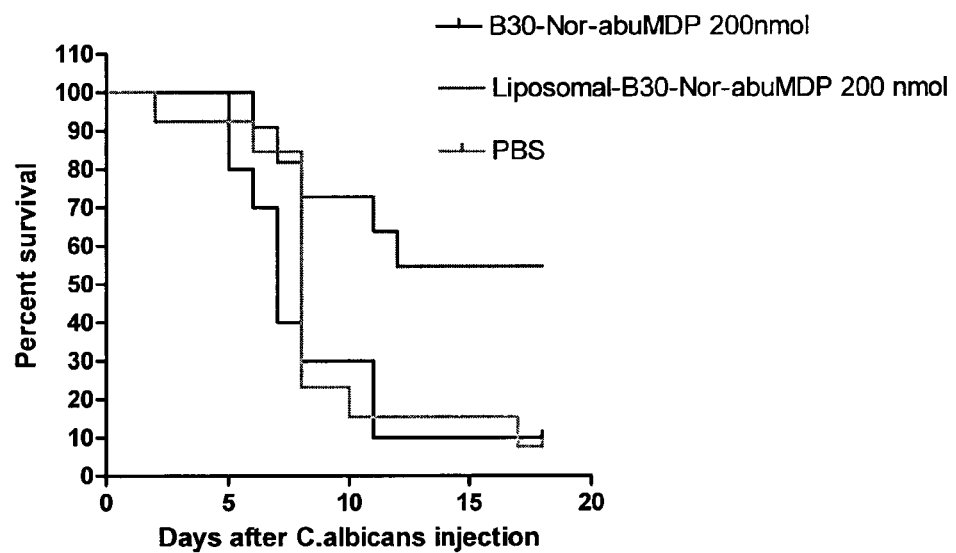
Figure 21:
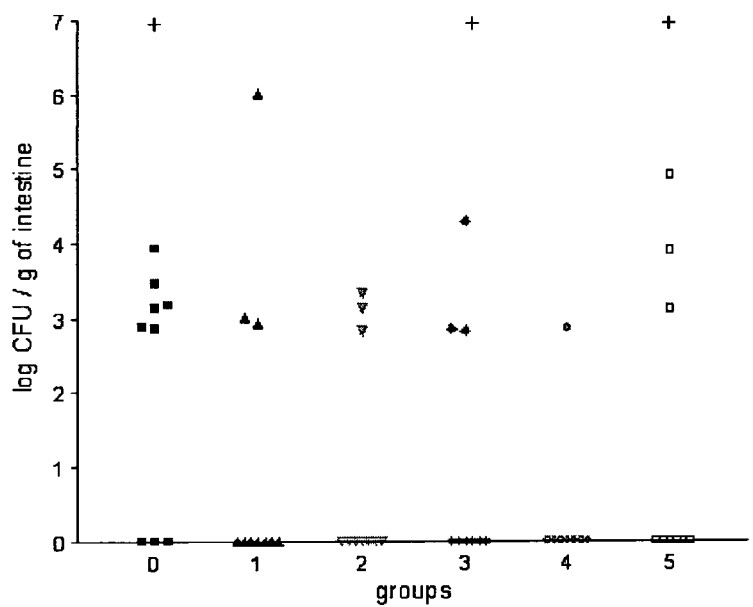
Figure 22:
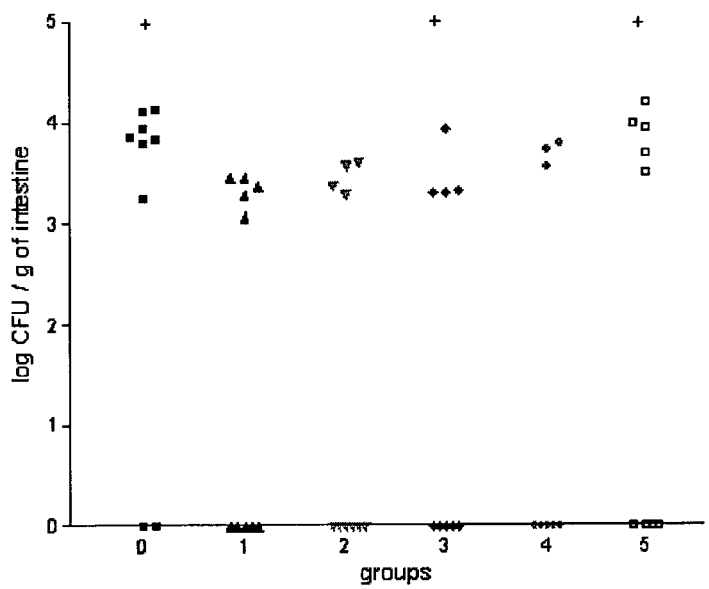
Figure 23:
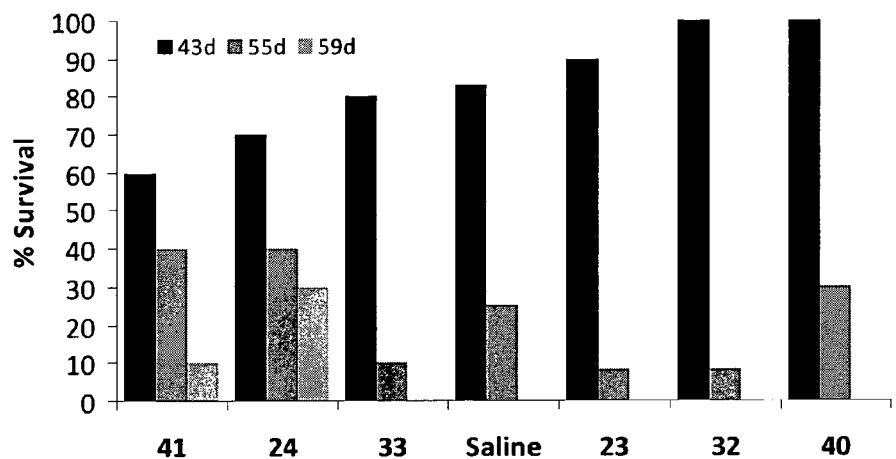
Figure 24:
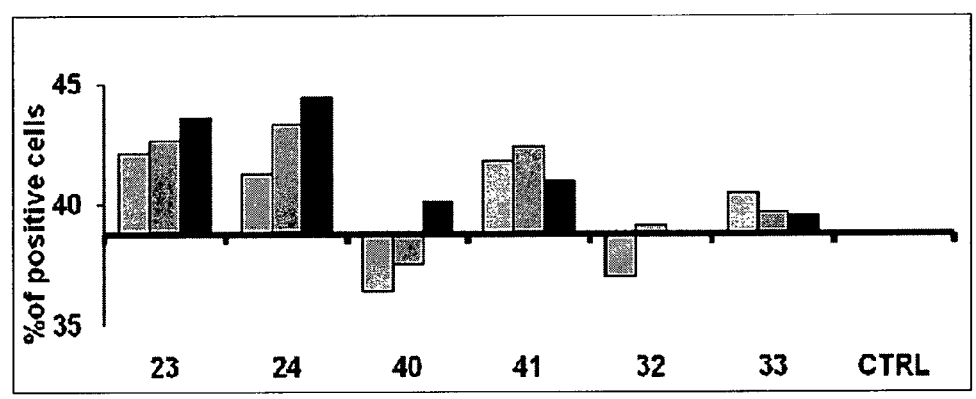
Figure 25:
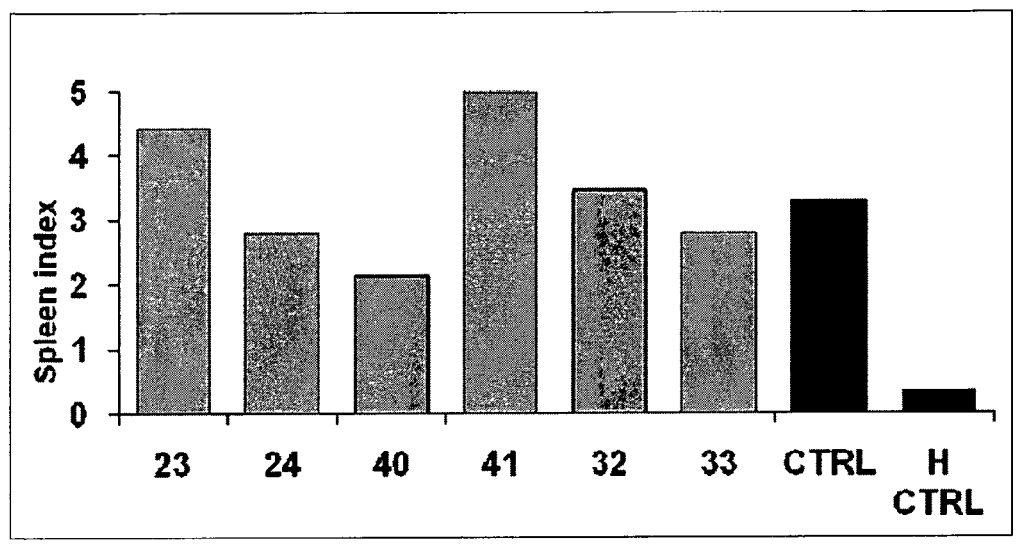
Figure 26:
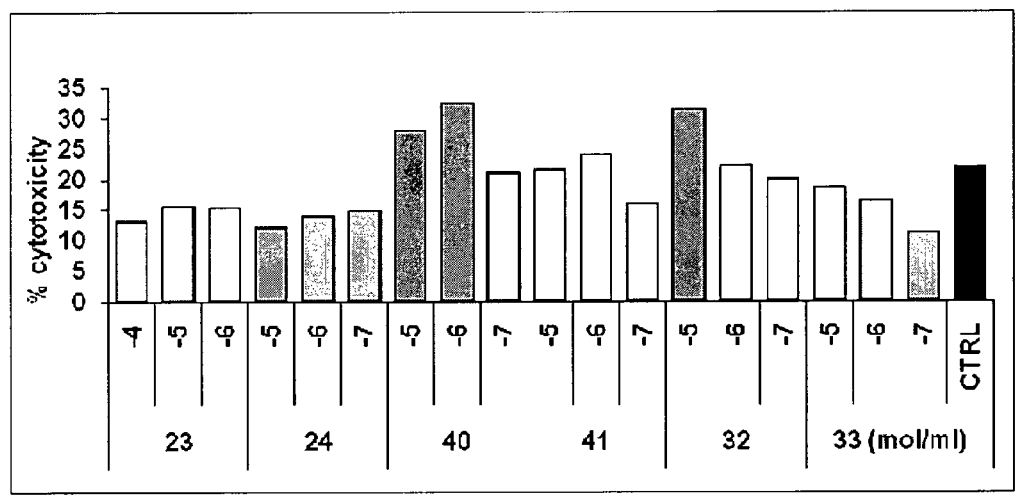
Figure 27:
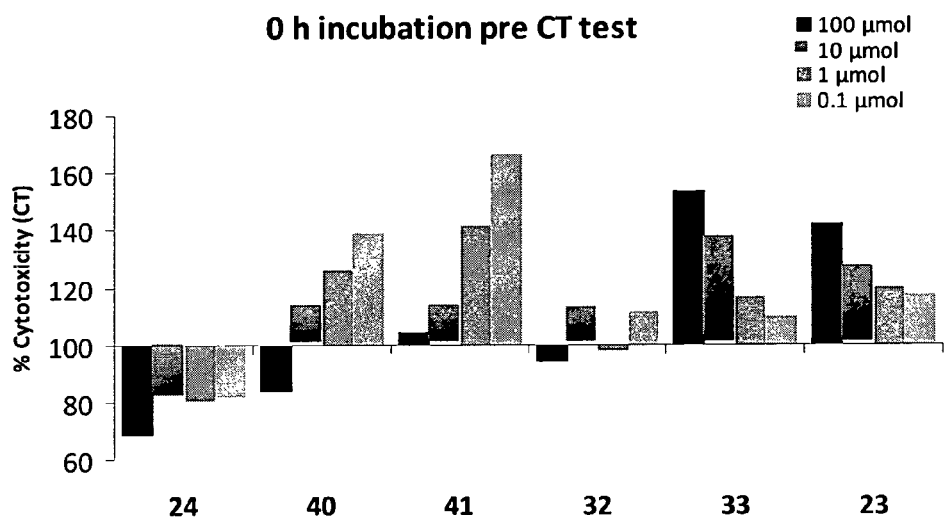
Figure 28:
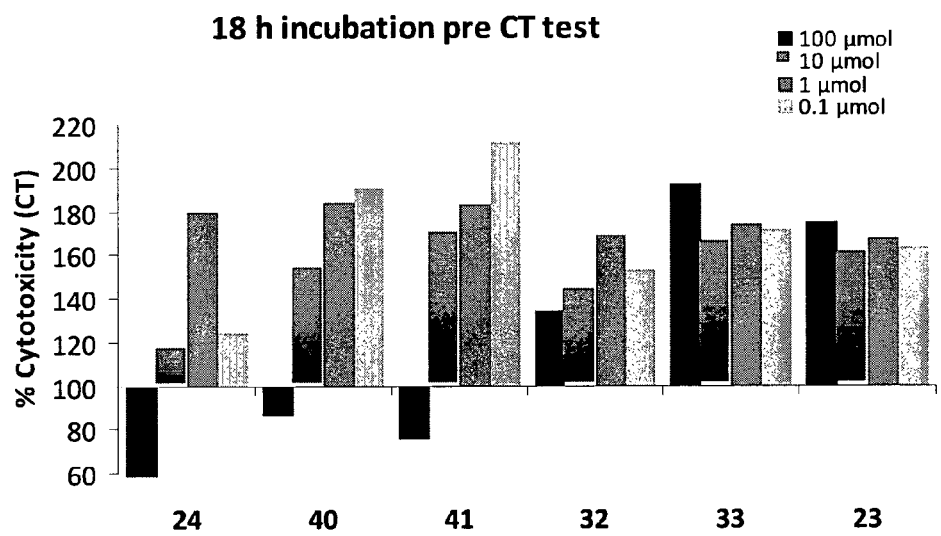
Figure 29:
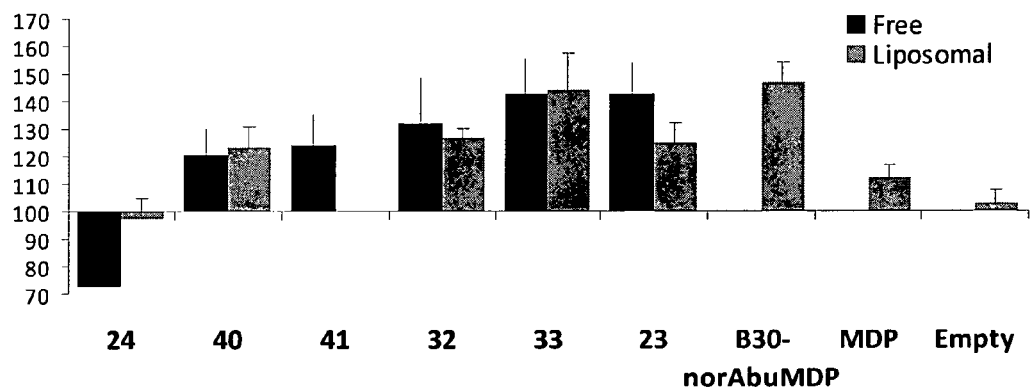
Figure 30:
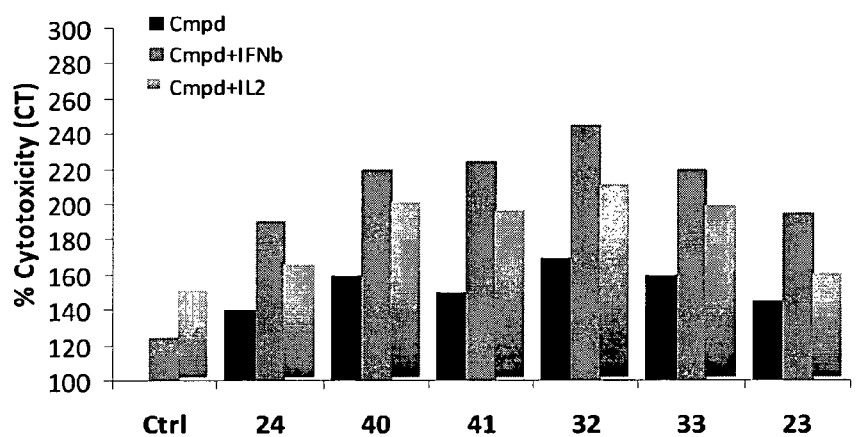
Figure 31:
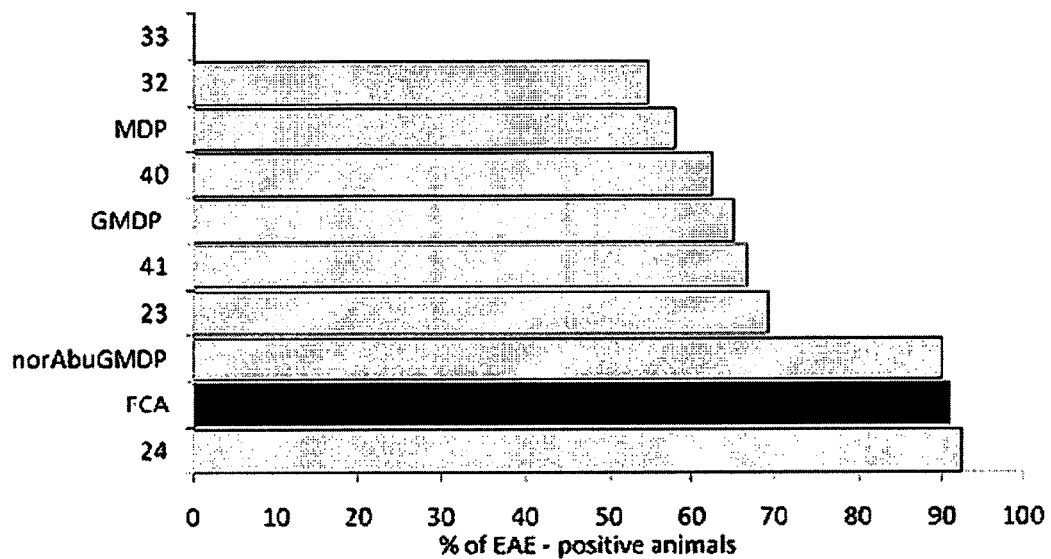
Figure 32:
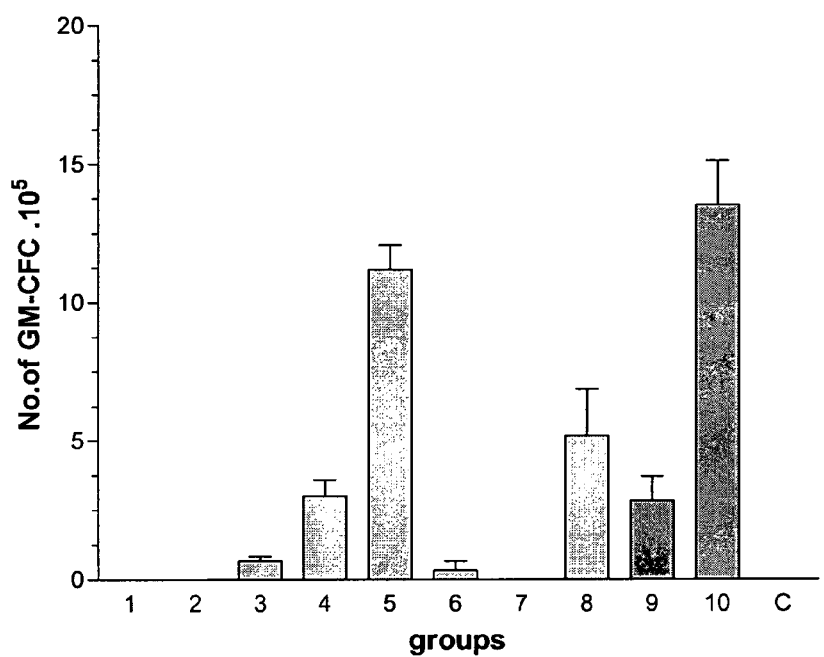
Figure 33:
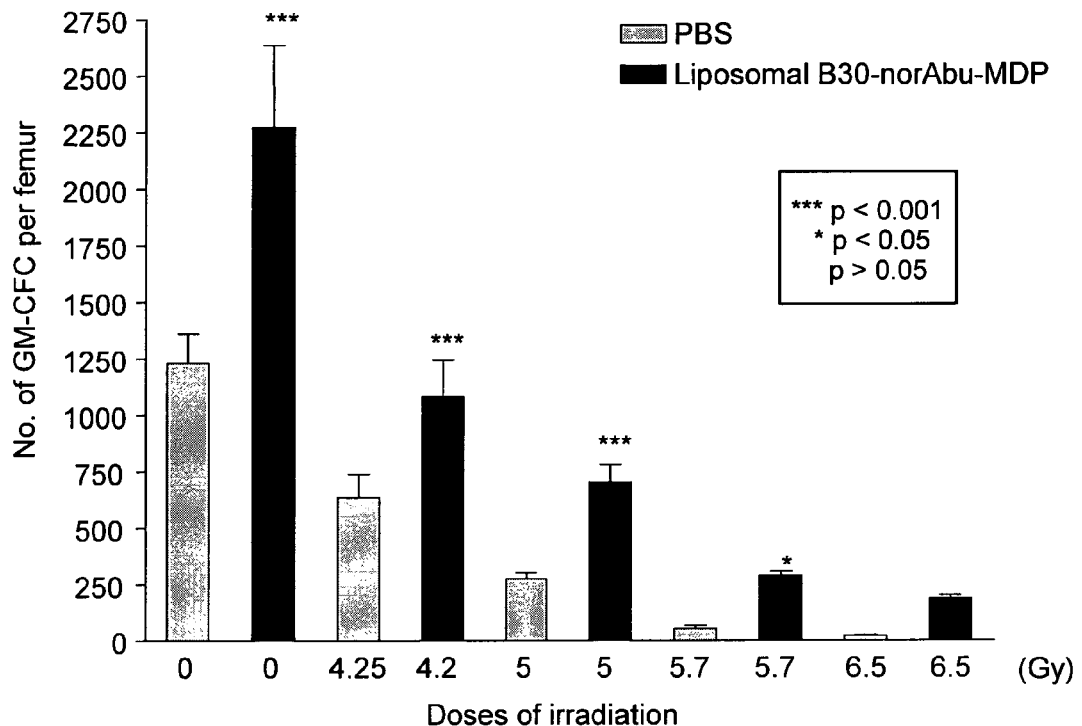
Figure 34:
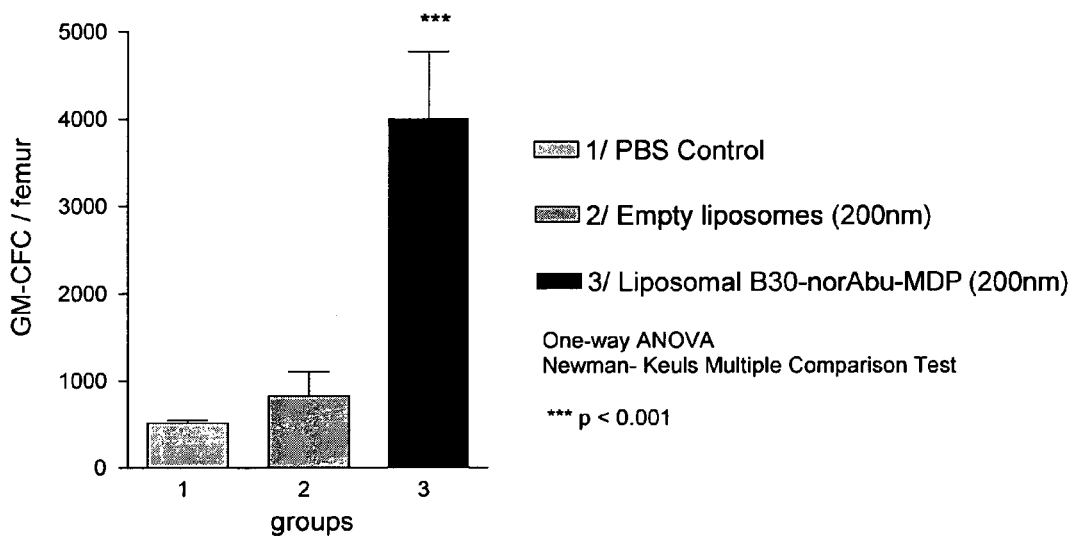
Figure 35:
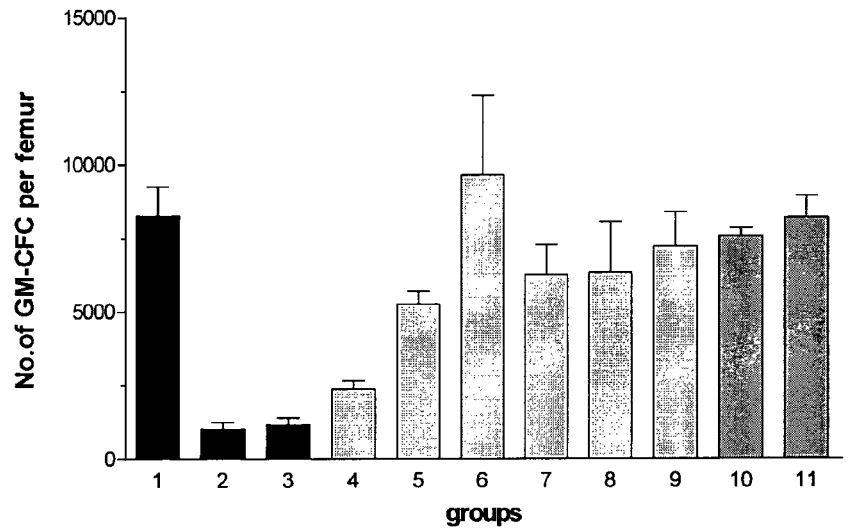
Figure 36:
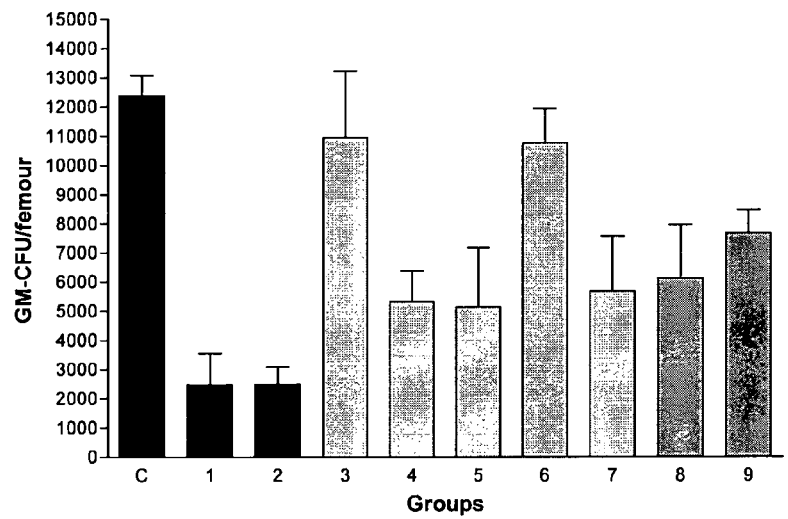
Figure 37:
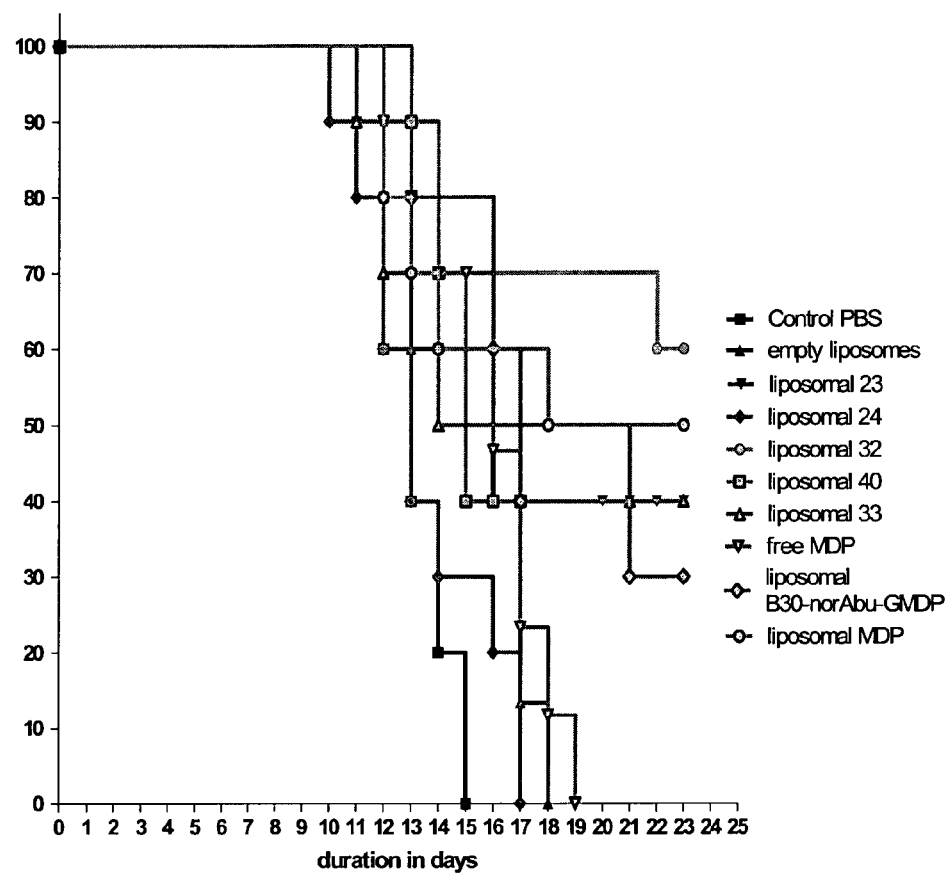

FIG. 9 shows Confocal fluorescence microscopy showing the intracellular localisation of proteoliposomes into dendritic cells (Staining with labeled antibodies specific for major histocompatibility complex, MHC class II, cell surface receptor (HLA-DR) allows dendritic cells to be identified (left). Rhodamine-labeled protoeliposomes can be tracked to follow incorporation into dendritic (middle). An overlay of both stainings is shown on the right);

FIG. 10 shows FACS Analysis showing the incorporation of proteoliposomes into dendritic cells (Empty liposomes (1), NorAbuM DP liposomes (2), control (3));

FIG. 11 shows Antibody Response for proteoliposome vaccine against *C. albicans* hsp90 (P—primary immunisation, B—booster);

FIG. 12 shows Cellular Response for proteoliposome vaccine against *C. albicans* hsp90;

FIG. 13 shows Antibody Responses for r-hsp90 proteoliposomes with muramyl glycopeptide derivatives (Columns: C—control non-immunised mice; 1—HSP 90; 2—liposomal Ni-HSP90; 3—AlOH+HSP90; 4—CFA+HSP 90; 5—liposomal 23+Ni-HSP90; 6—liposomal 24+Ni-HSP90; 7—liposomal 32+Ni-HSP90; 8—liposomal 40+Ni-HSP90; 9—liposomal 33+Ni-HSP90; 10—liposomal B30-norAbu-MDP+Ni-HSP90; 11—liposomal MDP+Ni-HSP90);

FIG. 14 shows Cellular Responses for r-hsp90 proteoliposomes with muramyl glycopeptide derivatives (Columns: C—control non-immunised mice; 1—HSP 90; 2—liposomalNi-HSP90; 3—AlOH +HSP90; 4—CFA+HSP 90; 5—liposomal 23+Ni-HSP90; 6—liposomal 24+Ni-HSP90; 7—liposomal 32+Ni-HSP90; 8—liposomal 40+Ni-HSP90; 9—liposomal 33+Ni-HSP90; 10—liposomal B30-norAbu-MDP+Ni-HSP90; 11—liposomal MDP+Ni-HSP90);

FIG. 15 shows Antibody Responses for OspC proteoliposomes with muramyl glycopeptide derivatives (1.—free antigen OspC, 2.—liposomal OspC, 3.—OspC+FCA, (Freund complet adjuvans), 4.—OspC+aluminium hydroxide (AlOH), 5.—OspC liposomal MDP, 6.—OspC liposomal 24, 7.—OspC liposomal 33, 8.—OspC liposomal 40, 9.—OspC liposomal 41, 10.—OspC liposomal 32, 11—Control serum (non-immunised mice);

FIG. 16 shows Cellular Responses for OspC proteoliposomes with muramyl glycopeptide derivatives (TH1 response—assayed by Interferon Gama (ELISpot) (1. Osp C; 2. Lip Osp C; 3. Osp C/Ni/lipB30-norAbu-M DP; 4. Osp C/Ni/lip lipB30-norAbu-M DP/(booster without lipB30-norAbu-MDP); 5. Osp C/Ni/lipMDP; 6. OspC FCA/FCA; OspC Alum/Alum; 8. OspC FCA/IFC; 9. OspC IFC/IFC; 10 Control);

FIG. 17 shows Skin reactions of proteoliposome based vaccine (left) versus oil-based control vaccine (right);

FIG. 18 shows TaT Antibody Response (TaT (1), TaT in liposomes (2), TaT+compound 23 (3), TaT+compound 23 in liposomes (4));

FIG. 19 shows Clearing of ringworm infection in therapeutic vaccine treated animal versus control (left—treated animal, right—control);

FIG. 20 shows Liposomal B30-norAbuMDP increases survival of *candida albicans* infection by a factor of 5;

FIG. 21 shows Reduction of salmonella titer (30 d post infection) in intestines by lip. B30-norAbu-M DP (Columns: 0—Control; 1—i.n. 50 µg/mouse; 2—i.n. 25 µg/mouse; 3—i.n. 5 µg/mouse; 4—p.o. 50 µg/mouse; 5—p.o. 10 µg/mouse; +death loss);

FIG. 22 shows Reduction of salmonella titer (30 d post infection) in spleen by lip. B30-norAbu-MDP (0—Control; 1—i.n. 50 µg/mouse; 2—i.n. 25 µg/mouse; 3—i.n. 5 µg/mouse; 4—p.o. 50 µg/mouse; 5—p.o. 10 µg/mouse; +death loss);

FIG. 23 shows Effect of Muramyl glycopeptide derivatives on survival in Friend leukemia virus infection;

FIG. 24 shows Effect of Muramyl glycopeptide derivatives on TER-119+ cell clonal expansion (day 16);

FIG. 25 shows Effect of Muramyl glycopeptide derivatives on reducing spleen weight (day 16);

FIG. 26 shows Effect of Muramyl glycopeptide derivatives on inducing NK activity in FLV-challenged mice (at the concentrations indicated);

FIG. 27 shows Effect of Muramyl glycopeptide derivatives on inducing NK activity in human PBMCs (no pre-incubation);

FIG. 28 shows Effect of Muramyl glycopeptide derivatives on inducing NK activity in human PBMCs (18h pre-incubation);

FIG. 29 shows Effect of Muramyl glycopeptide derivatives on inducing NK activity in human PBMCs (comparison of 'free' with liposomal formulations);

FIG. 30 shows Effect of Muramyl glycopeptide derivatives on inducing NK activity in human PBMCs in the presence of IFN-β and IL-2;

FIG. 31 shows Effect of Muramyl glycopeptide derivatives on stimulating Th1 cytotoxicity in guinea pig (EAE);

FIG. 32 shows Effect of Muramyl glycopeptide derivatives on enhancing GM-CFC stimulating activity (CSA) in serum (mouse) (1—Solution for infusion; 2—Empty liposomes; 3—liposomal 23; 4—liposomal 24; 5—liposomal 32; 6—liposomal 40; 7—liposomal 33; 8—liposomal 41; 9—liposomal B30-norAbu-MDP; 10—liposomal MDP; C—control without serum);

FIG. 33 shows GM-CFC induction by muramyl glycopeptide derivatives in mice irradiated by various doses of γ radiation;

FIG. 34 shows GM-CFC induction by liposomal B30-norAbu-M DP versus empty liposome and PBS in mice irradiated by 6 Gy;

FIG. 35 shows GM-CFC induction by muramyl glycopeptide derivatives, administered pre exposure to 6 Gy (Columns: 1—Nonirradiated Control; 2—Irradiated Control PBS; 3—Empty liposomes; 4—liposomal 23; 5—liposomal 24; 6—liposomal 32; 7—liposomal 40; 8—liposomal 33; 9—liposomal 41; 10—liposomal B30-norAbu-MDP; 11—liposomal MDP);

FIG. 36 shows GM-CFC induction by muramyl glycopeptide derivatives, administered post exposure to 6 Gy (Columns: C—Nonirradiated Control; 1—Irradiated Control PBS; 2—Empty liposomes; 3—liposomal 23; 4—liposomal 24; 5—liposomal 32; 6—liposomal 40; 7—liposomal 33; 8—liposomal B30-norAbu-M DP; 9—liposomal MDP);

FIG. 37 shows Survival curves of lethally irradiated mice treated by muramyl glycopeptide derivatives 24h before exposure to 10 Gy.

Figure 1:
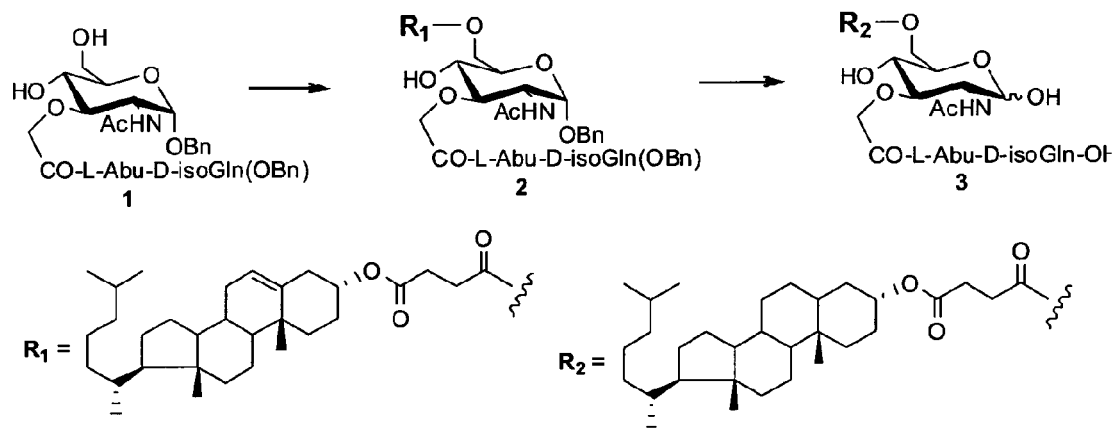
FIG. 1 shows the preparation of normuramylglycopeptide analogues modified by an acyl substituent on the primary hydroxyl group in the saccharide part of a molecule of general formula I.

Referring to FIG. 1, compound 1 is protected at the anomeric centre of the sugar part and at the carboxyterminus of the peptide part with benzyl protecting groups as previously described[23,24]. The acyl substituent was introduced into primary hydroxyl (6) group 1 with high regioselectivity by the reaction of 1 with an appropriate lipid carboxylic acid compound. The reaction was promoted with N-(3-dinnethylaminopropyl)-N'-ethylcarbodiimide hydrochloride (WSC) in the presence of 4-dimethylaminopyridine (DMAP) in N,N-dimethylformamide (DMF) to give compound 2.

The advantage of this procedure is the possibility to effectively modulate the regioselectivity of O-acylation by changes of reaction temperature, independent of the effects of steric hindrance and electronic effects on the reactivity of the carboxylic acid. Removal of the benzyl protecting groups in 2 by hydrogenolysis on Pd—C catalyst in acetic acid[23,24] or in the case of substrates having double C=C bond sensitive to the hydrogenation process (e.g. analogues carrying a cholesterol residue) by $Pd(OH)_2$—C catalyzed reaction with cyclohexene, afforded the target 6-O-acyl derivative 3.

To date, the standard approach to prepare the saccharide part of normuramyl glycopeptides has taken three steps. Starting with a D-glucosamine unit protected on OH (3) with an allyl group, the allyl group is first isomerized to a propenyl one, this is subjected to acid catalyzed splitting and, finally, a glycolyl ether residue is introduced[25,28,29].

Figure 2:
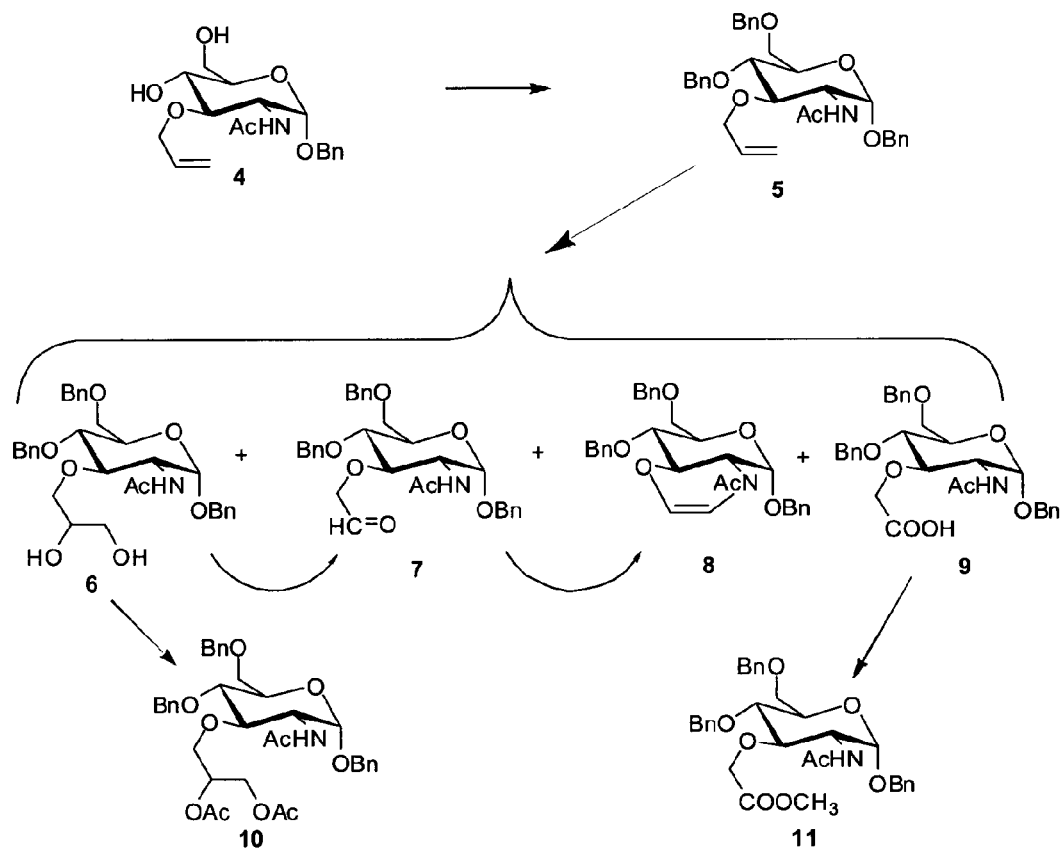
FIGS. 2 and 3 show a synthetic route to the saccharide part of normuramyl glycopeptides involving an oxidative splitting of an O-allyl protecting group.
Figure 3:
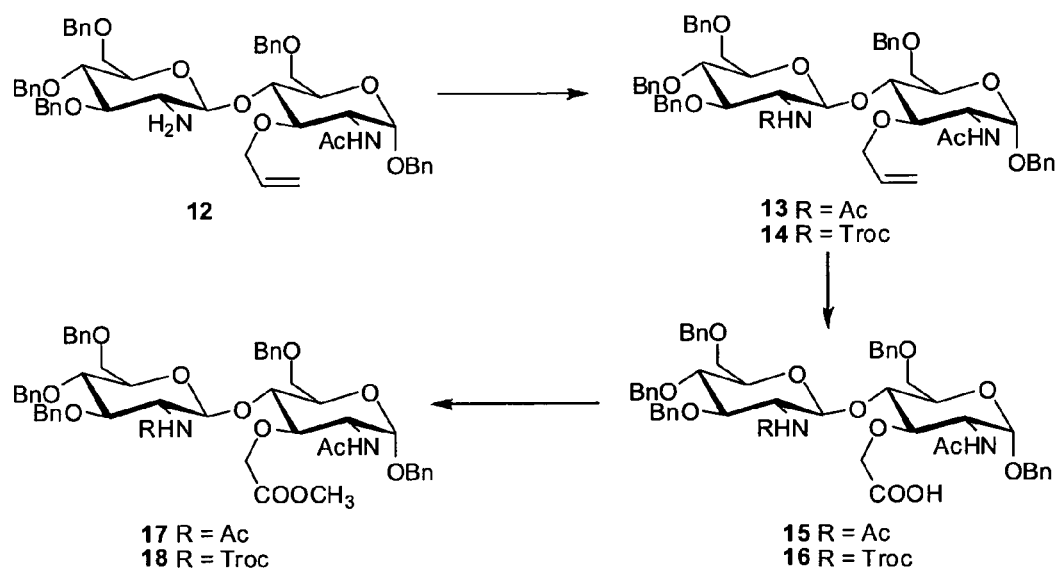

In order to simplify the synthesis of the target normuramyl glycopeptides a one-step conversion of a glucosamine unit protected on OH (3) with allyl group into normuramyl unit was developed (FIGS. 2 and 3).

The approach is based on the selective oxidative splitting of C=C bond of 3-O-allyl protecting group of the saccharide synthons 5, 13 and 14. These compounds have O-benzyl protecting groups on the other OH groups. The compounds are split into a glycolylether residue by the action of $RuO_4$, which was generated in situ from catalytic amount of $RuCl_3$ with $NaIO_4$ under controlled conditions. The reaction conditions were elaborated for the synthesis of fully O-benzyl protected normuramic acid 9 from the allyl derivative 5 (see FIG. 2). Under similar conditions, the described[37] oxidation of O-benzyl protecting groups to benzoates was not observed, but as a side reaction, the formation of cyclic compound 8 took place. The distribution of products of this reaction, i.e., diol 6 and aldehyde 7 intermediates, the cyclic product 8 and the required normuramic acid 9, and products whose origin can be linked with the above-mentioned oxidation of O-benzyl protecting groups, can be effectively modulated by the choice of reaction conditions. The tendency of the intermediate aldehyde 7 to condense with the vicinal acetamido group, to give cyclic compound 8, was confirmed. The formation of undesirable cyclic compound 8 was successfully eliminated and the target normuramic acid 9 was obtained in good yield by carrying out this oxidation at decreased temperature using an excess of $NaIO_4$ for the oxidative splitting of C=C bond to carboxyl function. The starting compound 5 was obtained by the benzylation of the allyl derivative 4[25] with benzyl bromide and sodium hydride in DMF. The diol 6 was fully characterized after its conversion to the diacetate 10.

The above procedure was successfully applied for the preparation of glucosaminylnormuramic acid synthons 15 and 16 (see FIG. 3) from allyl derivatives 13 and 14, respectively. The obtained acids 9, 15 and 16 were converted by reaction with diazomethane to their methyl esters 11, 17 and 18, respectively, and fully characterized.

The amine 12 and allyl derivative 13 are readily accessible using the described procedure[29]. The troc derivative 14 (i.e. with a trichloroethoxycarbonyl protecting group on the amine) was prepared by reaction of amine 12 with trichloroethoxycarbonyl chloride in pyridine.

Figure 4:
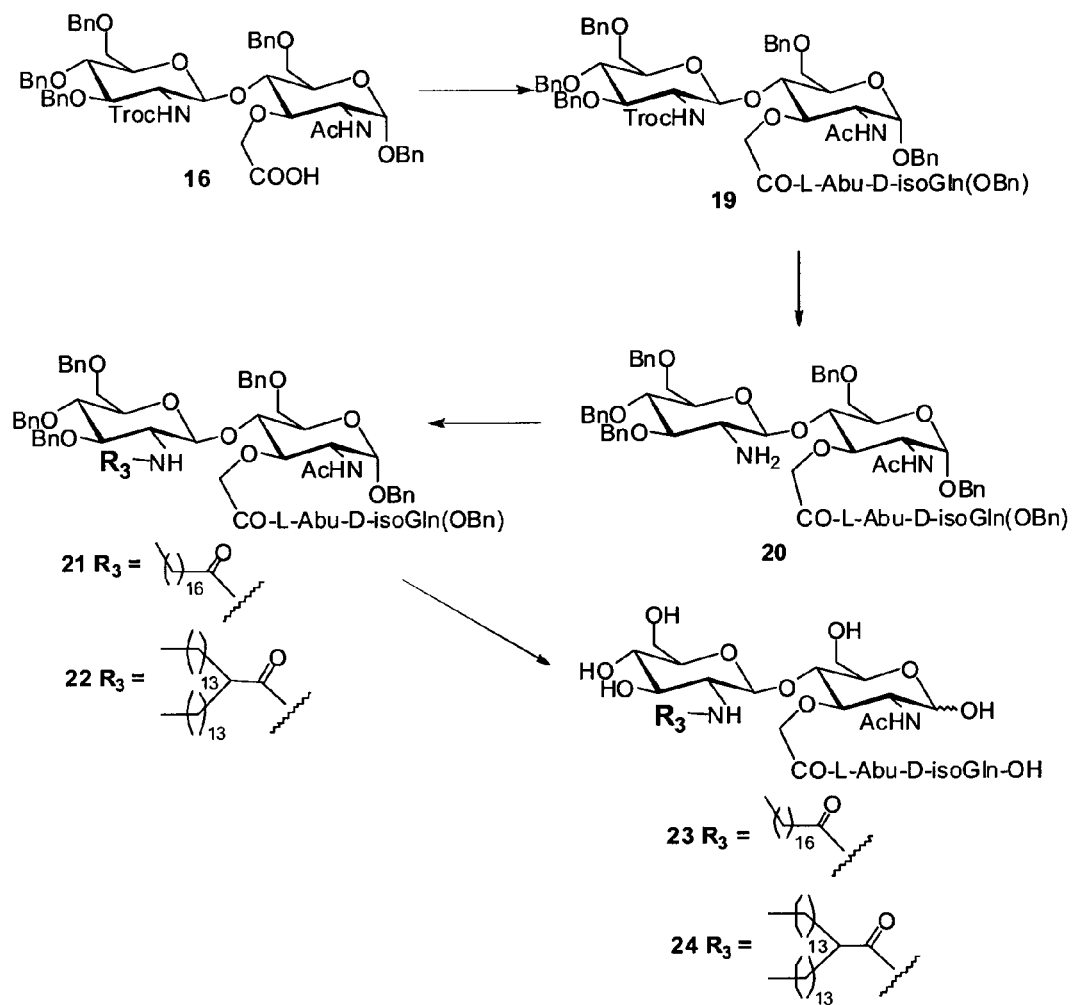
FIG. 4 shows the synthetic route to norm uramyl glycopeptides 23 & 24.

The synthesis of glucosaminyl-normuramylglycopeptide analogues modified by an acyl substituent on the amino group of a glucosamine subunit of the saccharide part of the molecule of general formula II is shown in FIG. 4. The synthesis is based on the preparation of a glucosaminyl-normuramylglycopeptide synthon 20 suitable for regioselective N-acylation of amino group of its glucosamine subunits. The protecting groups of this synthon meet the criteria of orthogonality, i.e., they may be removed independently of the other groups and functionalities present in the molecule.

N-acylation of the synthon 20 with an activated form of an appropriate lipophilic carboxylic acids followed by subsequent one-step deprotection gave the desired lipophilic normuramyl glycopeptide. This approach enables the preparation of a series of glucosaminyl-normuramylglycopeptide analogues modified on amino group of glucosamine subunit by various bulky lipophilic acyl residues from one synthon in two steps. The previously described synthetic schemes[28,29] used to prepared N-L18-norAbu-GMDP required a separate synthetic route for every new analogue.

The synthon 20 was prepared in two steps from the disaccharide 16. First, condensation of 16 with L-2-aminobutanoyl-D-isoglutamine benzyl ester[25], promoted by DCC (1,3-dicyclohexylcarbodiimide) in presence of HOBT (1-hydroxy-benzotriazole), produced the protected glycopeptide 19. Then, removal of the Troc protecting group with zinc in acetic acid gave the desired glucosaminylnormuramylglycopeptide synthon 20.

N-acylation of synthon 20 with acylchloride derived from appropriate bulky fatty acid in the presence of DMAP and diisopropylethylamine (DIEA) in DMF gave compounds 21 & 22. Hydrogenolysis of the benzyl groups of compound 4 gave the target N-Acyl-norAbu-GMDP derivatives 23 & 24.

Figure 5:
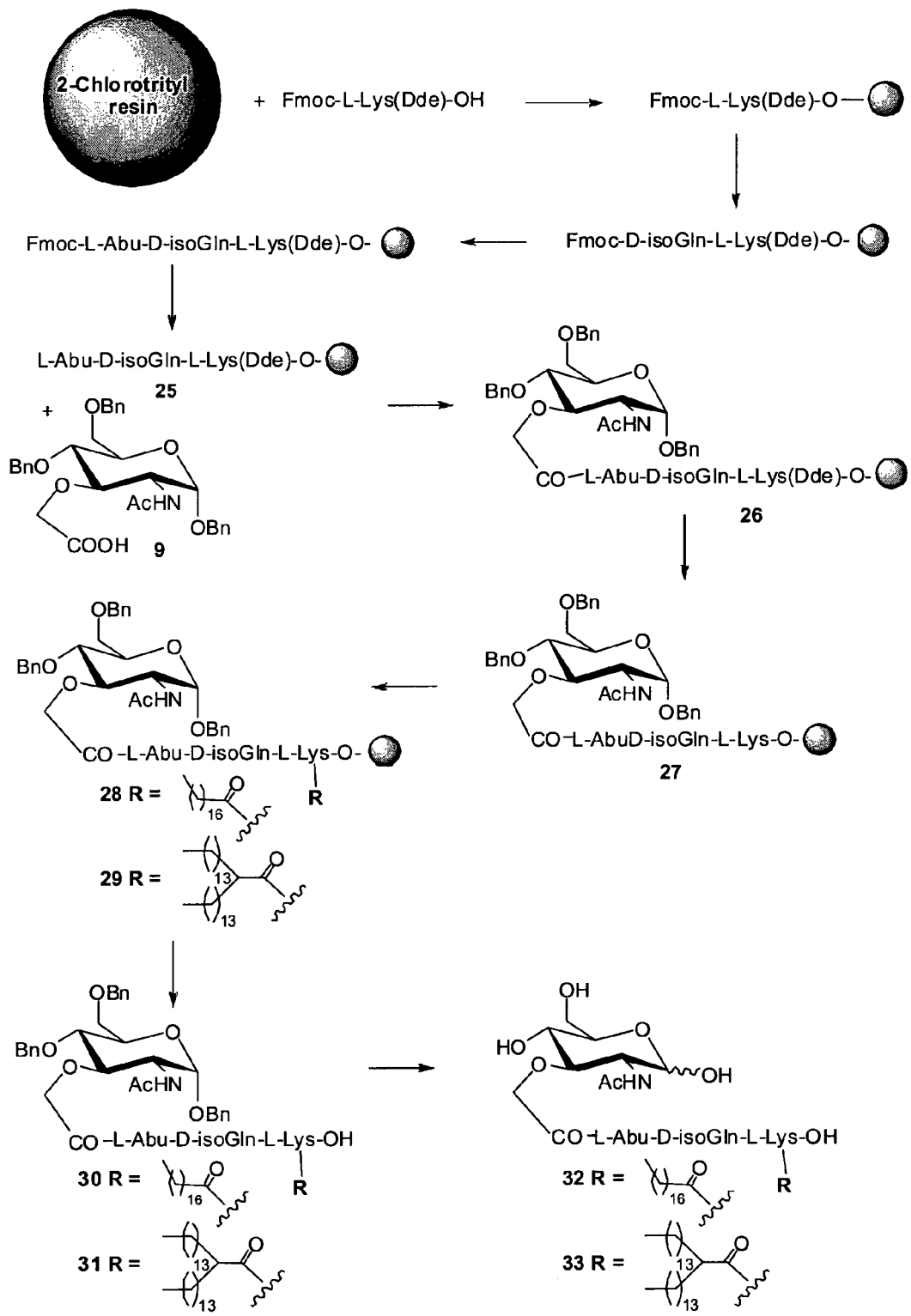
FIGS. 5 and 6 show the solid phase synthesis of normuramyl glycopeptides modified on the carboxyterminus of the peptide part of their molecules by acyl substituents.
Figure 6:
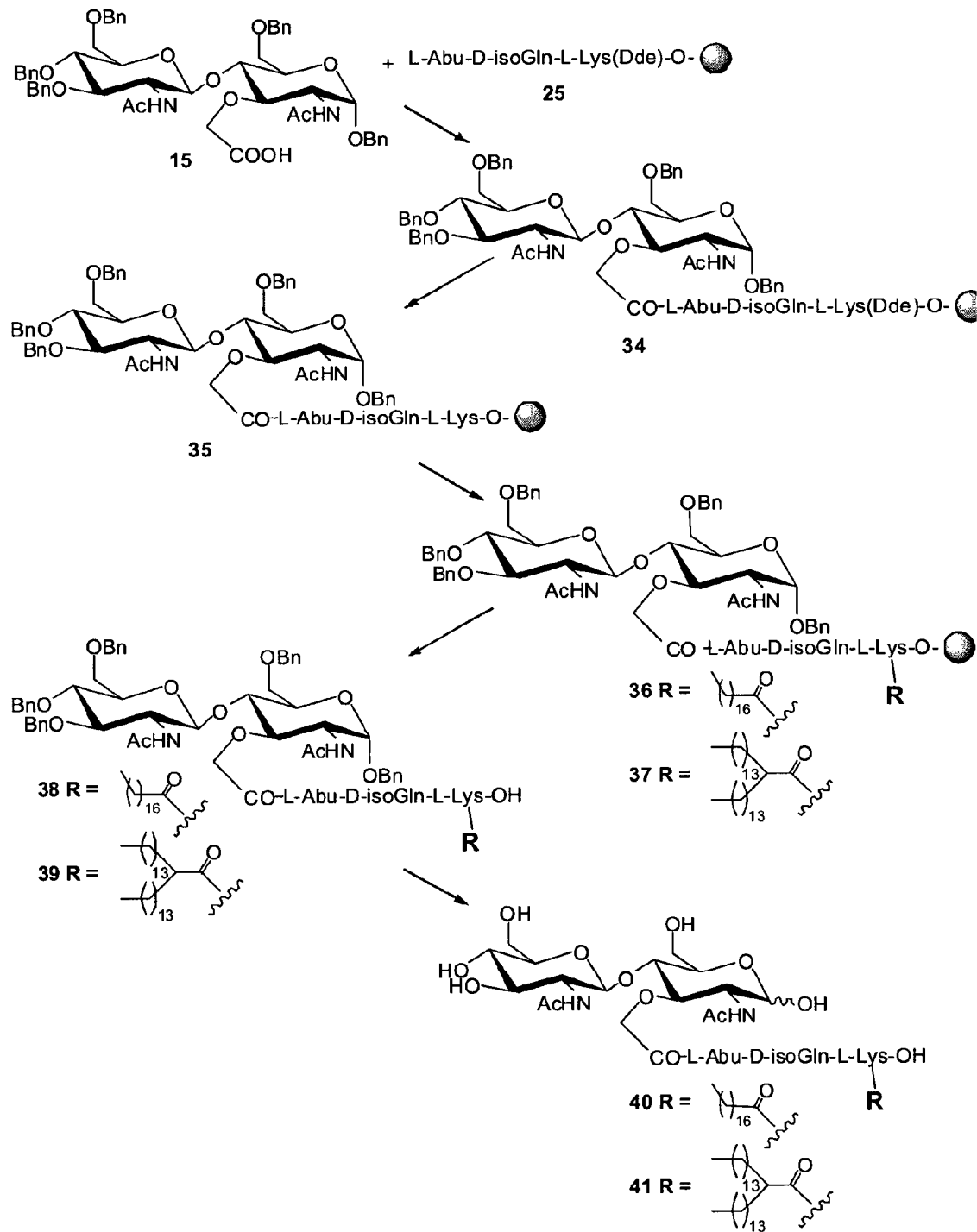

A new reaction scheme employing solid phase synthesis was developed in order to provide a rational approach to the preparation of normuramyl glycopeptides of Formula I and II that are modified on carboxy terminus of the peptide part of the molecule by acyl substituents (see FIGS. 5 and 6). The acyl substituents are attached to the carboxy terminus via a side chain of lysine.

The reaction scheme requires that (a) a glycopeptide chain (i.e. including the saccharide unit) can be built up on a solid phase carrier; (b) an acyl substituent can be introduced; (c) a protected product can be removed from the carrier under conditions which can be tolerated by the relatively unstable saccharide part of the product.

Barlos's 2-chlorotrityl resin was chosen as a suitable solid phase carrier because it enables the protected product to be removed from the carrier by acetic acid. The peptide chain was built up using different protecting groups for the α-amino group participating in the elongation of the glycopeptide chain and the ω-amino group in the side chain. The α-amino group was protected with a Fmoc group (Fmoc=9-fluorenylmethyl-oxycarbonyl), which can be removed using a 20% piperidine solution. The side chain ω-amino group was protected with Dde group [Dde=1-(4,4-dimethyl-2,6-dioxocyclohexyliden)-ethyl] which is stable to 20% piperidine, but which is removed by a 2% hydrazine solution. Thus, the peptide chain was built up using a 20% piperidine solution to remove the Fmoc group from the α-amino group followed by a HBTU (O-Benzotriazol-1-yl-N,N,N'N'-Tetramethyluronium hexafluorophosphate) promoted coupling with an Fmoc protected amino acid. Once the desired peptide chain was formed, a 20% piperidine solution was used to provide a free α-amino group (see 25, FIG. 5) which could then be reacted with a saccharide unit 9 to form 26. Reaction with a 2% hydrazine solution removes the Ddde group to provide a carrier linked glycopeptide synthon 27, with a free ω-amino group, tailor made for regioselective introduction of an acyl substituent. Synthon 27 undergoes HBTU promoted N-acylation with an appropriate lipophilic carboxylic acids followed by cleavage of the product from the resin and one-step deprotection of the obtained lipoglycopeptide 30 & 31 (hydrogenolysis of benzyl protecting groups) afforded the desired normuramyl glycopeptides 32 & 33 modified on carboxyterminus of the peptide part by bulky lipophilic acyl residue.

The present invention will now be described in further detail in the following Examples, which are not to be construed as being limiting. Preferred features and characteristics of one aspect of the invention are applicable to another aspect *mutatis mutandis*.

EXAMPLES

Example 1

Preparation of ChS-norAbuMDP

N-[2-O-(Benzyl 2-acetamido-2,3-dideoxy-6-O-{4-[(3α,8ξ,9ξ,14ξ)-cholest-5-en-3-yloxy]-4-oxobutanoyl}-D-glucopyranosid-3-yl)-glycoloyl]-L-2-aminobutanoyl-D-isoglutamine benzyl ester (2)

To a stirred solution of N-[2-O-(benzyl 2-acetamido-2,3-dideoxy-α-D-glucopyranosid-3-yl)-glycoloyl]-L-α-aminobutanoyl-D-isoglutamine benzyl ester[23,24] (1; 673 mg, 1 mmol) and cholesteryl hemisuccinate (5-cholesten-3β-ol 3-hemisuccinate; 584 mg, 1.2 mmol) in dry N,N-dimethylformamide (40 ml) WSC (383 mg, 2 mmol) and DMAP (269 mg, 2.2 mmol) were added and the mixture was stirred at temperature of ice bath for 8 h. The reaction course was checked by TLC in chloroform-methanol (10:1). Then, methanol (2 ml) was added, the mixture was stirred at room temperature for 4 h and the solvents were distilled off in vacuo. The residue was dissolved in chloroform (200 ml) and the solution was washed with 5% aqueous solution of sodium hydrogen sulfate (2×30 ml), saturated aqueous solution sodium hydrogen carbonate (2×30 ml) and 5% aqueous solution of sodium chloride (2×30 ml), dried over anhydrous magnesium sulfate and evaporated in vacuo. Chromatography of the residue on silica gel column in chloroform—methanol (15:1) followed by lyophilization of homogenous fractions from acetic acid afforded 833 mg (73%) of compound 2; $[\alpha]_D$ +10° (c 0.2, chloroform). $^1$H NMR spectrum: 7.39-7.31 m, 10H (H-arom.); 7.39-7.31 m, 3H (H-14'-H-16'); 5.13 d, 1H, J=12.2 (OCH$_2$Ph); 5.35 dq, 1H, J=1.8, 1.8, 5.4 (H-6"); 5.10 d, 1H, J=12.2 (OCH$_2$Ph); 4.85 d, 1H, J=3.8 (H-1); 4.70 d, 1H, J=11.6 (CH$_2$-Ph); 4.63-4.57 m (H-3'''); 4.47 d, 1H, J=11.6 (CH$_2$-Ph); 4.44 dd, 2H, J=4.1, 12.2 (H-6); 4.42 dt, 1H, J=5.0, 8.6, 8.6 (α-iGln); 4.29 ddd, 1H, J=3.8, 8.1, 10.3 (H-2); 4.29 dd, 1H, J=2.2, 12.2 (H-6); 4.28 dt, 1H, J=7.2, 8.7, 8.7 (α-Abu); 4.24 d, 1H, J=16.1 (OCH$_2$CO); 4.18 d, 1H, J=16.1 (OCH$_2$CO); 3.83 ddd, 1H, J=2.2, 4.1, 10.2 (H-5); 3.65 ddd, 1H, J=5.8, 9.0, 10.2 (H-2); 3.52 dd, 1H, J=9.0, 10.3 (H-3); 2.75-2.56 m, 4H (H-2"-H-3"); 2.52 ddd, 1H, J=6.7, 7.8, 17.2 (γ-iGln); 2.42 dt, 1H, J=6.7, 6.7, 17.2 (γ-iGln); 2.14-2.07 m, 1H (β-iGln); 2.02-1.92 m, 1H (β-iGln); 1.71-1.67 m, 1H (β-Abu); 1.58-1.52 m, 1H (β-iGln); 1.01 s, 3H (H-19'''); 0.93 t, 3H, J=7.4 (γ-Abu); 0.91 d, 3H, J=6.6 (H-21'''); 0.87 d, 3H, J=6.6 (H-27'''); 0.86 d, 3H, J=6.6 (H-26'''); 0.67 s, 3H (H-18'''). $^{13}$C NMR spectrum: 173.69 s (CONH$_2$); 173.42 s (C-4"); 172.99 s (CH$_2$OCO); 172.38 s (COOCH$_2$C$_6$H$_5$); 171.93 s (Abu-CO); 171.55 s (OCH$_2$CO); 170.20 s (NHCOCH$_3$); 139.50 s (C-5'''); 135.50 s (COOCH$_2$C$_6$H$_5$); 122.74 d (C-6'''); 97.10 d (C-1); 82.64 d (C-3); 74.56 d (C-3'''); 71.90 t (OCH$_2$CO); 70.40 d (C-5); 70.08 d (C-4); 69.92 t (CH$_2$-Ph); 66.75 t (COOCH$_2$C$_6$H$_5$); 63.40 t (C-6); 56.68 d (C-14'''); 56.08 d (C-17'''); 54.60 d (Abu-CH); 52.49 d (C-2); 52.44 d (iGln-CH); 49.96 d (C-9'''); 42.28 s (C-13'''); 39.68 t (C-12'''); 39.49 t (C-24'''); 37.99 t (C-4'''); 36.90 t (C-1'''); 36.55 s (C-10'''); 36.15 t (C-22'''); 35.77 d (C-20'''); 31.87 t (C-7'''); 31.80 d (C-8'''); 30.52 t (iGln-CHCH$_2$CH$_2$); 29.83 t (C-2"); 28.98 t (C-16'''); 28.98 t (C-3"); 28.21 t (C-2'''); 28.00 d (C-25'''); 26.90 t (iGln-CHCH$_2$); 24.55 t (C-23'''); 24.55 t (Abu-CH$_2$); 23.80 t (C-15'''); 23.39 q (NHCOCH$_3$); 22.82 q (C-27'''); 22.55 q (C-26'''); 20.99 t (C-11'''); 19.29 q (C-19'''); 18.69 q (C-21'''); 11.84 q (C-18'''); 10.25 q (Abu-CH$_3$). For C$_{64}$H$_{92}$N$_4$O$_{14}$ calculated: relative molecular mass 1141.4, monoisotopic mass 1140.7. FAB MS, m/z: 1163.6 [M+Na]$^+$. HR MS, m/z: for C$_{64}$H$_{92}$O$_{14}$N$_4$Na=1163.65023 found 1163.65054 [Fragmentation: C$_{37}$H$_{48}$O$_{14}$N$_4$Na=795.30592 found 795.30569; C$_{33}$H$_{44}$O$_{11}$N$_4$Na=695.28988 found 695.28970; C$_{18}$H$_{25}$O$_6$N$_3$Na=402.16356 found 402.16351]

As the side product, 129 mg (8%) of the compounds whose MS spectrum refers N-{2-O-[Benzyl 2-acetamido-2,3-dideoxy-4,6-di-O-(5-cholesten-3β-yl)-α-D-glucopyranosid-3-yl]-glycoloyl}-L-α-aminobutanoyl-D-isoglutamine benzyl ester was obtained. For C$_{95}$H$_{140}$N$_4$O$_{17}$ calculated: relative molecular mass 1609.0, monoisotopic mass 1610.1. FAB MS, m/z: 1633.1 [M+Na]$^+$.

N-[2-O-(2-Acetamido-2,3-dideoxy-6-O-{4-[(3α,8ξ, 9ξ,14ξ)-cholestan-3-yloxy]-4-oxobutanoyl}-D-glucopyranosid-3-yl)-glycoloyl]-L-2-aminobutanoyl-D-isoglutamine (3; DHChS-norAbuMDP)

Benzyl protecting groups of lipoglycopeptide 2 were hydrogenolyzed in acetic acid using 5% Pd on carbon catalyst. The catalyst was filtered off and the filtrate was evaporated to give 3 in 92% yield after chromatography on C18 silica gel column in 98% aqueous acetonitrile. $^1$H NMR spectrum: 5.19 d, 1H, J=3.6 (H-1); 4.69 tt, 1H, J=4.8, 4.8, 11.4, 11.4 (H-3'''); 4.57 dd, 1H, J=4.9, 9.5 (α-iGln); 4.38 dd, 1H, J=6.3, 7.9 (α-Abu); 4.36 d, 1H, J=16.1 (CH$_2$CO); 4.35 dd, 1H, J=2.4, 12.1 (H-6); 4.32 d, 1H, J=16.1 (CH$_2$CO); 4.30 dd, 2H, J=5.0, 12.1 (H-6); 4.16 dd, 1H, J=3.6, 10.2 (H-2); 4.07 ddd, 1H, J=2.4, 5.0, 9.4 (H-5); 3.72 dd, 1H, J=9.0, 10.2 (H-3); 3.68 dd, 1H, J=9.0, 9.4 (H-3); 2.67-2.64 m, 2H (H-3"); 2.62-2.59 m, 2H (H-2"); 2.47 t, 2H, J=7.5 (γ-iGln); 2.20-0.95 m, 19H (H-4'''-H-17'''); 2.06 s, 3H (NHCOCH$_3$); 1.90-1.82 m, 1H (β-iGln); 1.76-1.73 m, 1H (β-iGln); 1.58-1.52 m, 2H (β-Abu); 0.93 t, 3H, J=7.4 (γ-iGln); 0.90 d, 3H, J=6.7 (H-21'''); 0.84 d, 3H, J=6.6 (H-27'''); 0.83 d, 3H, J=6.6 (H-26'''); 0.82 s, 3H (H-19'''); 0.65 s, 3H (H-18'''). $^{13}$C NMR spectrum: 178.81 s (CH$_2$OCO); 177.10 s (C-4"); 174.50 s (CONH$_2$); 174.34 s (CH$_2$CH$_2$COOH); 174.28 s (Abu-CO); 174.00 s (OCH$_2$CO); 169.50 s (NHCOCH$_3$); 92.41 d (C-1); 82.00 d (C-3); 75.61 d (C-3'''); 71.79 t (OCH$_2$CO); 71.19 d (C-4); 70.59 d (C-5); 64.65 d (C-6); 57.43 d (C-17'''); 57.34 d (C-14'''); 56.01 d (Abu-CH); 55.28 d (C-9'''); 54.40 d (C-2); 53.42 d (iGln-CH); 45.52 d (C-5'''); 43.48 s (C-13'''); 40.99 t (C-12'''); 40.36 t (C-24'''); 37.52 t (C-1'''); 37.05 t (C-22'''); 36.81 d (C-20'''); 36.47 d (C-8'''); 36.27 s (C-10'''); 34.72 t (C-4'''); 32.85 t (C-7'''); 30.87 t (iGln-CHCH$_2$CH$_2$); 30.17 t (C-2''); 29.78 t (C-3''); 29.09 t (C-6'''); 28.79 d (C-25'''); 28.20 t (C-16'''); 27.42 t (C-2'''); 25.81 t (iGln-CHCH$_2$); 24.98 t (Abu-CH$_2$); 24.98 t (C-15'''); 24.67 t (C-23'''); 23.07 q (C-27'''); 22.83 q (C-26'''); 22.72 q (NHCOCH$_3$); 22.05 t (C-11'''); 19.10 q (C-21'''); 12.52 q (C-19'''); 12.42 q (C-18'''); 10.52 q (Abu-CH$_3$). For C$_{50}$H$_{80}$N$_4$O$_{14}$ calculated: relative molecular mass 961.2, monoisotopic mass 960.6. FAB MS, m/z: 983.6 [M+Na]$^+$. HR MS, m/z: for C$_{50}$H$_{82}$O$_{14}$N$_4$Na=985.57198 found 985.57176 [Fragmentation: C$_{39}$H$_{63}$O$_8$NNa=696.44459 found 696.44419; C$_{23}$H$_{36}$O$_{14}$N$_4$Na=615.21202 found 615.21169; C$_{11}$H$_{19}$O$_6$N$_3$Na=312.11661 found 312.11657]

N-[38]-L-α-aminobutanoyl-D-isoglutamine (ChS-nor-AbuMDP)

The obtained protected lipoglycopeptide 2 was deprotected by hydrogenolysis of benzyl groups by Pd(OH)$_2$—C catalyzed reaction with cyclohexene. For (C$_{50}$H$_{80}$N$_4$O$_{14}$) calculated: relative molecular mass 961.2, monoisotopic mass 960.6. FAB MS, m/z: 983.6 [M+Na]$^+$.

Example 2

Preparation of Normuramic Acid Compounds

Benzyl 2-acetamido-3-O-allyl-4,6-di-O-benzyl-2-deoxy-α-D-glucopyranoside (5)

A solution of benzyl 2-acetamido-3-O-allyl-2-deoxy-α-D-glucopyranoside 4 (ref.[25]; 10.5 g, 29.9 mmol) and benzyl bromide (7.7 ml, 65 mmol) in dry N,N-dimethylformamide (75 ml) was gradually added to a stirred suspension of sodium hydride (60% in mineral oil; 2.8 g, 70 mmol) in N,N-dimethylformamide (25 ml) under argon at 0° C. during 30 min, and the whole was stirred at room temperature for 24 h. A solid carbon dioxide was added and the excess of sodium hydride was decomposed with water and the mixture was evaporated. The solid residue was partitioned between toluene (500 ml) and water (100 ml), organic layer was washed with water (2×100 ml), dried (MgSO$_4$) and evaporated. Chromatography of the residue on a silica gel column (500 g) in toluene-ethyl acetate (2:1) afforded 14.2 g (89%) of 5 as white solid, which was crystallized from toluene-n-heptane; m.p. 152-153° C., [α]$_D$+109° (c 0.5, chloroform); ref.[39]: m.p. 137.5-138.5° C. (diethyl ether), [α]$_D$+102° (c 1.0, chloroform). IR and $^1$H NMR spectra correspond with the respective data for the authentic sample described in ref.[39]. $^1$H NMR: 7.16-7.37 m, 15H (H-arom.); 5.87 ddt, 1 H, J=5.8, 5.8, 10.3, 17.1 (OCH$_2$—CH=CH$_2$); 5.56 bd, 1 H, J=9.6 (NHCOCH$_3$); 5.23 dq, 1 H, J=1.7, 1.7, 1.7, 17.1 (OCH$_2$—CH=CHH); 5.17 dq, 1 H, J=1.5, 1.5, 1.5, 10.3 (OCH$_2$—CH=CHH); 4.90 d, 1 H, J=3.8 (H-1); 4.79 d, 1 H, J=10.6 (CH$_2$-Ph); 4.70 d, 1 H, J=11.7 (CH$_2$-Ph); 4.63 d, 1 H, J=12.2 (CH$_2$-Ph); 4.53 d, 1 H, J=12.2 (CH$_2$-Ph); 4.50 d, 1 H, J=10.6 (CH$_2$-Ph); 4.45 d, 1 H, J=11.7 (CH$_2$-Ph); 4.30 ddt, 1 H, J=1.4, 1.4, 5.2, 12.6 (OCHHCH=CH$_2$); 4.29 ddd, 1 H, J=3.8, 9.6, 10.6 (H-2); 4.09 ddt, 1 H, J=1.4, 1.4, 6.1, 12.6 (OCHHCH=CH$_2$); 3.81 ddd, 1 H, J=2.0, 4.1, 9.9 (H-5); 3.73 dd, 1 H, J=4.1, 10.6 (H-6a); 3.69 dd, 1 H, J=8.8, 9.9 (H-4); 3.64 dd, 1 H, J=2.0, 10.6 (H-6b); 3.59 dd, 1 H, J=8.8, 10.6 (H-3); 1.96 s, 3 H (NHCOCH$_3$). $^{13}$C NMR: 169.7 (NHCOCH$_3$), 138.0 (2C), 137.2 (C-arom.), 135.0 (OCH$_2$—CH=CH$_2$), 128.6 (2C), 128.4 (3C), 128.2 (2C), 128.1 (2C), 128.0 (2C), 127.8 (2C), 127.6 (C-arom.), 116.9 (OCH$_2$—CH=CH$_2$), 97.3 (C-1), 80.8 (C-3), 78.0 (C-4), 75.0 (CH$_2$-Ph), 73.7 (CH$_2$-Ph), 73.4 (OCH$_2$—CH=CH$_2$), 71.2 (C-5), 69.6 (CH$_2$-Ph), 68.5 (C-6), 52.5 (C-2), 23.4 (NHCOCH$_3$). For C$_{32}$H$_{37}$NO$_6$ calculated: relative molecular mass 531.6, monoisotopic mass 531.3. FAB MS, m/z: 532.2 [M+H]$^+$. For C$_{32}$H$_{37}$NO$_6$ (531.6) calculated: 72.29% C, 7.01% H, 2.63% N; found 72.44% C, 6.98% H, 2.68% N.

Oxidation of Benzyl 2-acetamido-3-O-allyl-4,6-di-O-benzyl-2-deoxy-α-D-glucopyranoside (5)

Method A: To an intensively stirred solution of 5 (2.127 g, 4 mmol) in a mixture of tetrachloromethane-acetonitrile (3:2, 150 ml) water (20 ml) was added, the fine emulsion was cooled to 0° C. and 0.425M aqueous solution of sodium periodate (10 ml, 4.25 mmol) and 0.25% aqueous solution of ruthenium(III) chloride (20 ml) were added. The whole was stirred at the same temperature for 30 min, than another portion of 0.425M solution of sodium periodate (10 ml, 4.25 mmol) was added and the stirring was continued for another 1 h. The reaction course was monitored by TLC in ethyl acetate-methanol (20:1) and in chloroform-methanol (20:1). 2-Propanol (10 ml) was added and the stirring was continued at 0° C. for 1 h. The mixture was saturated with sodium chloride and extracted with chloroform (4×50 ml). The combined extracts were dried (Na$_2$SO$_4$) and evaporated, to give syrupy residue. The residue was purified on a silica gel column (200 g). The column was eluted first with a mixture of toluene-ethyl acetate (5:1) to give 62 mg (3%) of the solid compound 8, which was crystallized from n-heptane. Yield 43 mg (2%) of compound 8 identical (m.p., [α]$_D$, MS, IR and NMR spectra) with the authentic sample 8 described below. Further elution with a mixture of toluene-ethyl acetate (2:1) afforded 106 mg (5%) of the solid starting material 5, identical (m.p., [α]$_D$, MS, IR and NMR spectra) after crystallization from toluene-N-heptane with the authentic compound 5. Continued elution of the column with a mixture of toluene-ethylacetate (1:5) afforded 555 mg (26%) of the solid compound 7, which was crystallized from a mixture toluene-N-heptane, to yield 320 mg (15%) of 7, identical (m.p., [α]$_D$, MS, IR and NMR spectra) with the authentic sample 7 described below. Finally, the elution with ethyl acetate gave 1.2 g (53%) of the crude 6. It was dissolved in chloroform (50 ml) and 1M aqueous solution of sodium sulfite (20 ml, 20 mmol) was added and pH of the well stirred mixture was adjusted by addition of saturated aqueous solution of sodium hydrogen sulfate to pH 2-4 and the stirring was continued for 30 min. Than the organic layer was separated and washed with brine (2×50 ml), dried (Na$_2$SO$_4$) and evaporated and the residue was crystallized from toluene, to yield a mixture of diastereomers of 6 (860 mg, 38%).

Method B: Benzyl 2-acetamido-3-O-allyl-4,6-di-O-benzyl-2-deoxy-α-D-glucopyranoside 5 (1.063 g, 2 mmol) and sodium periodate (1.71 g, 8 mmol) were taken in a mixture of tetrachloromethane-acetonitrile-water (2:1:1, 40 ml). RuCl$_3$ (29 mg, 7 mol %) was then added to it and the mixture was vigorously stirred at 0-5° C. The progress of the reaction was monitored by TLC in chloroform-methanol-formic acid (100:5:2) and in chloroform-methanol-triethylamine (50:5:1). After 4 hours no starting material was detected on TLC. The reaction mixture was then cooled to 0° C. (ice bath). 2M aqueous sodium sulfite (40 ml) was then added to it and the mixture was stirred for 30 mins. Saturated aqueous solution of sodium hydrogen sulfate was then added to it until the pH of the reaction mixture was 2-4. The stirring was continued for another 30 min. The reaction mixture was then extracted with chloroform (3×20 ml), the combined extracts were dried (MgSO$_4$) and solvent evaporated. Chromatography of the residue on a silica gel column (100 g) in chloroform-ethyl acetate-formic acid (25:25:1) afforded colorless solid. It was then crystallized from ethyl acetate and petroleum ether mixture to obtain 0.86 g (78%) of 9.

Benzyl 2-acetamido-4,6-di-O-benzyl-2-deoxy-3-O-(2,3-dihydroxypropyl)-α-D-glucopyranoside (6)

M.p. 165-166° C., [α]$_D$ +81° (c 1.6, chloroform). IR (chloroform): 3 630 (O—H); 3 570, 3 489 (O—H, bonded); 3 437 (N—H, NHAc); 3 090, 3 068 (C—H, arom.); 1 671 (amide I); 1 606, 1 587, 1 498, 1 455 (arom. ring); 1 513 (amide II). For C$_{32}$H$_{39}$NO$_8$ calculated: relative molecular mass 565.7, monoisotopic mass 565.3. FAB MS, m/z: 566.4 [M+H]$^+$, 588.4 [M+Na]$^+$. For C$_{32}$H$_{39}$NO$_8$ (565.7) calculated: 67.95% C, 6.95% H, 2.48% N; found: 67.83% C, 7.06% H, 2.37% N. The compound 6 was fully characterized after converting it to di-O-acetate 10 as described below.

Benzyl 2-acetamido-4,6-di-O-benzyl-3-O-carboxymethyl-2-deoxy-α-D-glucopyrano-side (9)

Mp. 128-129° C. [α]$_D$ +116° (c 0.5, chloroform). IR (chloroform): 3500 (O—H, COOH); 2736, 2629, 2532 (O—H, COOH, dimer); 3433 (N—H, NHAc); 3208 (N—H, NHAc, bonded); 3090, 3068, 3032 (C—H, arom); 1751, 1718 (C=O, COOH); 1669 (amide I), 1568 (amide II, bonded); 1512 (amide II); 1497, 1455 (arom. ring). $^1$H NMR: 7.89 bd, 1H, J=5.5 (NHCOCH$_3$); 7.17-7.37 m, 15H (H-arom.); 5.27 d, 1 H, J=3.7 (H-1); 4.67 d, 1 H, J=10.9 (CH$_2$-Ph); 4.65 d, 1 H, J=12.1 (CH$_2$-Ph); 4.64 d, 1 H, J=12.0 (CH$_2$-Ph); 4.56 d, 1 H, J=10.9 (CH$_2$-Ph); 4.52 d, 1 H, J=12.1 (CH$_2$-Ph); 4.48 d, 1 H, J=12.0 (CH$_2$-Ph); 4.38 d, 1 H, J=17.5 (OCH$_2$COOH); 4.28 d, 1 H, J=17.5 (OCH$_2$COOH); 3.93 ddd, 1 H, J=3.7, 5.8, 10.2 (H-5); 3.7-3.78 m, 3H (H-2, H-3, H-4); 3.58-3.78 m, 1H (H-6); 1.99 s, 3 H (NHCOCH$_3$). $^{13}$C NMR: 173.7 (OCH$_2$CO$_2$H), 172.3 (NHCOCH$_3$), 137.87, 137.4, 137.3, 128.6, 128.5, 128.4, 128.0, 127.9, 127.8, 127.7 (C-arom.), 96.3 (C-1), 79.6 (C-3), 79.2 (C-4), 75.0 (CH$_2$-Ph), 73.6 (CH$_2$-Ph), 71.1 (C-5), 70.0 (OCH$_2$CO$_2$H), 68.2 (CH$_2$-Ph), 65.7 (C-6), 54.1 (C-2), 22.6 (NHCOCH$_3$). For C$_{31}$H$_{35}$NO$_8$ calculated: relative molecular mass 549.6, monoisotopic mass 549.2. FAB MS, m/z: 550.1 [M+H]$^+$, 572.1 [M+Na]$^+$. For C$_{31}$H$_{35}$NO$_8$ (549.6) calculated: 67.75% C, 6.42% H, 2.55% N; found: 67.77% C, 6.50% H, 2.50% N.

Benzyl 2-acetamido-3-O-(2,3-diacetoxypropyl)-4,6-di-O-benzyl-2-deoxy-α-D-glucopyranoside (10)

To a stirred solution of 6 (566 mg, 1 mmol) and 4-dimethylaminopyridine (12 mg, 0.1 mmol) in a mixture of dry dichloromethane-pyridine (25:1, 21 ml) acetic anhydride (380 μl, 4 mmol) was slowly added at 0° C. and the mixture was stirred at the same temperature for 1 h and at room temperature overnight. The mixture was cooled to 0° C., methanol (2 ml, 50 mmol) was added and the stirring was continued at room temperature for 2 h. Then the mixture was evaporated and the residue was co-evaporated with toluene (3×10 ml). Chromatography of the residue on a silica gel column (20 g) in toluene-ethyl acetate (1:1) yielded 613 mg (94%) of crystalline compound 10. An analytical sample was crystallized from toluene-N-heptane to give colorless needles corresponding to a mixture of diastereomers of 10 A and B; m.p. 151.5-152.5° C., [α]$_D$ +70° (c 0.2, chloroform). IR (tetrachloromethane): 3 446 (N—H, NHAc); 3 090, 3 067, 3 033 (C—H, arom.); 1 747 (C=O, OAc); 1 692 (amide I); 1 498 (amide II); 1 498, 1 454 (arom. ring); 1 371 (CH$_3$, OAc). $^1$H NMR (ratio diastereomers 5:2); diastereomer A: $^1$H NMR: 7.16-7.38 m, 15H (H-arom.); 5.68 d, 1H, J=9.8 (NHCOCH$_3$); 5.07 ddt, 1H, J=3.9, 5.0, 5.0, 6.1 [CH$_2$CH(OAc)CH$_2$(OAc)]; 4.88 d, 1H, J=3.7 (H-1); 4.73 d, 1H, J=12.0 (CH$_2$-Ph); 4.69 d, 1H, J=11.7 (CH$_2$-Ph); 4.63 d, 1H, J=12.1 (CH$_2$-Ph); 4.5 d, 1H, J=12.1 (CH$_2$-Ph); 4.45 d, 1H, J=11.7 (CH$_2$-Ph); 4.31 dd, 1H, J=3.9, 11.9 [CH$_2$CH(OAc)CH$_2$(OAc)]; 4.29 ddd, 1H, J=3.7, 9.8, 10.6 (H-2); 4.20 dd, 1H, J=6.1, 11.9 [CH$_2$CH(OAc)CH$_2$(OAc)]; 4.09 d, 1H, J=12.0 (CH$_2$-Ph); 3.91 dd, 1H, J=4.9, 10.5 [CH$_2$CH(OAc)CH$_2$(OAc)]; 3.80 ddd, 1H, J=2.0, 4.0, 10.0 (H-5); 3.72 dd, 1H, J=5.1, 10.5 [CH$_2$CH(OAc)CH$_2$(OAc)]; 3.72 dd, 1H, J=4.0, 10.8 (H-6b); 3.68 dd, 1H, J=8.8, 10.0 (H-4); 3.63 dd, 1H, J=2.0, 10.8 (H-6a); 3.56 dd, 1H, J=8.8, 10.6 (H-3); 1.99 s, 3H (COCH$_3$), 1.99 s, 3H (COCH$_3$); 1.98 s, 3H (NHCOCH$_3$); diastereomer B: 7.16-7.38 m, 15H (H-arom.); 5.76 d, 1H, J=9.5 (NHCOCH$_3$) 5.07 ddt, 1H, J=3.9, 5.0, 5.0, 6.1 [CH$_2$CH(OAc)CH$_2$(OAc)]; 4.92 d, 1H, J=3.6 (H-1); 4.75 d, 1H, J=10.8 (CH$_2$-Ph); 4.73 d, 1H, J=11.9 (CH$_2$-Ph); 4.64 d, 1H, J=12.1 (CH$_2$-Ph); 4.52 d, 1H, J=12.1 (CH$_2$-Ph); 4.51 d, 1H, J=10.8 (CH$_2$-Ph); 4.26 dd, 1H, J=3.9, 11.9 [CH$_2$CH(OAc)CH$_2$(OAc)] 4.25 ddd, 1H, J=3.6, 9.5, 10.6 (H-2); 4.20 dd, 1H, J=6.1, 11.9 [CH$_2$CH(OAc)CH$_2$(OAc)] 4.10 d, 1H, J=11.9 (CH$_2$-Ph); 3.91 dd, 1H, J=4.9, 10.5 [CH$_2$CH(OAc)CH$_2$(OAc)] 3.80 ddd, 1H, J=2.0, 4.0, 10.0 (H-5); 3.76 dd, 1H, J=5.1, 10.5 [CH$_2$CH(OAc)CH$_2$(OAc)] 3.72 dd, 1H, J=4.0, 10.8 (H-6b); 3.68 dd, 1H, J=8.9, 10.0 (H-4); 3.64 dd, 1H, J=2.0, 10.8 (H-6a); 3.57 dd, 1H, J=8.9, 10.6 (H-3); 2.01 s, 3H (COCH$_3$); 1.99 s, 3H (COCH$_3$); 1.97 s, 3H (NHCOCH$_3$). $^{13}$C NMR; diastereomer A: 170.59 (OCOCH3); 170.45 (OCOCH3); 169.82 (NHCOCH$_3$); 137.96; 137.89; 137.00; 128.00; 97.19 (C-1); 81.86 (C-3); 77.94 (C-4); 74.85 (CH$_2$-Ph); 73.48 (CH$_2$-Ph); 71.18 (C-5); 70.91; 70.83; 13C NMR spectrum: 69.71 (CH$_2$-Ph); 68.39 (C-6); 62.76; 52.27 (C-2); 23.35 (NHCOCH$_3$); 20.93 (OCOCH3); 20.71 (OCOCH$_3$); diastereomer B: 170.23 (OCOCH$_3$); 170.17 (OCOCH$_3$); 169.75 (NHCOCH$_3$); 137.94; 137.80; 137.07; 97.13 (C-1); 81.43 (C-3); 78.27 (C-4); 74.85 (CH$_2$-Ph); 73.48 (CH$_2$-Ph); 71.20 (C-5); 70.91; 70.86; 69.76 (CH$_2$-Ph); 68.36 (C-6); 62.53; 52.51 (C-2); 23.30 (NHCOCH$_3$); 20.92 (OCOCH$_3$); 20.69 (OCOCH$_3$). For C$_{36}$H$_{43}$NO$_{10}$ calculated: relative molecular mass 649.7, monoisotopic mass 649.3. FAB MS, m/z: 650.3 [M+H]$^+$, 672.3 [M+Na]$^+$. For C$_{36}$H$_{43}$NO$_{10}$ (649.7) calculated: 66.55% C, 6.67% H, 2.16% N; found: 66.22% C, 6.70% H, 2.08% N.

Benzyl 2-acetamido-4,6-di-O-benzyl-2-deoxy-3-O-(methoxycarbonyl)-methyl-α-D-glucopyranoside (11)

To a stirred solution of 9 (496 mg, 0.9 mmol) in a mixture dichloromethane-methanol (2:1, 9 ml) at 0° C. the solution of diazomethane in diethyl ether was added until a yellow coloration persisted. After standing at room temperature for 1 h, the excess diazomethane was decomposed with acetic acid and the mixture was evaporated. The residue was crystallized from n-heptane to afford 485 mg (86%,) of 11; m.p. 116-117.5° C., [α]$_D$ +121° (c 0.4, chloroform). IR (tetrachloromethane): 3 368 (N—H, NHAc); 3 090, 3 067, 3 033, 3 007 (C—H, arom.); 1 745 (CO=OCH$_2$COOCH$_3$); 1 681 (amide I); 1 605, 1 587, 1 497, 1 455 (arom. ring); 1 534 (amide II); 1 439 ($CH_3$, $OCH_2COOCH_3$). $^1$H NMR: 7.16-7.37 m, 15H (H-arom.); 5.65 bd, 1H, J=8.5 ($NHCOCH_3$); 5.32 d, 1 H, J=3.5 (H-1); 4.68 d, 1 H, J=10.9 ($CH_2$-Ph); 4.67 d, 1 H, J=12.2 ($CH_2$-Ph); 4.66 d, 1 H, J=12.4 ($CH_2$-Ph); 4.56 d, 1 H, J=10.9 ($CH_2$-Ph); 4.53 d, 1 H, J=12.2 ($CH_2$-Ph); 4.51 d, 1 H, J=12.4 ($CH_2$-Ph); 4.48 d, 1 H, J=17.5 ($OCH_2CO_2CH_3$); 4.29 d, 1 H, J=17.5 ($OCH_2CO_2CH_3$); 3.96 ddd, 1 H, J=3.5, 8.5, 10.7 (H-2); 3.71 s, 3 H ($OCH_2CO_2CH_3$); 3.68-3.76 m, 3 H (H-3, H-4, H-5, H-6); 3.60 dd, 1 H, J=2.0, 10.7 (H-6); 2.03 s, 3 H ($NHCOCH_3$). $^{13}$C NMR: 172.9 ($OCH_2CO_2CH_3$), 170.8 ($NHCOCH_3$), 138.0, 137.7, 137.7, 128.5, 128.4, 128.3(3C), 128.0(3C), 127.9(2C), 127.8(3C), 127.7 (2C) (C-arom., Bn), 96.8 (C-1), 79.6 (C-3), 79.0 (C-4), 74.9 ($CH_2$-Ph), 73.6 ($OCH_2CO_2CH_3$), 71.1 (C-5), 70.0 ($CH_2$-Ph), 68.4 ($CH_2$-Ph), 68.2 (C-6), 53.8 ($OCH_2CO_2CH_3$), 52.0 (C-2), 23.1 ($NHCOCH_3$). For ($C_{32}H_{37}NO_8$) calculated: relative molecular mass 563.6, monoisotopic mass 563.2. FAB MS, m/z: 564.3 $[M+H]^+$, 586.3 $[M+Na]^+$. For $C_{32}H_{37}NO_8$ (563.6) calculated: 68.19% C, 6.62% H, 2.49% N; found: 68.05% C, 6.65% H, 2.43% N.

Benzyl 2-acetamido-4,6-di-O-benzyl-2-deoxy-3-O-(2-formylmethyl)-α-D-glucopyranoside (7)

A solution of lead(IV) acetate (488 mg, 1.1 mmol) in chloroform (5 ml) was added to the stirred solution of 6 (566 mg, 1 mmol) in dry chloroform (30 ml) at 0 C during 10 min and the mixture was stirred at the same temperature for 30 min and at room temperature for 2 h. Saturated aqueous solution of magnesium sulfate (10 ml) was added and the stirring was continued for another 10 min. Organic phase was separated and water phase was extracted with chloroform (2×15 ml). The combined organic phases were washed with brine (2×30 ml), dried ($Na_2SO_4$), and evaporated. The residue was crystallized from toluene-N-heptane to give 336 mg (63%) of 7. An analytical sample was recrystallized from N-heptane; m.p. 115-120° C., $[α]_D$ +90° (c 0.4, chloroform). IR (chloroform): 3 437, 3 368 (N—H, NHAc); 3 090, 3 068, 3 034, 3 007 (C—H, arom.); 2 718 (C—H, CHO); 1 741 (C═O, CHO); 1 673 (amide I); 1 606, 1 587, 1 498, 1 455 (arom. ring); 1 534, 1 511 (amide II). $^1$H NMR: 9.53 bs, 1H (CHO); 7.18-7.37 m, 15H (H-arom.); 6.81 bd, 1H, J=7.5 ($NHCOCH_3$); 5.15 d, 1H, J=3.5 (H-1); 4.67 d, 1H, J=12.2 ($CH_2$-Ph); 4.67 d, 1H, J=11.9 ($CH_2$-Ph); 4.67 d, 1H, J=11.0 ($CH_2$-Ph); 4.57 d, 1H, J=11.0 ($CH_2$-Ph); 4.53 d, 1H, J=12.2 ($CH_2$-Ph); 4.51 d, 1H, J=18.9 ($CH_2$CHO); 4.48 d, 1H, J=11.9 ($CH_2$-Ph); 4.38 d, 1H, J=18.9 ($CH_2$CHO); 4.12 ddd, 1H, J=3.5, 7.5, 10.8 (H-2); 3.60-3.77 m, 5H (H-3-H-6); 2.01 s, 3H ($NHCOCH_3$). $^{13}$C NMR: 201.04; 170.50 ($NHCOCH_3$); 137.91; 137.68; 137.32; 128.53 (2C); 128.45 (2C); 128.40 (2C); 127.92 (5C); 127.85 (2C); 127.71 (2C); 96.89 (C-1); 80.43 (C-3); 79.06 (C-4); 77.40; 74.94 ($CH_2$-Ph); 73.57 ($CH_2$-Ph); 71.15 (C-5); 69.91 ($CH_2$-Ph); 68.25 (C-6); 53.37 (C-2); 23.22 ($NHCOCH_3$). For $C_{31}H_{35}NO_7$ calculated: relative molecular mass 533.6, monoisotopic mass 533.2. FAB MS, m/z: 534.3 $[M+H]^+$. For $C_{31}H_{35}NO_7$ (533.6) calculated: 69.78% C, 6.61% H, 2.62% N; found: 69.60% C, 6.72% H, 2.65% N.

Benzyl 2-acetamido-4,6-di-O-benzyl-2-deoxy-2-N, 3-O-(ethenylene)-α-D-glucopyranoside (8)

A solution of 7 (534 mg, 1 mmol) in toluene (20 ml) was refluxed for 9 h and than evaporated. Chromatography of the residue on a silica gel column (20 g) in toluene-ethyl acetate (10:3) afforded 268 mg (52%) as white solid 8. An analytical sample was crystallized from N-heptane to give colorless needles; m.p. 88-89° C., $[α]^+155°$ (c 0.8, chloroform). IR (tetrachloromethane): 3 091, 3 067, 3 033, 3 007 (C—H, arom.); 1 681 (C═O, NAc); 1 662 (C═C, OCH═CHN); 1 608, 1 587, 1 497, 1 454 (arom. ring,); 1 398 (═C—H, OCH═CHN); 1 300, 1 264 (C—N, NAc); 715 (═C—H, OCH═CHN). $^1$H NMR: 7.25-7.35 m, 15 H (H arom.); 6.42 bd, 1 H, J=3.3 (H-1); 6.02 d, 1 H, J=5.0 (OCH═CHN); 5.99 bd, 1 H, J=5.0 (OCH═CHN); 4.86 d, 1 H, J=10.9 ($CH_2$-Ph); 4.66 d, 1 H, J=11.5 ($CH_2$-Ph); 4.64 d, 1 H, J=12.3 ($CH_2$-Ph); 4.51 d, 1 H, J=11.5 ($CH_2$-Ph); 4.50 d, 1 H, J=12.3 ($CH_2$-Ph); 4.49 d, 1 H, J=10.9 ($CH_2$-Ph); 4.26 t, 1 H, J=9.4 (H-3); 3.86 ddd, 1 H, J=1.9, 3.5, 9.9 (H-5); 3.77 dd, 1 H, J=9.3, 9.9 (H-4); 3.75 dd, 1 H, J=3.5, 10.8 (H-6a); 3.66 dd, 1 H, J=3.3, 9.6 (H-2); 3.59 dd, 1 H, J=1.9, 10.8 (H-6b); 2.13 s, 3 H ($NCOCH_3$), $^{13}$C NMR: 168.2 ($NCOCH_3$), 138.2, 138.1, 137.8 (C-arom.), 128.7 (OCH═CHN), 128.4 (2C), 128.3 (2C), 128.2 (2C), 128.0 (2C), 127.9 (2C), 127.9 (2C), 127.7, 127.6, 127.6 (C-arom.), 109.3 (OCH═CHN), 96.0 (C-1), 77.5 (C-3), 75.4 (C-5), 74.9 ($CH_2Ph$), 73.5 ($CH_2Ph$), 70.6 ($CH_2Ph$), 70.2 (C-4), 68.3 (C-6), 57.8 (C-2), 22.7 ($NCOCH_3$). For $C_{31}H_{33}NO_6$ calculated: relative molecular mass 515.6, monoisotopic mass 515.2. FAB MS, m/z: 516.3 $[M+H]^+$. For $C_{31}H_{33}NO_6$ (515.6) calculated: 72.21% C, 6.45% H, 2.72% N; found: 72.10% C, 6.46% H, 2.81% N.

Example 3

Preparation of glucosaminylnormuramic Acid Compounds

Benzyl 3,4,6-tri-O-benzyl-2-deoxy-2-[(2,2,2-trichloroethoxy)carbonyl]-amino-β-D-glucopyranosyl-(1→4)-2-acetamido-3-O-allyl-6-O-benzyl-2-deoxy-α-D-glucopyranoside (14)

To a stirred solution of benzyl 2-amino-3,4,6-tri-O-benzyl-2-deoxy-β-D-glucopyranosyl-(1→4)-2-acetamido-3-O-allyl-6-O-benzyl-2-deoxy-α-D-glucopyranoside 12 (ref.$^{29}$; 873 mg, 1 mmol) and 4-dimethylaminopyridine (12 mg, 0.1 mmol) in a mixture of dry dichloromethane-pyridine (12:1; 26 ml) under argon in apparatus equipped with a septum at 0° C. 1M solution of 2,2,2-trichloroethoxycarbonyl chloride in dry dichloromethane (3 ml, 3 mmol) was slowly added through the septum and the mixture was stirred at the same temperature for 1 h and at room temperature for 12 h. The mixture was cooled to 0° C., methanol (2 ml, 50 mmol) was added and the stirring was continued at room temperature for additional 2 h. Then the mixture was evaporated and the residue was dissolved in dichloromethane (50 ml). The solution was extracted with cold 5% aqueous sodium hydrogen sulfate (3×30 ml), cold saturated aqueous solution of sodium hydrogen carbonate (2×20 ml), washed with brine (3×20 ml), dried ($MgSO_4$) and evaporated. Chromatography of the residue on a silica gel column (30 g) in chloroform-ethyl acetate (5:1) followed by crystallization from dichloromethane-n-heptane afforded 776 mg (74%) of 14; m.p. 186-188° C., $[α]_D$ +36° (c 1.4, chloroform). IR (chloroform): 3443 (N—H, Ac); 3394 (N—H, Troc); 3089, 3067, 3033 (C—H, arom); 1749 (C═O, Troc); 1677 (amide I); 1648 (C═C); 1516 (amide II); 1607, 1587, 1497, 1454 (arom. ring). $^1$H NMR spectrum: 7.45-7.20 m, 25H (H-arom.); 5.77 dddd, 1H, J=4.8, 6.3, 10.4, 17.3 ($CH_2CH$═$CH_2$); 5.46 bd, 1H, J=9.1 ($NHCOCH_3$); 5.14 dq, 1H, J=1.7, 1.7, 1.7, 17.3 ($CH_2CH$═$CH_2$); 4.99 ddt, 1H, J=1.3, 1.3, 2.1, 10.4 ($CH_2CH$═$CH_2$); 4.94 d, 1H, J=3.8 (H-1); 4.80 d, 1H, J=12.1 ($CH_2$-Ph); 4.76 d, 1H, J=11.2 ($CH_2$-Ph); 4.73 d, 1H, J=10.9 ($CH_2$-Ph); 4.64 d, 1H, J=11.9

($CH_2$-Ph); 4.64 d, 1H, J=11.5 ($CH_2$-Ph); 4.60 d, 1H, J=11.2 ($CH_2$-Ph); 4.58 d, 1H, J=11.5 ($CH_2$-Ph); 4.57 d, 1H, J=10.9 ($CH_2$-Ph); 4.56 d, 1H, J=12.0 ($CO_2CH_2CCl_3$); 4.50 d, 1H, J=12.0 ($CO_2CH_2CCl_3$); 4.44 d, 1H, J=11.9 ($CH_2$-Ph); 4.42 ddt, 1H, J=1.6, 1.6, 4.8, 13.4 ($CH_2CH=CH_2$); 4.35 d, 1H, J=12.1 ($CH_2$-Ph); 4.20 bd, 1H, J=8.1 (H-1'); 4.19 ddd, 1H, J=3.8, 9.1, 10.6 (H-2); 3.99 bd, 1H, J=10.0 ($NHCO_2CH_2CCl_3$); 3.93 ddt, 1H, J=1.4, 1.4,6.3, 13.4 ($CH_2CH=CH_2$); 3.87 dd, 1H, J=8.8, 9.8 (H-4); 3.74 dd, 1H, J=2.4, 10.8 (H-6a'); 3.73 dd, 1H, J=3.4, 10.6 (H-6a); 3.70 dd, 1H, J=3.7, 10.8 (H-6b'); 3.66 ddd, 1H, J=2.4, 3.4, 9.8 (H-5); 3.66 dd, 1H, J=8.8, 9.8 (H-4'); 3.50-3.42 m, 1H (H-6b); 3.50-3.42 m, 1H (H-3); 3.50-3.42 m, 1H (H-2'); 3.27 bdt, 1H, J=2.9, 2.9, 9.8 (H-5'); 3.23 bt, 1H, J=9.6, 9.6 (H-3'); 1.93 s, 3H ($NHCOCH_3$). $^{13}C$ NMR spektrum: 173.11 ($CO_2CH_2CCl_3$); 169.59 ($COCH_3$); 138.62; 138.23; 138.16; 137.91; 137.14; 135.90 ($CH_2CH=CH_2$); 129.22; 128.89; 128.56 (2C); 128.40 (3C); 128.39 (3C); 128.33 (3C); 128.10; 128.07 (3C); 127.89 (2C); 127.76; 127.70; 127.64 (2C); 127.59; 127.49; 115.87 ($CH_2CH=CH_2$); 100.76 (C'-1); 97.05 (C-1); 95.66 ($CO_2CH_2CCl_3$); 82.11 (C'-3); 78.52 (C-3); 78.28 (C'-4); 77.19 (C-4); 74.80 ($CH_2$-Ph); 74.73 ($CO_2CH_2CCl_3$); 74.71 (C'-5); 74.52 ($CH_2$-Ph); 73.61 ($CH_2$-Ph); 73.46 ($CH_2$-Ph); 73.37 ($CH_2CH=CH_2$); 70.57 (C-5); 69.89 ($CH_2$-Ph); 68.71 (C-6); 67.79 (C'-6); 57.89 (C'-2); 52.33 (C-2); 23.34 ($COCH_3$).

For $C_{55}H_{61}Cl_3N_2O_{12}$ calculated: relative molecular mass 1 048.5, monoisotopic mass 1 046.3. FAB MS, m/z: 1 047.4 [M+H]$^+$, 1 069.4 [M+Na]$^+$. For $C_{55}H_{61}Cl_3N_2O_{12}$ (1 48.5) calculated: 63.01% C, 5.86% H, 10.14% Cl, 2.67% N; found: 62.81% C, 5.87% H, 10.22% Cl, 2.58% N.

Benzyl 2-acetamido-3,4,6-tri-O-benzyl-2-deoxy-β-D-glucopyranosyl-(1→4)-2-acetamido-6-O-benzyl-3-O-carboxymethyl-2-deoxy-α-D-glucopyranoside (15)

Compound (13, ref.[25,29]; 915 mg, 1 mmol) and sodium periodate (0.86 g, 4 mmol) were taken in a mixture of tetrachloromethane-acetonitrile-water (2:1:1, 40 ml). $RuCl_3$ (14.5 mg, 7 mol %) was then added to it and the mixture was vigorously stirred at 0-5° C. The progress of the reaction was monitored by TLC in chloroform-methanol-formic acid (100:5:2) andin chloroform-methanol-triethylamine (50:5:1). After 4 hours no starting material was detected on TLC. 2M aqueous sodium sulfite (40 ml) was then added to it and the mixture was stirred for 30 min. Saturated aqueous solution of sodium hydrogen sulfate was then added to it until the pH of the reaction mixture was 2-4. The stirring was continued for another 30 min. The reaction mixture was then extracted with chloroform (3×20 ml), the combined extracts were dried ($MgSO_4$) and solvent evaporated. Chromatography of the residue on a silica gel (150 g) in chloroform-ethyl acetate-formic acid (25:25:1) afforded 532 mg (57%) of 15 as a solid residue which was crystallized from toluene to give 467 mg (50%) of 15; m.p. 219-225 C (dec.), [α]$_D$ +55° (c 0.5, chloroform); compound 15 is described in ref.[25] as non characterized syrup. IR (chloroform): 3 458, 3 430, 3 403, 3 316, 3 210 (N—H, NHAc); 3 089, 3 067, 3032 (C—H, arom.); 1771 (C=O, $OCH_2COOH$); 1 737 (C=O, $OCH_2COOH$, dimer); 1 674, 1 653 (amide I); 1 605, 1 586, 1 497, 1 454 (arom. ring); 1 539, 1 518 (amide II). For $C_{53}H_{60}N_2O_{13}$ calculated: relative molecular mass 933.1, monoisotopic mass 932.4. FAB MS, m/z: 933.3 [M+H]$^+$, 955.3 [M+Na]$^+$. For $C_{53}H_{60}N_2O_{13}$ (933.1) calculated: 68.22% C, 6.48% H, 3.00% N; found: 68.07% C, 6.47% H, 2.91% N. The compound 15 was fully characterized after conversion to methyl ester 17 described below.

Benzyl 3,4,6-tri-O-benzyl-2-deoxy-2-[(2,2,2-trichloroethoxy)carbonyl]-amino-β-D-glucopyranosyl-(1→4)-2-acetamido-6-O-benzyl-3-O-carboxymethyl-2-deoxy-α-D-glucopyranoside (16)

Compound 14 (1.048 g, 1 mmol) and sodium periodate (0.32 g, 1.5 mmol) were taken in a mixture of tetrachloromethane-acetonitrile-water (2:1:1, 40 ml). $RuCl_3$ (14.5 mg, 7 mol %) was then added to it and the mixture was vigorously stirred at room temperature (25° C.). The progress of the reaction was monitored by TLC in chloroform-methanol-formic acid (100:5:2) and in chloroform-methanol-triethylamine (50:5:1). After 4 hours no starting material was detected on TLC. The reaction mixture was then cooled to 0° C. (ice bath). 2M aqueous sodium sulfite (40 ml) was then added to it and the mixture was stirred for 30 min. Saturated aqueous solution of sodium hydrogen sulfate was then added to it until the pH of the reaction mixture was 2-4. The stirring was continued for another 30 min. The reaction mixture was then extracted with chloroform (3×20 ml), the combined extracts were dried ($MgSO_4$) and solvent evaporated. Chromatography of the residue on a silica gel column (150 g) in chloroform-ethyl acetate-formic acid (25:25:1) afforded 683 mg (64%) of 16 as a solid residue. It was then crystallized from ethyl acetate and petroleum ether to obtain mg (55%) 16; m.p. 174-175° C. (dec.), [α]$_D$ +43° (c 0.7, chloroform). IR (chloroform): 3515 (OH, COOH); 3392 (N—H, Troc); 3433 (N—H, Ac); 3090, 3067, 3032 (C—H, arom.); 2737, 2629, 2532 (OH, COOH, dimer); 1750 (C=O, Troc); 1720 (C=O, COOH); 1675 (amide I), 1560 (amide II, bonded); 1518 (amide II); 1497, 1454 (arom. ring) For $C_{54}H_{59}Cl_3N_2O_{14}$ calculated: relative molecular mass 1 066.4, monoisotopic mass 1 064.3. FAB MS, m/z: 1 065.3, 1 067.3 [M+H]$^+$, 1 087.3, 1 089.3 [M+Na]$^+$. For $C_{54}H_{59}Cl_3N_2O_{14}$ (1 066.4) calculated: 60.82% C, 5.58% H, 9.97% Cl, 2.63% N; found: 61.04% C, 5.70% H, 10.01% Cl, 2.77% N. The compound 16 was fully characterized after conversion to methyl ester 18 described below.

Benzyl 2-acetamido-3,4,6-tri-O-benzyl-2-deoxy-β-D-glucopyranosyl-(1→4)-2-acetamido-6-O-benzyl-2-deoxy-3-O-(meth oxycarbonyl)methyl-α-D-glucopyranoside (17)

To a stirred solution of 15 (933 mg, 1 mmol) in a mixture of dichloromethane-methanol (2:1, 75 ml) at 0° C. the solution of diazomethane in diethyl ether was added until a yellow coloration persisted. After standing at room temperature for 1 h, the excess diazomethane was decomposed with acetic acid and the mixture was evaporated. Chromatography of the residue on a silica gel C18 column in methanol-water (18:5) afforded 881 mg (93%) of 17 as a crystalline residue, which was crystallized from methanol; m.p. 221-223° C., [α]$_D$+67° (c 0.5, chloroform); ref.[25]: m.p. 223° C. (methanol), [α]$_D$ +67° (c 0.5, chloroform). IR (chloroform): 3 404, 3 349 (N—H, NHAc); 3 090, 3 067, 3 032 (C—H, arom.); 1 738 (C=O, $OCH_2COOCH_3$); 1 675 (amide I); 1 607, 1 586, 1 497, 1 454 (arom. ring); 1 539, 1 520 (amide II); 1 441 ($CH_3$, $OCH_2COOCH_3$). $^1H$ NMR: 7.82 d, 2 H, J=4.5 ($NHCOCH_3$, N'H'C'O'C'H'$_3$); 7.21-7.39 m, 25 H (H-arom.,); 5.42 d, 1 H, J=3.4 (H-1); 4.82 d, 1 H, J=12.1 ($CH_2$-Ph); 4.79 d, 1 H, J=12.1 ($CH_2$-Ph); 4.76 d, 1 H, J=10.9 ($CH_2$-Ph); 4.62 d, 1 H, J=12.0 ($CH_2$-Ph); 4.58 d, 1 H, J=12.1 ($CH_2$-Ph); 4.58 d, 1 H, J=11.9

(CH$_2$-Ph); 4.58 d, 1 H, J=10.9 (CH$_2$-Ph); 4.53 d, 1 H, J=18.5 (OCH$_2$CO$_2$CH$_3$); 4.51 d, 1 H, J=12.0 (CH$_2$-Ph); 4.49 d, 1 H, J=11.9 (CH$_2$-Ph); 4.37 d, 1 H, J=9.4 (H-1'); 4.30 d, 1 H, J=12.1 (CH$_2$-Ph); 4.28 d, 1 H, J=18.5 (OCH$_2$CO$_2$CH$_3$); 3.88 dd, 1 H, J=8.8, 10.0 (H-1); 3.81 ddd, 1 H, J=3.4, 4.5, 11.0 (H-2); 3.77 dd, 1 H, J=2.9, 10.6 (H-6'a); 3.76 dd, 1 H, J=2.6, 10.6 (H-6'b); 3.75 ddd, 1 H, J=8.4, 9.4, 10.2 (H-2'); 3.75 dd, 1 H, J=8.9, 9.7 (H-4'); 3.66 dd, 1 H, J=8.8, 11.0 (H-3); 3.65 s, 3 H (OCH$_2$CO$_2$CH$_3$); 3.60 dt, 1 H, J=2.5, 2.5, 10.0 (H-5); 3.54 dd, 1 H, J=2.6, 10.5 (H-6a); 3.36 dd, 1 H, J=2.5, 10.5 (H-6b); 3.34 ddd, 1 H, J=2.6, 2.9, 9.7 (H-5'); 3.34 dd, 1 H, J=8.9, 10.2 (H-3'); 2.00 s, 3 H (NHCOCH$_3$); 1.66 s, 3 H (N'H'C'O'C'H'$_3$). $^{13}$C NMR: 174.2 (OCH$_2$CO$_2$CH$_3$), 170.8 (NHCOCH$_3$, 169.7 (NHCOCH$_3$), 138.4, 138.1, 138.1, 138.1, 137.8, 129.2 (2C), 128.8 (2C), 128.5 (3C), 128.4, 128.3 (2C), 128.3 (2C), 128.0 (2C), 127.9, 127.7, 127.7 (4C), 127.6, 127.5, 127.4 (3C) (C-arom.), 100.5 (C-1'), 96.7 (C-1), 82.2 (C-3'), 78.2 (C-4'), 78.0 (C-4), 77.2 (C-3), 74.8 (CH$_2$-Ph), 74.6 (CH$_2$-Ph), 74.4 (C-5'), 73.7 (CH$_2$-Ph), 73.2 (CH$_2$-Ph), 70.3 (CH$_2$-Ph), 70.1 (C-5), 69.1 (OCH$_2$CO$_2$CH$_3$), 68.7 (C-6'), 67.6 (C-6), 55.6 (C-2'), 54.2 (C-2), 51.7 (OCH$_2$CO$_2$CH$_3$), 23.4 (N'H'C'O'C'H'$_3$), 23.1 (NHCOCH$_3$). For C$_{54}$H$_{62}$N$_2$O$_{13}$ calculated: relative molecular mass 947.1, monoisotopic mass 946.4. FAB MS, m/z: 947.4 [M+H]$^+$, 969.4 [M+Na]$^+$. For C$_{54}$H$_{62}$N$_2$O$_{13}$ (947.1) calculated: 68.48% C, 6.60% H, 2.96% N; found: 68.43% C, 6.62% H, 2.90% N.

Benzyl 3,4,6-tri-O-benzyl-2-deoxy-2-[(2,2,2-trichloroethoxy)carbonyl]-amino-β-D-glucopyranosyl-(1→4)-2-acetamido-6-O-benzyl-2-deoxy-3-O-(methoxy-carbonyl)methyl-α-D-glucopyranoside (18)

To a stirred solution of 16 (1.066 mg, 1 mmol) in a mixture of dichloromethane-methanol (2:1, 75 ml) at 0° C. the solution of diazomethane in diethyl ether was added until a yellow coloration persisted. After standing at room temperature for 1 h, the excess diazomethane was decomposed with acetic acid and the mixture was evaporated. Chromatography of the residue on silica gel (80 g) in chloroform-acetone (10:2) afforded 983 mg (91%) of 18 as a white solid, which was crystallized from toluene-n-heptane; m.p. 176.5-178.5° C., [α]$_D$ +49° (c 0.6, chloroform). IR (tetrachloromethane): 3 460, 3 396, 3 357 (N—H, NHAc and NHTroc); 3 090, 3 067, 3 032, 3 007 (C—H, arom.); 1 760 (C=O, OCH$_2$COOCH$_3$); 1 741 (CO=HNCOO and OCH$_2$COOCH$_3$); 1 680 (amide I); 1 607, 1 587, 1 497, 1 454 (arom. ring); 1 527, 1 521 (amide II); 1 440 (CH$_3$, OCH$_2$COOCH$_3$). $^1$H NMR: 7.84 bd, 1 H, J=4.5 (NH-COCH$_3$); 7.18-7.47 m, 25 H (H-arom.); 5.44 d, 1 H, J=3.4 (H-1); 4.86 d, 1 H, J=12.0 (CH$_2$-Ph); 4.81 d, 1 H, J=12.0 (CH$_2$CCl$_3$); 4.77 d, 1 H, J=11.5 (CH$_2$-Ph); 4.74 d, 1 H, J=10.9 (CH$_2$-Ph); 4.60 d, 1 H, J=11.9 (CH$_2$-Ph); 4.59 d, 1 H, J=11.9 (CH$_2$-Ph); 4.57 d, 1 H, J=11.5 (CH$_2$-Ph); 4.56 d, 1 H, J=10.9 (CH$_2$-Ph); 4.53 d, 1 H, J=12.0 (CH$_2$CCl$_3$); 4.50 d, 1 H, J=11.9 (CH$_2$-Ph); 4.49 d, 1 H, J=18.8 (OCH$_2$CO$_2$CH$_3$); 4.47 d, 1 H, J=11.9 (CH$_2$-Ph); 4.28 d, 1 H, J=18.8 (OCH$_2$CO$_2$CH$_3$); 4.27 d, 1 H, J=12.0 (CH$_2$-Ph); 4.03 d, 1 H, J=8.4 (H-1'); 3.86 bt, 1 H, J=8.9, 10.0 (H-4); 3.81 ddd, 1 H, J=3.4, 4.5, 11.0 (H-2); 3.77 dd, 1 H, J=2.6, 11.0 (H-6'a); 3.75 dd, 1 H, J=2.2, 11.0 (H-6'b); 3.71 dd, 1 H, J=8.9, 9.7 (H-4'); 3.69 dd, 1 H, J=2.3, 10.7 (H-6a); 3.64 dd, 1 H, J=8.9, 11.0 (H-3); 3.64 s, 3 H (OCH$_2$CO$_2$CH$_3$); 3.57 dt, 1 H, J=2.1, 2.1, 10.0 (H-5); 3.50 dt, 1 H, J=8.4, 10.1, 10.1 (H-2'); 3.35 dd, 1 H, J=2.1, 10.7 (H-6b); 3.26 dt, 1 H, J=2.4, 2.4, 9.7 (H-5'); 3.08 bt, 1 H, J=9.6, 9.6 (H-3'); 2.00 s, 3 H (NHCOCH$_3$); the signal of NHCO$_2$CH$_2$CCl$_3$ was not observed. $^{13}$C NMR: 174.2 (OCH$_2$CO$_2$CH$_3$), 170.8 (NHCOCH$_3$), 154.0 (NHCO$_2$CH$_2$CCl$_3$), 138.2, 138.1, 138.0, 137.8, 137.7, 129.8, 129.0, 128.5, 128.4 (2C), 128.4, 128.3 (2C), 128.3 (5C), 127.9 (3C), 127.8 (3C), 127.7 (2C), 127.5 (4C) (C-arom.), 100.9 (C-1'), 96.7 (C-1), 94.9 (NHCO$_2$CH$_2$CCl$_3$), 82.3 (C-3'), 78.3 (C-4'), 78.0 (C-4), 77.3 (C-3), 74.9 (NHCO$_2$CH$_2$CCl$_3$), 74.9 (CH$_2$-Ph), 74.5 (CH$_2$-Ph), 74.2 (C-5'), 73.7 (CH$_2$-Ph), 73.3 (CH$_2$-Ph), 70.4 (CH$_2$-Ph), 69.6 (C-5), 69.2 (OCH$_2$CO$_2$CH$_3$), 68.6 (C-6'), 67.1 (C-6), 57.5 (C-2'), 54.3 (C-2), 51.7 (OCH$_2$CO$_2$CH$_3$), 23.1 (NHCOCH$_3$). For C$_{55}$H$_{61}$Cl$_3$N$_2$O$_{14}$ calculated: relative molecular mass 1 080.5, monoisotopic mass 1 078.3. FAB MS, m/z: 1 079.5, 1 081.5 [M+H]$^+$, 1 101.5, 1 103.5 [M+Na]$^+$. For C$_{55}$H$_{61}$Cl$_3$N$_2$O$_{14}$ (1 080.5) calculated: 61.14% C, 5.69% H, 9.84% Cl, 2.59% N; found: 60.90% C, 5.85% H, 9.92% Cl, 2.62% N.

Example 4

Preparation of N-L18-norAbu-GMDP

N-(2-O-{Benzyl 3,4,6-tri-O-benzyl-2-deoxy-2-[(2,2,2-trichloroethoxy)-carbonyl]amino-β-D-glucopyranosyl-(1→4)-2-acetamido-6-O-benzyl-2-deoxy-α-D-glucopyranosid-3-yl}-glycoloyl)-L-α-aminobutanoyl-D-isoglutaminyl benzyl ester (19)

A solution of tent-butoxycarbonyl-L-2-aminobutanoyl-D-isoglutamine benzyl ester[25] (632 mg, 1.5 mmol) in dichloromethane-trifluoroacetic acid (1:1, 28 ml) was kept at room temperature for 30 min and then the mixture was evaporated. The residue was co-evaporated with dichloromethane (3×15 ml) and dried at room temperature and 1.32 Pa for 6 h. The obtained syrup was dissolved in N,N-dimethylformamide (7 ml) and the resulting solution of L-2-aminobutanoyl-D-isoglutamine benzyl ester trifluoroacetate was used immediately for coupling with the acid 16.

To a stirred solution of acid 16 (1 440 mg, 1.35 mmol) and 1-hydroxybenzotriazole monohydrate (230 mg, 1.5 mmol) in dichloromethane-N,N-dimethylformamide (10:1, 14 ml) at 0° C., 1M solution of N,N'-dicyclohexylcarbodiimide in dichloromethane (1.5 ml, 1.5 mmol) was added and the stirring was continued for 1 h at 0° C. The above mentioned solution of L-2-aminobutanoyl-D-isoglutamine benzyl ester trifluoroacetate and ethyl(diisopropyl)amine (512 μl, 3.0 mmol) were added and the mixture was stirred for 1 h at 0° C. and kept overnight at room temperature. Then chloroform (150 ml) was added and N,N'-dicyclohexylurea was filtered off. The filtrate was extracted with saturated aqueous solution of sodium hydrogen carbonate (2×20 ml) and 5% aqueous sodium chloride (1×20 ml), dried (MgSO$_4$) and evaporated. Chromatography of the residue on a silica gel column (30 g) in chloroform-methanol (20:1) afforded 1 100 mg (60%) of solid compound 19; m.p. 190-196° C. (decomp.); [α]$_D$ +32° (c 1.4, chloroform). $^1$H NMR: 8.31 bd, 1H, J=6.5 (NH-Abu); 8.07 bd, 1H, J=9.2 (NH-iGln); 7.49 bd, 1H, J=7.3 (NH-COCH$_3$); 7.12-7.38 m, 25H (H-arom.) 5.07 s, 2H (COOCH$_2$-Ph); 4.79 d, 1H, J=12.4 (CH$_2$-Ph); 4.76 d, 1H, J=12.4 (CH$_2$-Ph); 4.72 s, 2H (NHCOOCH$_2$CCl$_3$); 4.65 d, 1H, J=11.9 (CH$_2$-Ph); 4.63 d, 1H, J=10.9 (CH$_2$-Ph); 4.62 d, 1H, J=12.4 (CH$_2$-Ph); 4.55 d, 1H, J=11.9 (CH$_2$-Ph); 4.50 d, 1H, J=12.4 (CH$_2$-Ph); 4.48 d, 1H, J=10.9 (CH$_2$-Ph); 4.46 d, 1H, J=12.4 (CH$_2$-Ph); 4.45 d, 1H, J=12.4 (CH$_2$-Ph); 4.40 d, 1H, J=15.7 (CH$_2$CO); 4.29 bq, 1H, J=6.8 (α-Abu); 4.25 dt, 1H, J=5.0, 8.7, 8.7 (α-iGln); 4.10 d, 1H, J=15.7 (CH$_2$CO); 3.57 dd, 1H, J=4.9, 11.1 (H'-6b); 2.36 t, 2H, J=7.9 (γ-iGln); 2.02 ddt, 1H, J=4.9, 8.5, 8.5, 13.8 (β-iGln); 1.84 s, 3H (NHCOCH$_3$); 1.78 dddd, 1H, J=5.0, 7.5, 9.0, 13.8 (β-iGln); 1.72 m, 1H (β-Abu);

1.53 m, 1H (β-Abu); 0.78 t, 3H, J=7.4 (γ-Abu). $^{13}$C NMR: 172.78 (OCH$_2$CO); 172.07 (Abu-CO); 170.02 (COOCH$_2$Ph); 169.96 (NHCOCH$_3$); 169.56 (iGln-CO); 136.12, 137.48, 138.05, 138.42, 138.51 (2C); 128.38 (3C); 128.21 (4C); 128.20 (2C); 128.19 (3C); 128.11, 127.94 (2C); 127.83 (2C); 127.70 (2C); 127.57, 127.54 (2C); 127.46 (2C); 127.31, 127.26, 127.21, 127.11, 127.05 (2C); 100.20 (C'-1); 96.20 (CCl$_3$); 95.82 (C-1); 81.77 (C-3); 78.28 (C-4); 77.92 (C'-3); 75.37 (C'-4); 74.42 (C'-5); 73.94 (CH$_2$-Ph); 73.86 (CH$_2$-Ph); 73.39 (COOCH$_2$CCl$_3$); 72.32 (CH$_2$-Ph); 71.88 (OCH$_2$CO); 70.39 (C'-6); 70.14 (C-5); 68.57 (C-6); 68.52 (CH$_2$-Ph); 67.96 (CH$_2$-Ph); 65.45 (CH$_2$-Ph); 57.57 (C'-2); 53.29 (iGln-CH); 52.61 (C-2); 51.39 (Abu-CH); 30.02 (iGln-CHCH$_2$CH$_2$); 27.04 (iGln-CHCH$_2$); 25.29 (Abu-CH$_2$); 22.53 (NHCOCH$_3$); 09.71 (Abu-CH$_3$). For C$_{70}$H$_{80}$N$_5$O$_{17}$Cl$_3$ calculated: relative molecular mass 1369.8, monoisotopic mass 1 367.5. FAB MS, m/z: 1 370.2 [M+H]$^+$, 1 392.2 [M+Na]$^+$. For C$_{70}$H$_{80}$N$_5$O$_{17}$Cl$_3$ (1 369.8) calculated: 61.38% C, 5.89% H, 7.76% Cl, 5.11% N; found: 61.25% C, 6.02% H, 7.58% Cl, 5.07% N.

N-[2-O-(Benzyl 2-amino-3,4,6-tri-O-benzyl-2-deoxy-β-D-glucopyranosyl-(1→4)-2-acetamido-6-O-benzyl-2,3-deoxy-α-D-glucopyranosid-3-yl)-glycoloyl]-L-α-aminobutanoyl-D-isoglutamine benzyl ester (20)

Zinc powder (1.13 g, 17 mmol) was added to a stirred solution of 19 (970 mg, 0.71 mmol) in acetic acid (21 ml) at room temperature, and the stirring was continued at the same temperature for 6 h. The insoluble material was filtrated of and the filtrate evaporated. The residue was dissolved in chloroform (150 ml) and the solution was washed with water (2×30 ml), dried (MgSO$_4$) and the solvent was evaporated. The residue was purified on a silica gel column (60 g) in chloroform—methanol (20:1), homogenous fractions were evaporated to give solid residue, which was lyophilized from benzene. Yield 667 mg (79%) of 20; [α]$_D$ +54° (c 0.3; chloroform). IR (chloroform): 3 476, 3 433, 3 336 (NH, NHAc); 3 090, 3 067, 3 032 (=C—H, Bn); 1 724 (C=O, NAc); 1 675 (amide I); 1 518 (amide II); 1 498, 1 454 (arom. ring). $^1$H NMR: 8.33 bd, 1H, J=7.3 (NHCOCH$_3$); 8.29 bd, 1H, J=7.2 (NH-Abu); 7.57 bd, 1H, J=8.5 (NH-iGln); 7.37-7.15 m, 30H (H-arom.); 5.06 s, 2H (COOCH$_2$Ph); 4.87 d, 1H, J=3.5 (H-1); 4.78 d, 1H, J=11.4 (CH$_2$-Ph); 4.74 d, 1H, J=11.4 (CH$_2$-Ph); 4.66 d, 1H, J=11.2 (CH$_2$-Ph); 4.64 d, 1H, J=12.3 (CH$_2$-Ph); 4.57 d, 1H, J=12.0 (CH$_2$-Ph); 4.52 d, 1H, J=12.0 (CH$_2$-Ph); 4.50 d, 1H, J=11.2 (CH$_2$-Ph); 4.49 d, 1H, J=12.1 (CH$_2$-Ph); 4.46 d, 1H, J=12.1 (CH$_2$-Ph); 4.44 d, 1H, J=12.3 (CH$_2$-Ph); 4.36 d, 1H, J=15.8 (CH$_2$CO); 4.29 bq, 1H, J=6.8 (α-Abu); 4.24 dt, 1H, J=4.9, 8.7, 8.7 (α-iGln); 4.21 d, 1H, J=7.9 (H-1'); 4.13 d, 1H, J=15.8 (CH$_2$CO); 3.94 dd, 1H, J=3.4, 11.0 (H-6a); 3.87 dd, 1H, J=8.9, 10.9 (H-4); 3.80 ddd, 1H, J=1.7, 3.4, 9.6 (H-5); 3.80 d, 1H, J=3.5, 7.3, 10.9 (H-2); 3.67 dd, 1H, J=1.7, 11.0 (H-6b); 3.64 dd, 1H, J=8.9, 10.9 (H-3); 3.56 dd, 1H, J=4.8, 11.2 (H-6a'); 3.44 dd, 1H, J=2.7, 11.2 (H-6b'); 3.44 dd, 1H, J=8.8, 9.6 (H-4'); 3.27 ddd, 1H, J=2.7, 4.8, 9.6 (H-5'); 3.27 dd, 1H, J=8.8, 9.8 (H-3'); 2.63 dd, 1H, J=7.9, 9.8 (H-2'); 2.35 t, 2H, J=7.9 (γ-iGln); 2.00 ddt, 1H, J=4.9, 8.6, 8.6, 13.8 (β-iGln); 1.84 s, 3H (NHCOCH$_3$); 1.76 dddd, 1H, J=5.0, 7.3, 9.2, 13.8 (β-iGln); 1.63 m, 1H ((β-Abu); 1.54 m, 1H (β-Abu); 0.77 t, 3H, J=7.4 (γ-Abu). $^{13}$C NMR: 172.77 (OCH$_2$CO); 172.03 (Abu-CO); 170.92 (COOCH$_2$Ph); 170.09 (NHCOCH$_3$); 169.49 (iGln-CO); 138.72; 138.45; 138.33; 138.15; 137.53; 136.10; 128.35 (3C); 128.22 (2C); 128.18 (2C); 128.17 (3C); 128.16 (3C); 128.09 (2C); 127.92 (2C); 127.80 (2C); 127.59 (2C); 127.54 (2C); 127.53; 127.51; 127.50 (2C); 127.49 (2C); 127.45 (2C); 127.37; 127.18; 103.10 (C'-1); 95.81 (C-1); 84.46 (C-3); 82.31 (C-4); 77.91 (C'-3); 75.75 (C'-4); 74.60 (C'-5); 73.89 (CH$_2$-Ph); 73.64 (CH$_2$-Ph); 72.36 (CH$_2$-Ph); 72.05 (OCH$_2$CO); 70.19 (C-5); 70.11 (C'-6); 68.71 (CH$_2$-Ph); 68.47 (C-6); 67.89 (CH$_2$-Ph); 65.43 (CH$_2$-Ph); 57.33 (C'-2); 53.37 (C-2); 52.79 (iGln-CH); 51.36 (Abu-CH); 30.00 (iGln-CHCH$_2$CH$_2$); 27.03 (iGln-CHCH$_2$); 25.60 (Abu-CH$_2$); 22.52 (NHCOCH$_3$); 09.75 (Abu-CH$_3$).

For C$_{67}$H$_{79}$N$_5$O$_{15}$ calculated: relative molecular mass 1194.4, monoisotopic mass 1193.6. FAB MS, m/z: 1194.0 [M+H]$^+$. For C$_{67}$H$_{79}$N$_5$O$_{15}$ (1194.4) calculated: 67.38% C, 6.67% H, 5.86% N; found: 67.22% C, 6.58% H, 5.73% N.

N-[2-O-(Benzyl 3,4,6-tri-O-benzyl-2-deoxy-2-stearoylamino-β-D-gluco-pyranosyl-(1→4)-2-acetamido-6-O-benzyl-2,3-dideoxy-α-D-glucopyranosid-3-yl)-glycoloyl]-L-α-aminobutanoyl-D-isoglutaminyl benzyl ester (21)

To a stirred solution of compound 20 (717 mg, 0.6 mmol) in DMF (8 ml), stearoylchloride (303 mg, 1 mmol) and diisopropylethylamine (0.174 ml, 1 mmol) were added. The mixture was stirred at 60° C. and the reaction was checked by TLC. After 5 h stirring at room temperature, methanol (0.3 ml) was added and the mixture was stirred for 1 h. Solvents were evaporated and the solid residue was extracted with petroleum ether (3×10 ml) to remove methyl stearate and then dissolved in chloroform (150 ml). The solution was washed with water (2×30 ml), dried (MgSO$_4$) and evaporated. Chromatography of the residue on a silica gel column (30 g) in chloroform-methanol (20:1) yielded 605 mg (69%) of solid product 21 (wherein R=stearoyl); [α]$_D$ +25° (c 0.3, chloroform); ref.$^{28}$: [α]$_D$ +25° (c 0.3, chloroform). IR (chloroform): 3 474, 3 428, 3 404, 3 338 (NH, NHAc); 3 090, 3 067, 3 033 (=C—H, Bn); 1 726 (CO=O); 1 677 (amide I); 1 515 (amide II); 1 498, 1 455 (arom. ring, Bn). $^1$H NMR and $^{13}$C NMR spectra correspond with the data for the authentic sample prepared by procedure described in ref.$^{28}$. For C$_{85}$H$_{113}$N$_5$O$_{16}$ calculated: relative molecular mass 1 460.9, monoisotopic mass 1 459.8. FAB MS, m/z: 1 461.3 [M+H]$^+$. For C$_{85}$H$_{113}$N$_5$O$_{16}$ (1 460.9) calculated: 69.89% C, 7.80% H, 4.79% N; found: 70.08% C, 7.86% H, 4.58% N.

N-[2-O-(2-deoxy-2-stearoylamino-β-D-glucopyranosyl-(1→4)-2-acetamido-2,3-dideoxy-α-D-glucopyranosid-3-yl)-glycoloyl]-L-α-aminobutanoyl-D-isoglutamine (23; N-L18-norAbu-GMDP)

For the hydrogenolyzis of O-benzyl groups of compound 21, the procedure described in our paper$^{28}$ was employed. Compound 21 (731 mg, 0.5 mmol) was hydrogenolyzed in acetic acid (45 ml) over 5% Palladium catalyst on carbon (1.5 g) at room temperature for 15 h. After this time the vessel was flushed with argon, the catalyst was filtered off and washed with acetic acid (75 ml). The filtrate was taken down and the residue purified on a silica gel C18 column in methanol-water (4:1). The homogenous fraction was evaporated and the residue and was lyophilized from acetic acid, to give 345 mg (75%) of compound 21, N-L18-norAbu-GMDP, [α]$_D$ +25° (c 0.4, chloroform). $^1$H NMR and $^{13}$C NMR spectra agree with the date for the authentic sample prepared by procedure described in ref.$^{28}$. For C$_{43}$H$_{77}$N$_5$O$_{16}$ calculated: relative molecular mass 920.1. monoisotopic mass 919.54. FAB MS, m/z: 943.1 [M+Na]$^+$. HR MS, m/z: for C$_{43}$H$_{77}$O$_{16}$N$_5$Na=942.52575 found 942.52516 [Fragmentation: C$_{19}$H$_{32}$O$_{11}$N$_4$Na=515.19598 found 515.19617;

$C_{32}H_{58}O_{10}N_2Na$=653.39837 found 653.39863; $C_{11}H_{19}O_6N_3Na$=312.11661 found 312.11683]

Example 5

Preparation of N-B30-norAbu-GMDP

N-{2-O-[Benzyl 3,4,6-tri-O-benzyl-2-deoxy-2-(2-tetradecylhexadecanoyl-amino)-β-D-glucopyranosyl-(1→4)-2-acetamido-6-O-benzyl-2,3-dideoxy-α-D-gluco-pyranosid-3-yl]-glycoloyl}-L-α-aminobutanoyl-D-isoglutaminyl benzyl ester (22)

To a stirred solution of compound 20 (450 mg, 0.38 mmol) in DMF (8 ml), 2-tetradecylhexadecanoyl chloride (194 mg, 0.41 mmol) and diisopropyl-ethylamine (0.71 ml, 0.41 mmol) were added. The mixture was stirred at 60° C. and the reaction was checked by TLC. After 10 h stirring, methanol (0.3 ml) was added and the mixture was stirred for 1 h at room temperature. Solvents were evaporated and the solid residue was extracted with petroleum ether (3×10 ml) to remove methyl 2-tetradecyl-hexadecanoate and then dissolved in chloroform (150 ml). The solution was washed with water (2×30 ml), dried (MgSO$_4$) and evaporated. Chromatography of the residue on a silica gel column (30 g) in chloroform-methanol (20:1) yielded, 619 mg (70.6%) of solid product 22 (wherein R=2-tetradecylhexadecanoyl); $[\alpha]_D$ +25° (c 0.2, chloroform). $^1$H NMR: 7.42-7.22 m, 30H (H-arom.); 7.08 bd, 1H, J=6.6 (NH-Abu); 7.05 bd, 1H, J=8.4 (NH-iGln); 6.19 bd, 1H, J=8.5 (NHCOCH$_3$); 5.09 s, 2H (COOCH$_2$Ph); 4.93 d, 1H, J=3.9 (H-1); 4.79 d, 1H, J=11.5 (CH$_2$-Ph); 4.76 d, 1H, J=12.0 (CH$_2$-Ph); 4.65 d, 1H, J=8.2 (H-1'); 4.65 d, 1H, J=12.0 (CH$_2$-Ph); 4.65 d, 1H, J=11.0 (CH$_2$-Ph); 4.64 d, 1H, J=11.5 (CH$_2$-Ph); 4.53 d, 1H, J=12.0 (CH$_2$-Ph); 4.51 d, 1H, J=11.0 (CH$_2$-Ph); 4.50 d, 1H, J=12.0 (CH$_2$-Ph); 4.49 d, 1H, J=12.0 (CH$_2$-Ph); 4.48 d, 1H, J=12.0 (CH$_2$-Ph); 4.37 ddd, 1H, J=4.9, 8.4, 8.8 (α-iGln); 4.43 d, 1H, J=15.6 (CH$_2$CO); 4.17 d, 1H, J=15.5 (CH$_2$CO); 4.20 ddd, 1H, J=3.9, 8.5, 10.4 (H-2); 4.09 t, 1H, J=9.5 (H-4); 3.96 bq, 1H, J=7.0 (α-Abu); 3.73 dd, 1H, J=2.8, 10.7 (H-6a); 3.70 dt, 1H, J=2.4, 2.4, 9.8 (H-5); 3.69-3.63 m, 3H (H-2', H-3'), H-4'); 3.67 dd, 1H, J=2.6, 10.9 (H-6'a); 3.63 dd, 1H, J=4.3, 10.9 (H-6'b); 3.56 dd, 1H, J=9.0, 10.4 (H-3); 3.52 dd, 1H, J=2.0, 10.7 (H-6b); 3.39 ddd, 1H, J=2.6, 4.3, 9.0 (H-5'); 2.50 dt, 1H, J=7.3, 7.3, 17.1 (γ-iGln); 2.39 dt, 1H, J=6.7, 6.7, 17.1 (γ-iGln); 2.18 dddd, 1H, J=4.9, 6.7, 7.3, 14.6 (β-iGln); 2.01 s, 3H (NHCOCH$_3$); 1.98 dddd, 1H, J=6.7, 7.3, 8.4, 14.6 (β-iGln); 1.83 m, 1H (β-Abu); 1.78 m, 1H {NHCOCH[(CH$_2$)$_{13}$CH$_3$]$_2$}1.67 m, 1H (β-Abu); 0.88 t, 6H, J=6.9 {NHCOCH[(CH$_2$)$_{13}$CH$_3$]$_2$}; 0.84 t, 3H, J=7.4 (γ-Abu). $^{13}$C NMR: 173.47 s (OCH$_2$CO); 173.21 s (Abu-CO); 171.66 s (iGln-CO); 171.57 s (COOCH$_2$Ph); 170.31 s (NHCOCH$_3$); 138.30 s (CH$_2$-Ph); 138.03 s (CH$_2$-Ph); 137.97 s (CH$_2$-Ph); 136.70 s (CH$_2$-Ph); 135.69 s (CH$_2$-Ph); 99.59 d (C-1'); 96.44 d (C-1); 81.07 d (C-3'); 80.27 d (C-3); 78.17 d (C-4'); 74.87 d (C-5'); 74.31 t (CH$_2$-Ph); 74.26 d (C-4); 73.61 t (CH$_2$-Ph); 73.49 t (CH$_2$-Ph); 73.12 t (CH$_2$-Ph); 70.46 d (C-5); 70.34 t (OCH$_2$CO); 69.66 t (CH$_2$-Ph); 68.78 t (C-6'); 67.92 t (C-6); 66.57 t (CH$_2$-Ph); 55.74 d (C-2'); 55.74 d (Abu-CH); 52.69 d (iGln-CH); 52.35 d (C-2); 47.96 d {NHCOCH[(CH$_2$)$_{13}$CH$_3$]$_2$}; 32.67 t {NHCOCH[(CH$_2$)$_{13}$CH$_3$]$_2$}; 32.41 t {NHCOCH[(CH$_2$)$_{13}$CH$_3$]$_2$}; 31.92 t (2C); 30.77 t (iGln-CHCH$_2$CH$_2$); 29.81 t {NHCOCH[(CH$_2$)$_{13}$CH$_3$]$_2$}; 29.35 t {NHCOCH[(CH$_2$)$_{13}$CH$_3$]$_2$}; 27.81 t {NHCOCH[(CH$_2$)$_{13}$CH$_3$]$_2$}; 27.67 t {NHCOCH[(CH$_2$)$_{13}$CH$_3$]$_2$}; 26.09 t (iGln-CHCH$_2$CH$_2$); 24.28 t (Abu-CH$_2$); 23.37 q (NHCOCH$_3$); 22.68 q (2C); 14.10 q {NHCOCH[(CH$_2$)$_{13}$CH$_3$]$_2$}; 10.39 q (Abu-CH$_3$). For $C_{97}H_{137}N_5O_{16}$ calculated: relative molecular mass 1 629.15, monoisotopic mass 1 628.01. FAB MS, m/z: 1 630.3 [M+H]$^+$. HR MS, m/z: for $C_{97}H_{137}O_{16}N_5Na$=1650.99526 found 1650.99497 [Fragmentation: $C_{40}H_{50}O_{11}N_4Na$=785.33683 found 785.33673; $C_{84}H_{121}O_{12}N_3Na$=1386.88425 found 1386.88409; $C_{27}H_{34}O_7N_2Na$=521.22582 found 521.22569]

N-{2-O-[2-deoxy-2-(2-tetradecyl-hexadecanoylamino)-β-D-gluco-pyranosyl-(1→4)-2-acetamido-2,3-dideoxy-α-D-glucopyranosid-3-yl]glycoloyl}-L-α-aminobutanoyl-D-isoglutamine (24; N-B30-norAbu-GMDP)

Compound 22 (815 mg, 0.5 mmol) was hydrogenolyzed in acetic acid (45 ml) over 5% palladium catalyst on carbon (1.5 g) at room temperature for 15 h. After this time the vessel was flushed with argon, the catalyst was filtered off and washed with acetic acid (75 ml). The filtrate was taken down and the residue purified on a silica gel C18 column in methanol-water (9:1). The homogenous fraction was evaporated and the residue was lyophilized from acetic acid, to give 376 mg (69%) of compound 24, N-B30-norAbu-GMDP. For $C_{55}H_{101}N_5O_{16}$ calculated: relative molecular mass 1088.41, monoisotopic mass 1087.72. FAB MS, m/z: 1110.8 [M+Na]. HR MS, m/z: for $C_{55}H_{101}O_{16}N_5Na$=1110.71355 found 1110.71293 [Fragmentation: $C_{44}H_{82}O_{10}N_2Na$=821.58617 found 821.58677; $C_{19}H_{32}O_{11}N_4Na$=515.19598 found 515.19621; $C_{11}H_{19}O_6N_3Na$=312.11661 found 312.11692]

Example 6

Preparation of norAbu-MDP-Lvs-L18

Synthesis of 2-chlorotritylchloride resin-bonded peptide (25)

Fmoc-L-Lys(Dde)-OH and 2-chlorotritylchloride resin were dried in vacuo over KOH for 24 h. To a solution of Fmoc-L-Lys(Dde)-OH (0.85 g, 1.6 mmol) in dry DCM (20 ml) the resin (2 g, 1.6 mmol), DIEA (0.231 ml, 1.35 mmol) were added and the mixture was stirred at room temperature for 5 min, then the another portion of DIEA (0.461 ml, 2.7 mmol) was added and the stirring was continued for another 1 h. Methanol (1.6 ml) was added and the mixture was stirred for 10 min at room temperature. The resin was washed with DCM (3×20 ml), DMF (2×20 ml), MeOH (2×20 ml) and diethylether (2×20 ml) and dried in vacuo over KOH for 24 h. The substitution of the resin was determinate photometrically (0.56 mmol/g) and by amino acid analysis (0.33 mmol/g). In the following calculation the substitution 0.56 mmol/g was used.

The Fmoc protecting group was split off from the product by treating with 5% solution of piperidine in DMF-DCM (1:1) for 5 min at room temperature and subsequently by treating with 20% solution of piperidine in DMF for 20 min at the same temperature. The resin was washed with DMF (8×10 ml) and the solution of Fmoc-D-iGln-OH (1.77 g, 4.8 mmol), HOBt (0.74 g, 2.43 mmol), HBTU (1.79 g, 4.8 mmol) and DIEA (1.64 ml, 9.6 mmol) in DMF (5 ml) was added and the whole was stirred for 90 min at room temperature. The reaction course was followed by Kaiser ninhydrin test. The end amino acid (Fmoc-L-α-Abu-OH) was coupled by the analogous procedure; the Fmoc group was split off by treatment with 5% solution of piperidine in DMF-DCM (1:1) for 25 min., the resin was washed with DMF (5×20 ml), the solution of amino acid (1.57 g, 4.8 mmol), HBTU (1.79 g, 4.8 mmol) and DIEA (1.64 ml, 9.6 mmol) in DMF (5 ml) was added and the whole was stirred at room temperature for 1 h. The resin-bonded peptide 25 was obtained by removing of the N-terminal Fmoc group by action of 20% solution of piperidine in DMF for 20 min at room temperature. The product was characterized by amino acid analysis.

The perbenzylated normuramic acid 9 prepared in Example 2 was condensed with the resin-bonded peptide 25 (washed with DMF) by using the "swelling volume" method. The mixture of the resin-bonded peptide 25, normuramic acid 9 (0.49 g, 0.9 mmol), HBTU (0.33 g, 0.89 mmol) and DIEA (0.307 ml, 1.8 mmol) in DMF (6 ml) was stirred at room temperature for 20 h. Because the Kaiser ninhydrin test was positive, the resin was filtered off and the condensation step was repeated with the same amounts of reagents. Kaiser ninhydrin test was negative after another 6 h. Then the resin was washed with DMF (5×10 ml), to afford resin-bonded peptide glycopeptide 26.

The Dde group from the obtained wet resin-bonded peptide glycopeptide 26 was split off by action of the solution of 2% of hydrazine hydrate in DMF for 10 min at room temperature, and then the resin was washed with DMF (8×10 ml), to give the wet resin-bonded peptide glycopeptide 27.

A solution of stearic acid (0.43 g, 1.5 mmol), HBTU (0.54 g, 1.45 mmol) and DIEA (0.51 ml, 3.00 mmol) in DMF (5 ml) was added to the wet resin-bonded peptide glycopeptide 27 and the whole was stirred at room temperature for 6 h. The reaction course was followed by Kaiser ninhydrin test. The resin was washed with DCM (3×10 ml), DMF (2×10 ml), EtOH (2×20 ml), MeOH (2×10 ml), diethylether (2×10 ml) and dried in vacuo over KOH for 24 h. Yield 1.24 g (70%) of resin-bonded lipoglycopeptide 28.

N-[2-O-(Benzyl 2-acetamido-4,6-di-O-benzyl-2,3-dideoxy-α-D-gluco-pyranosid-3-yl)-glycoloyl]-L-α-aminobutanoyl-D-isoglutaminyl-L-lysine(stearoyl) (30)

The product 30 was split off from the resin by treating of the resin-bonded lipoglycopeptide 28 with a mixture AcOH-TFE-DCM (1:1:8; 60 ml) for 1h at room temperature. Then the resin was filtered off, the filtrate was concentrated in vacuo and the residue was lyophilized from benzene, to give 774 mg (65%) crude product 30. Its chromatography on a silica gel C-18 column in linear gradient of methanol in water (80%→100%) followed by lyophilization from acetic acid afforded 313 mg (35%) of compound 30; mp 204-206° C. [$\alpha_D$ ]+48° (c 0.3; DMF). $^1$H NMR spectrum: 8.29 d, 1 H, J=8.2 [NHCH(CONH$_2$)]; 8.25 d, 1 H, J=80 (NHCH$_3$); 8.05 d, 1 H, J=8.0 [NHCH(CH$_2$CH$_3$)CO];7.72 t, 1 H, J=5.5 (NHCOCH$_2$C$_{15}$H$_{30}$CH$_3$); 7.55 bd, 1 H, J=7.7 [NHCH(COOH)]; 4.82 d, 1 H, J=3.5 (C-1); 4.70 d, 2 H, J=11.0 (CH$_2$-Ph); 4.65 d, 2 H, J=12.3 (CH$_2$-Ph); 4.55 d, 2 H, J=12.1 (CH$_2$-Ph); 4.52 d, 2 H, J=11.0 (CH$_2$-Ph); 4.50 d, 2 H, J=12.1 (CH$_2$-Ph); 4.46 d, 2 H, J=12.3 (CH$_2$-Ph); 4.29 ddd, 1 H, J=6.1, 7.3, 7.3 [CH(COOH)]; 4.18 d, 2 H, J=15.0 [O(CH$_2$)CO]; 4.16 ddd, 1 H, J=5.6, 8.2, 8.8 [NHCH(CONH$_2$)]; 4.14 d, 2 H, J=15.0 [O(CH$_2$)CO]; 4.09 ddd, 1 H, J=5.2, 8.0, 9.0 [NHCH(CH$_2$CH$_3$)CO] 3.89 ddd, 1 H, J=3.5, 8.0, 10.7 (C-2); 3.71 ddd, 1 H, J=1.7, 4.1, 10.0 (C-5); 3.67 dd, 2 H, J=4.1, 10.6 (C-6); 3.67 dd, 1 H, J=8.9, 10.7 (C-3); 3.61 dd, 2 H, J=1.7, 10.6 (C-6); 3.58 dd, 1 H, J=8.9, 9.9 (C-4); 2.98 bq, 2 H, J=7.1 (CH$_2$CH$_2$CH$_2$CH$_2$NH); 2.13 m, 2 H, (CH$_2$CH$_2$CO); 2.01 t, 2 H, J=7.4 (COCH$_2$C$_{15}$H$_{30}$CH$_3$); 1.91 m, 2 H (CH$_2$CH$_2$CO); 1.83 s, 3 H (NHCH$_3$); 1.70 m, 2 H (CH$_2$CH$_2$CO); 1.65 m, 2 H [NHCH(CH$_2$CH$_3$)CO]; 1.65 m, 2 H (CH$_2$CH$_2$CH$_2$CH$_2$NH); 1.53 m, 2 H [NHCH(CH$_2$CH$_3$)CO]; 1.53 m, 2 H (CH$_2$CH$_2$CH$_2$CH$_2$NH); 1.45 m, 2 H (COCH$_2$C15H$_{30}$CH$_3$); 1.35 m, 2 H (CH$_2$CH$_2$CH$_2$CH$_2$NH); 1.09-1.23 m, 30 H (COCH$_2$C15H$_{30}$CH$_3$); 1.09-1.23 m, 2 H (CH$_2$CH$_2$CH$_2$CH$_2$NH); 0.85 t, 3 H, J=7.5 [NHCH(CH$_2$CH$_3$)CO]; 0.79 t, 3 H, J=7.3 (COCH$_2$C15H$_{30}$CH$_3$). $^{13}$C NMR spectrum: 173.74 s [O(CH$_2$)CO]; 173.08 s [NHCH(CH$_2$CH$_3$)CO]; 171.85 s (CH$_2$CH$_2$CO); 171.55 s [CH(COOH)]; 170.89 s (NHCOCH$_2$C$_{15}$H$_{30}$CH$_3$); 169.02 s [CH(CONH$_2$)]; 138.18 s (CH$_2$-Ph); 138.00 s (CH$_2$-Ph); 137.52 s (CH$_2$-Ph); 128.23 d (CH$_2$-Ph); 128.22 d (CH$_2$-Ph); 127.77 d (CH$_2$-Ph); 127.65 d (CH$_2$-Ph); 127.55 d (CH$_2$-Ph); 127.50 d (CH$_2$-Ph); 127.41 d (CH$_2$-Ph); 127.17 d (CH$_2$-Ph); 96.04 d (C-1); 9.81 q [NHCH(CH$_2$CH$_3$)CO]; 79.97 d (C-3); 78.12 d (C-4); 73.93 t (CH$_2$-Ph); 72.33 t (CH$_2$-Ph); 70.97 t [O(CH$_2$)CO]; 70.42 d (C-5); 68.45 t (C-6); 68.41 t (CH$_2$-Ph); 53.20 d [CH(COOH)]; 52.81 d (C-2); 52.13 d [CH(CONH$_2$)]; 51.58 d [NHCH(CH$_2$CH$_3$)CO]; 38.12 t (CH$_2$CH$_2$CH$_2$CH$_2$NH); 35.39 t (NHCOCH$_2$C$_{15}$H$_{30}$CH$_3$); 31.24 t (CH$_2$CH$_2$CO); 28.98 t (NHCOCH$_2$C$_{15}$H$_{30}$CH$_3$); 28.97 t (NHCOCH$_2$C$_{15}$H$_{30}$CH$_3$); 28.94 t (NHCOCH$_2$C$_{15}$H$_{30}$CH$_3$); 28.89 t (NHCOCH$_2$C$_{15}$H$_{30}$CH$_3$); 28.79 t (NHCOCH$_2$C$_{15}$H$_{30}$CH$_3$); 28.72 t (NHCOCH$_2$C$_{15}$H$_{30}$CH$_3$); 28.64 t (CH$_2$CH$_2$CH$_2$CH$_2$NH); 28.63 t (NHCOCH$_2$C$_{15}$H$_{30}$CH$_3$); 28.04 t (NHCOCH$_2$C$_{15}$H$_{30}$CH$_3$); 27.90 t (CH$_2$CH$_2$CO); 25.62 t [NHCH(CH$_2$CH$_3$)CO]; 25.26 t (CH$_2$CH$_2$CH$_2$CH$_2$NH); 22.91 t (CH$_2$CH$_2$CH$_2$CH$_2$NH); 22.48 q (NHCH$_3$); 13.90 q (NHCOCH$_2$C$_{15}$H$_{30}$CH$_3$). For C$_{64}$H$_{96}$ N$_6$O$_{13}$ calculated: relative molecular weight 1157.5 monoisotopic weight 1156.7. FAB-MS (T+G, DMF), m/z 1157 [M+H]$^+$ and 1179 [M+Na]$^+$. HR MS, m/z: for C$_{64}$H$_{96}$O$_{13}$N$_6$Na=1179.69276 found 1179.69274 [Fragmentation: C$_{34}$H$_{40}$O$_7$N$_2$Na= 611.27277 found 611.27308; C$_{57}$H$_{88}$O$_{12}$N$_6$Na=1071.63524 found 1071.63627; C$_{40}$H$_{48}$O$_{10}$N$_4$Na=767.32627 found 767.32705].

N-[2-O-(2-Acetamido-2,3-dideoxy-α-D-glucopyranosid-3-yl)-glycoloyl]-L-α-aminobutanoyl-D-isoglutaminyl-L-lysine(stearoyl) (32; norAbu-MDP-Lys-L18)

Compound 30 (0.261 g, 0.23 mmol) was hydrogenolyzed in acetic acid (80 ml) on 5% Pd/C catalyst (0.25 g) at room temperature for 24 h. The reaction course was followed by HPLC by using the conditions given in Example 6. The vessel was flushed with argon, the catalyst was filtered off, washed with acetic acid (3×30 ml), and the filtrate was lyophilized; yield of the crude product 0.155 g (77%). Chromatography of the lyophilizate on a silica gel C-18 column in linear gradient of water -methanol (75%→100%) followed by lyophilization of homogenous fractions from acetic acid gave 80 mg (39%, calculated as monohydrate) of the compound 32 norAbu-MDP-Lys-L18; [$\alpha$]$_D$ +24° (c 0.4; DMF). $^1$H NMR spectrum: 8.05 bd, 1 H, J=8.0 [NHCH(CONH$_2$)]; 8.02 bd, 1 H, J=8.7 (NHCH$_3$); 7.68 bd, 1 H, J=8.0 [NHCH(CH$_2$CH$_3$)CO]; 7.28 bd, 1 H, J=7.7 [NHCH(COOH)]; 7.03 bd, 1 H, J=6.0 (NHCOCH$_2$C$_{15}$H$_{30}$CH$_3$); 4.91 d, 1 H, J=3.6 (C-1); 4.46 d, 2 H, J=12.3 (CH$_2$-Ph); 4.20 d, 2 H, J=15.0 [O(CH$_2$)CO]; 4.08-4.14 m, 1 H [NHCH(CONH$_2$)]; 4.08-4.14 m [NHCH(CH$_2$CH$_3$)CO] 4.08 d, 2 H, J=15.9 [O(CH$_2$)CO]; 3.74 ddd, 1 H, J=3.6, 8.7, 10.4 (C-2); 3.63 ddd, 1 H, J=1.7, 5.4, 10.0 (C-5); 3.60 dd, 2 H, J=1.7, 10.0 (C-6); 3.51 dd, 2 H, J=5.4, 10.0 (C-6); 3.49 dd, 1 H, J=8.9, 10.4 (C-3); 3.33 bt, 1 H, J=9.6 (C-4); 2.99 bq, 2 H, J=6.9 (CH$_2$CH$_2$CH$_2$CH$_2$NH); 2.14 m, 4 H (CH$_2$CH$_2$CO); 2.01 t, 2 H, J=7.3 (COCH$_2$C$_{15}$H$_{30}$CH$_3$); 1.91 s, 3 H (NHCH$_3$); 1.69 m, 2 H [NHCH(CH$_2$CH$_3$)CO]; 1.69 m, 2 H (CH$_2$CH$_2$CH$_2$CH$_2$NH); 1.57 m, 2 H [NHCH(CH$_2$CH$_3$)CO]; 1.57 m, 2 H (CH$_2$CH$_2$CH$_2$CH$_2$NH); 1.36 m, 2 H (CH$_2$CH$_2$CH$_2$CH$_2$NH); 1.17-1.30 m, 30 H (COCH$_2$C15H$_{30}$CH$_3$); 1.17-1.30 m, 2 H (CH$_2$CH$_2$CH$_2$CH$_2$NH); 0.85 t, 3 H, J=7.3 (COCH$_2$C15H$_{30}$CH$_3$); 0.84 t, 3 H, J=7.5 [NHCH(CH$_2$CH$_3$) CO]. $^{13}$C NMR spectrum: 173.82 s [O(CH$_2$)CO]; 173.24 s [NHCH(CH$_2$CH$_3$)CO]; 171.90 s (CH$_2$CH$_2$CO); 171.64 s [CH(COOH)]; 171.24 s (NHCOCH$_2$C$_{15}$H$_{30}$CH$_3$); 169.29 s [CH(CONH$_2$)]; 90.76 d (C-1); 80.79 d (C-3); 72.16 d (C-5); 70.54 t [O(CH$_2$)CO]; 69.92 d (C-4); 60.71 t (C-6); 53.80 d [CH(COOH)]; 53.37 d (C-2); 52.22 d [CH(CONH$_2$)]; 51.89 d [NHCH(CH$_2$CH$_3$)CO]; 38.15 t (CH$_2$CH$_2$CH$_2$CH$_2$NH); 35.41 t (NHCOCH$_2$C$_{15}$H$_{30}$CH$_3$); 31.27 t (CH$_2$CH$_2$CO); 29.02 t (NHCOCH$_2$C$_{15}$H$_{30}$CH$_3$); 29.01 t (NHCOCH$_2$C$_{15}$H$_{30}$CH$_3$); 29.00 t (NHCOCH$_2$C$_{15}$H$_{30}$CH$_3$); 28.98 t (NHCOCH$_2$C$_{15}$H$_{30}$CH$_3$); 28.92 t (NHCOCH$_2$C$_{15}$H$_{30}$CH$_3$); 28.82 t (NHCOCH$_2$C$_{15}$H$_{30}$CH$_3$); 28.76 t (CH$_2$CH$_2$CH$_2$CH$_2$NH); 28.68 t (CH$_2$CH$_2$CH$_2$CH$_2$NH); 28.66 t (NHCOCH$_2$C$_{15}$H$_{30}$CH$_3$); 28.66 d (CH$_2$CH$_2$CO); 28.07 t (NHCOCH$_2$C$_{15}$H$_{30}$CH$_3$); 25.29 t [NHCH(CH$_2$CH$_3$)CO]; 25.10 t (CH$_2$CH$_2$CH$_2$CH$_2$NH); 22.61 s (NHCH$_3$); 13.94 q (NHCOCH$_2$C$_{15}$H$_{30}$CH$_3$); 10.12 q [NHCH(CH$_2$CH$_3$)CO]. For C$_{43}$H$_{78}$N$_6$O$_{13}$ calculated: relative molecular mass 887.1, monoisotopic mass 886.6. FAB-MS (DS, chloroform), m/z: 887.5 [M+N]$^{30}$, 909.5 [M+Na]$^+$. HR MS, m/z: for C$_{43}$H$_{78}$O$_{13}$N$_6$Na=909.55191 found 909.55125 Fragmentation: C$_{35}$H$_{65}$O$_8$N$_5$Na=706.47254 found 706.47250; C$_{19}$H$_{30}$O$_{10}$N$_4$Na=497.18541 found 497.18547; C$_{14}$H$_{25}$O$_8$N$_3$Na=386.15339 found 386.15357].

Example 7

Preparation of norAbu-MDP-Lys-B30

A solution of 2-tetradecylhexadecanoyl acid (0.73 g, 1.6 mmol), HBTU (0.54 g, 1.45 mmol) and DIEA (0.51 ml, 3.00 mmol) in DMF (5 ml) was added to the resin-bonded glycopeptide 27 prepared in Example 6 and the whole was stirred at room temperature. After 6 h (the reaction course was followed by Kaiser ninhydrin test) and the reaction mixture was worked up by using the same procedure as given above for compound 28, to afford 1.559 g (87%) of resin-bound lipoglycopeptide 29.

N-[2-O-(Benzyl 2-acetamido-4,6-di-O-benzyl-2,3-dideoxy-α-D-gluco-pyranosid-3-yl)-glycoloyl]-L-α-aminobutanoyl-D-isoglutaminyl-L-lysine(2-tetradecylhexadecanoyl) (31)

The product 31 was split off from the resin by treating the resin-bound lipoglycopeptide 29 by using the same procedure as given in Example 6 for product 30, to afford 365 mg of crude product 31 TLC in MeOH—CHCl$_3$—HCOOH (100:100:1) showed the presence of some impurity. Chromatography of the lyophilizate on a silica gel C-18 column in linear gradient of water-methanol (90%→100%) followed by lyophilization of homogenous fractions from acetic acid gave 146 mg (33%) of the compound 31. [α]$_D$ +7° (c 0.2; AcOH). $^1$H NMR spectrum: 4.95 d, 1H, J=3.5 (H-1); 4.45 m, 1H (α-iGln); 4.35 d, 1H, J=15.8 (OCH$_2$CO); 4.32 m, 1H (α-Lys); 4.22 m, 1H (α-Abu); 4.25 d, 1H, J=15.8 (OCH$_2$CO); 4.18 dd, 1H, J=3.5, 10.5 (H-2); 3.96-3.91 m, 2H (H-6); 3.81 dd, 1H, J=9.0, 9.8 (H-4); 3.69 dd, 1H, J=9.0, 10.5 (H-3); 3.69 ddd, 1H, J=2.2, 4.3, 9.8 (H-5); 3.33 m, 2H (ε-Lys); 3.22 m, (H-18'); 2.42 t, 2H, J=7.3 (γ-iGln); 2.10-2.03 m, 2H (β-iGln); 1.90-1.70 m, 6H (β-Lys, γ-Lys, δ-Lys); 1.80-1.50 m, 2H (β-Abu); 1.49-1.17 m, 52H {NHCOCH[CH$_2$)$_{13}$CH$_3$]$_2$}; 0.89 t, 6H, J=7.4 {NHCOCH[(CH$_2$)$_{13}$CH$_3$]$_2$}; 0.86 t, 3H, J=7.4 (γ-Abu). $^{13}$C NMR spectrum: 97.23 d (C-1); 79.10 d (C-3); 71.83 d (C-5); 71.60 d (C-4); 71.60 t (OCH$_2$CO); 64.43 t (C-6); 55.71 d (Abu-CH); 54.13 d (Lys-CH); 53.64 d (C-2); 53.54 d (iGln-CH); 39.83 t (Lys-CHCH$_2$CH$_2$CH$_2$CH$_2$); 33.41 t (Lys-CHCH$_2$CH$_2$CH$_2$CH$_2$); 31.08 {NHCOCH [CH$_2$)$_{13}$ CH$_3$]$_2$}; 30.37-29.46 t {NHCOCH[CH$_2$)$_{13}$CH$_3$]$_2$}; 29.60 t (iGln-CHCH$_2$CH$_2$); 25.92 t (Lys-CHCH$_2$CH$_2$CH$_2$CH$_2$); 25.42 t (iGln-CHCH$_2$); 23.66 t (Abu-CH$_2$); 22.63 t (Lys-CHCH$_2$CH$_2$CH$_2$CH$_2$); 14.21 q {NHCOCH[CH$_2$)$_{13}$CH$_3$]$_2$}; 10.38 q (Abu-CH$_3$). For C$_{76}$H$_{120}$N$_6$O$_{13}$ calculated: relative molecular weight 1325.8 monoisotopic weight 1324.9. FAB-MS (T+G, DMF), m/z 1347.8 [M+Na]$^+$. HR MS, m/z: for C$_{76}$H$_{121}$O$_{13}$N$_6$=1325.89862 found 1325.90045 [Fragmentation: C$_{34}$H$_{40}$O$_7$N$_2$Na=611.27277 found 611.27268; C$_{69}$H$_{112}$O$_{12}$N$_6$Na=1239.82305 found 1239.82340; C$_{47}$H$_{89}$O$_8$N$_5$Na=874.66034 found 874.66024]

N-[2-O-(2-Acetamido-2,3-dideoxy-α-D-glucopyranosid-3-yl)-glycoloyl]-L-α-aminobutanoyl-D-isoglutaminyl-L-lysine(2-tetradecylhexadecanoyl) (33; norAbu-MDP-Lys-B30)

Compound 31 was hydrogenolyzed in acetic acid on 5% Pd/C catalyst at room temperature for 24 h. The reaction course was followed by HPLC by using the conditions given in Example 6. The vessel was flushed with argon, the catalyst was filtered off, washed with acetic acid and the filtrate was lyophilized. Chromatography of the lyophilizate on a silica gel C-18 column in linear gradient of water -methanol (80%→100%) followed by lyophilization of homogenous fractions from acetic acid gave 35% of the compound 33 norAbu-MDP-Lys-B30. HR MS, m/z: for C$_{55}$H$_{102}$O$_{13}$N$_6$Na=1077.73971 found 1077.73942 [Fragmentation: C$_{47}$H$_{89}$O$_8$N$_5$Na=874.66034 found 874.66004; C$_{19}$H$_{30}$O$_{10}$N$_4$Na=497.18541 found 497.18522; C$_{36}$H$_{72}$O$_3$N$_2$Na=603.54352 found 603.54323]

Example 8

Preparation of norAbu-GMDP-Lys-L18

The perbenzylated glucosaminylnormuramic acid 15 prepared in Example 3 was coupled with 2-chlorotritylchloride resin—bonded peptide 25 by using the same procedure as described in Example 6. The resin-bound peptide, 25 glucosaminylnormuramic acid 15 (0.5 g; 0.546 mmol), HBTU (0.197 g; 0.52 mmol) and DIEA (0.188 ml, 1.092 mmol) in DMF (3 ml) was stirred at room temperature for 3.5 hours and then the catalytic amount of DMAP was added and the stirring was continued for another 1 h. The coupling course was followed by Kaiser ninhydrin test. Then the resin—bonded glycopeptide 34 was washed by DMF (5×10 ml).

The Dde group from the obtained wet resin-bonded glycopeptide 34 was split off by using the same procedure as give in Example 6., to afford wet resin-bonded peptide 35.

A solution of stearic acid (0.155 g; 0.546 mmol), HBTU (0.197 g; 0.52 mmol) and DIEA (0.188 ml, 1.092 mmol) in DMF (3 ml) was added to the wet resin-bonded glycopeptide 35 and the whole was stirred for 6 h at room temperature. The reaction course was followed by Kaiser ninhydrin test. The resin was washed with DCM (3×10 ml), DMF (2×10 ml), EtOH (2×20 ml), MeOH (2×10 ml), diethylether (2×10 ml) and dried in vacuo over KOH for 24 h, to give resin-bonded glycopeptide 36.

N-[2-O-(Benzyl 2-acetamido-3,4,6-tri-O-benzyl-2-deoxy-β-D-gluco-pyranosyl-(1→4)-2-acetamido-6-O-benzyl-2,3-dideoxy-α-D-glucopyranosid-3-yl)-glycoloyl]-L-α-aminobutanoyl-D-isoglutaminyl-L-lysine(stearoyl) 38

The product 38 was split off from the resin (resin-bonded glycopeptide 36) and the reaction mixture was worked up by using the same procedure as given above in Example 6 for compound 30. Yield after HPLC purification 229 mg (41%) of compound 38; m.p. 222-225° C., $[\alpha]_D$ +34° (c 0.4; AcOH). $^1$H NMR spectrum: 4.86 d, 1 H, J=3.5 CH (C-1); 4.64 d, J=12.2 (CH$_2$-Ph); 4.61 d, 1 H, J=8.3 CH (C-1'); 4.51 d, J=12.2 (CH$_2$-Ph); 4.39 d, 2 H, J=15.7 [O(CH$_2$)CO]; 4.32 bq, 1 H, J=6.9 [CH(COOH)]; 4.20 dt, 1 H, J=5.4, 8.3, 8.3 [CH(CONH$_2$)]; 4.14 d , 2 H, J=15.7 [O(CH$_2$)CO]; 4.11 ddd, 1 H, J=5.1, 7.9, 9.0 [NHCH(CH$_2$CH$_3$)CO]; 3.96 dd, 2 H, J=2.1, 11.5 CH$_2$ (C-6'); 3.84 dd, 1 H, J=8.9, 9.6 CH (C-3); 3.79 ddd, 1 H, J=3.5, 7.4, 9.6 CH (C-2); 3.64 ddd, 1 H, J=2.1, 5.5, 9.7 CH (C-5'); 3.60-3.68 m, 5 H, CH$_2$ (C-6.2%3%4); 3.60-3.68 m, 5 H, J=(H-6.2',3',4'); 3.59 dd, 2 H, J=5.5, 11.5 CH$_2$ (C-6'); 3.46 dd, 1 H, J=8.9, 9.7 CH (C-4); 3.21 ddd, 2 H J=2.1, 4.8, 9.8 CH (C-5); 2.99 bq, 2 H, J=7.0 (CH$_2$CH$_2$CH$_2$CH$_2$NH); 2.14 m, 2 H (CH$_2$CH$_2$CO); 2.01 t, 2 H, J=7.7 (COCH$_2$C$_{15}$H$_{30}$CH$_3$); 1.90 m, 2 H (CH$_2$CH$_2$CO); 1.84 s, 3 H (NDCH$_3$); 1.81, 1 H (NHCH$_3$); 1.69 m, 2 H (CH$_2$CH$_2$CO); 1.66 m, 2 H [NHCH(CH$_2$CH$_3$)CO]; 1.66 m, 2 H (CH$_2$CH$_2$CH$_2$CH$_2$NH); 1.54 m, 2 H [NHCH(CH$_2$CH$_3$)CO]; 1.54 m, 2 H (CH$_2$CH$_2$CH$_2$CH$_2$NH); 1.06-1.28 m, 2 H (CH$_2$CH$_2$CH$_2$CH$_2$NH); 1.06-1.28 m, 15 H (COCH$_2$C$_{15}$H$_{30}$CH$_3$); 0.85 t, 3 H, J=7.0 [NHCH(CH$_2$CH$_3$) CO]; 0.81 t, 3 H, J=7.5 (COCH$_2$C$_{15}$H$_{30}$CH$_3$). $^{13}$C NMR spectrum: 173.49 s [O(CH$_2$)CO]; 172.87 s [NHCH (CH$_2$CH$_3$)CO]; 171.73 s (CH$_2$CH$_2$CO); 171.44 s [CH(COOH)]; 170.72 s (COCH$_2$C$_{15}$H$_{30}$CH$_3$); 169.85 s (NHCH$_3$); 169.36 s (NHCH$_3$); 169.18 s [CH(CONH$_2$)]; 138.51 s (CH$_2$-Ph); 138.45 s (CH$_2$-Ph); 138.38 s (CH$_2$-Ph); 138.08 s (CH$_2$-Ph); 137.43 s (CH$_2$-Ph); 128.05 d (CH$_2$-Ph); 128.03 d (CH$_2$-Ph); 128.01 d (CH$_2$-Ph); 128.00 d (CH$_2$-Ph); 127.94 d (CH$_2$-Ph); 127.93 d (CH$_2$-Ph); 127.48 d (CH$_2$-Ph); 127.39 d (CH$_2$-Ph); 127.36 d (CH$_2$-Ph); 127.30 d (CH$_2$-Ph); 127.19 d (CH$_2$-Ph); 127.14 d (CH$_2$-Ph); 127.08 d (CH$_2$-Ph); 126.99 d (CH$_2$-Ph); 126.94 d (CH$_2$-Ph); 99.92 d (C-1'); 95.67 d (C-1); 81.64 d (C-3); 78.09 d (C-4); 77.93 d (C-3') 075.69 d (C-4'); 74.25 d (C-5'); 71.90 t [O(CH$_2$)CO]; 70.32 d (C-5); 70.20 t (C-6'); 68.65 t (CH$_2$-Ph); 68.43 d (C-6); 55.57 d (C-2'); 53.20 d [CH(COOH)]; 52.68 d (C-2); 52.03 d [CH(CONH$_2$)]; 51.74 d [NHCH(CH$_2$CH$_3$)CO]; 38.04 t (CH$_2$CH$_2$CH$_2$CH$_2$NH); 35.30 t (COCH$_2$C$_{15}$H$_{30}$CH$_3$); 31.07 t (CH$_2$CH$_2$CO); 28.81 t (COCH$_2$C$_{15}$H$_3$OCH$_3$); 28.80 t (COCH$_2$C$_{15}$H$_3$OCH$_3$); 28.76 t (COCH$_2$C$_{15}$H$_3$0CH$_3$); 28.72 t (COCH$_2$C$_{15}$H$_{30}$CH$_3$); 28.66 t (COCH$_2$C$_{15}$H$_3$OCH$_3$); 28.56 t (COCH$_2$C$_{15}$H$_{30}$CH$_3$); 28.50 t (COCH$_2$C$_{15}$H$_{30}$CH$_3$); 28.46 t (CH$_2$CH$_2$CH$_2$CH$_2$NH); 27.81 d (CH$_2$CH$_2$CO); 25.60 t [NHCH(CH$_2$CH$_3$)CO]; 25.10 t (CH$_2$CH$_2$CH$_2$CH$_2$NH); 22.77 t (CH$_2$CH$_2$CH$_2$CH$_2$NH); 22.75 q (NHCH$_3$); 22.36 q (NHCH$_3$); 21.85 t (COCH$_2$C$_{15}$H$_{30}$CH$_3$); 13.69 q (COCH$_2$C$_{15}$H$_{30}$CH3); 09.65 q [NHCH(CH$_2$CH$_3$)CO]. For C$_{56}$H$_{121}$N$_7$O$_5$ calculated: relative molecular mass 1540.9, monoisotopic mass 1539.9. FAB-MS (DS; DMF), m/z: 1540.8 [M+H]$^+$, 1562.6 [M+Na]$^+$. HR MS, m/z: for C$_{86}$H$_{121}$O$_{18}$N$_7$Na=1562.86603 found 1562.86625 [Fragmentation: C$_{56}$H$_{65}$O$_{12}$N$_3$Na=994.44605 found 994.44627; C$_{57}$H$_{90}$O$_{13}$N$_6$Na=1089.64581 found 1089.64617; C$_{27}$H$_{34}$O$_7$N$_2$Na=521.22582 found 521.22576].

N-[2-O-(2-Acetamido-2-deoxy-βD-glucopyranosyl-(1→4)-2-acetamido-2,3-dideoxy-D-glucopyranose-3-yl)-glycoloyl]-L-α-aminobutanoyl-D-isoglutaminyl-L-lysine(stearoyl) (40; norAbu-GMDP-Lys-L18)

Compound 38 (0.4 g; 0.739 mmol) in acetic acid (80 ml) was hydrogenolyzed on 5% Pd/C (0.25 g) catalyst at room temperature for 48 h. The reaction course was followed by HPLC on a silica gel C-18 column in linear gradient of water-methanol (80%→100%). The reaction mixture was worked up by using the same procedure as given above in Example 8, to afford 160 mg (78%, calculated as monohydrate) of the compound 40, norAbu-GMDP-Lys-L18. For C$_{51}$H$_{91}$N$_7$O$_{18}$ calculated: relative molecular mass 1090.3, monoisotopic mass 1089.6. FAB-MS (DS, chloroform), m/z: 1090.7 [M+H]$^+$, 1112.7 [M+Na]$^+$. HR MS, m/z: for C$_{51}$H$_{91}$O$_{18}$N$_7$Na=1112.63128 found 1112.63011 [Fragmentation: C$_{43}$H$_{78}$O$_{13}$N$_6$Na=909.55191 found 909.55170; C$_{35}$H$_{65}$O$_8$N$_5$Na=706.47254 found 706.47223; C$_{16}$H$_{26}$O$_{10}$N$_2$Na=429.14797 found 429.14782].

Example 9

Preparation of norAbu-GMDP-Lys-B30

A solution of 2-tetradecylhexadecanoyl acid, HBTU and DIEA in DMF in the same molar ratio given in the Example 8 (procedure for compound 36) was added to the resin-bonded glycopeptide 35 prepared in Example 8

N-[2-O-(Benzyl 2-acetamido-3,4,6-tri-O-benzyl-2-deoxy-β-D-gluco-pyranosyl-(1→4)-2-acetamido-6-O-benzyl-2,3-dideoxy-α-D-glucopyranosid-3-yl)-glycoloyl]-L-α-aminobutanoyl-D-isoglutaminyl-L-lysine(2-tetradecylhexadecanoyl) 39

The product 39 was split off from the resin by treating the resin-bound lipoglycopeptide 37 by using the same procedure as given in Example 8 for product 38, to afford crude product 39. TLC in MeOH—CHCl$_3$—HCOOH (100:100:1) showed the presence of some impurities. Chromatography of the lyophilizate on a silica gel C-18 column in linear gradient of water-methanol (90%→100%) followed by lyophilization of homogenous fractions from acetic acid gave 32% of the compound 39. $[\alpha]_D$ +34° (c 0.2; AcOH). $^1$H NMR spectrum: 4.98 d, 1H, J=3.6 (H-1); 4.77 d, 1H, J=11.6 (CH$_2$-Ph); 4.70 d, 1H, J=10.7 (CH$_2$-Ph); 4.65 d, 1H, J=12.1 (CH$_2$-Ph); 4.63 d, 1H, J=8.1 (C-1'); 4.55-4.43 m 7H (H-arom.); 4.47-4.43 m, 1H (α-iGln); 4.40 d, 1H, J=15.8 (OCH$_2$CO); 4.35 m (α-Abu); 4.33 m, 2H (CONH$_2$); 4.29 d, 1H, J=15.8 (OCH$_2$CO); 4.12 dd, 1H, J=3.6, 10.8 (H-2); 3.97 dd, 1H, J=9.0, 10.5 (H-4); 3.77 dt, 1H, J=2.5, 2.5, 10.5 (H-5); 3.67-3.60 m, 3H (H-2', H-3', H-4'); 3.67-3.60 m, 2H (H-6); 3.61 dd, 1H, J=9.0, 10.8 (H-3); 3.70-3.58 m, 2H (C-6'); 3.40 ddd, 1H, J=2.1, 4.5, 9.9 (H-5'); 3.25-3.17 m, 2H (ε-Lys); 3.25-3.17 m, 1H {NHCOCH[(CH$_2$)$_{13}$ CH$_3$]$_2$}; 2.42 t, 2H, J=7.3 (γ-iGln); 2.13-2.10 m, 2H (β-iGln); 2.03 s, 1H (NHCOCH$_3$); 1.90-1.63 m, 6H (β-Lys, γ-Lys, δ-Lys); 1.87 s, 3H (NHCOCH$_3$); 1.80-1.50 m, 2H (β-Abu); 1.50-1.18 m, 52H {NHCOCH[(CH$_2$)$_{13}$CH$_3$]$_2$}; 0.90 t, 6H, J=7.4 {NHCOCH[(CH$_2$)$_{13}$CH $_3$]$_2$}; 0.86 t, 3H, J=7.4 (γ-Abu). $^{13}$C NMR spectrum: 101.09 d (C-1'); 96.93 d (C-1); 82.43 d (C-3); 79.80 d (C-3'); 79.19 d (C-4'); 76.80 d (C-4); 75.59 t (CH$_2$-Ph); 75.51 t (CH$_2$-Ph); 75.15 d (C-5'); 73.86 t (CH$_2$-Ph); 73.82 t (CH$_2$-Ph); 71.42 d (C-5); 70.57 t (OCH$_2$CO); 70.46 t (CH$_2$-Ph); 69.15 t (C-6'); 68.86 t (C-6); 55.72 d (CONH$_2$); 55.64 d (Abu-CH); 53.84 d (iGln-CH); 53.75 d (C-2'); 53.44 d (C-2); 39.57 t (Lys- CHCH$_2$CH$_2$CH$_2$CH$_2$); 33.42 t {NHCOCH[CH$_2$]$_{13}$CH$_3$]$_2$}; 32.73 t (Lys-CHCH$_2$CH$_2$CH$_2$CH$_2$); 31.08 t {NHCOCH[(CH$_2$)$_{13}$CH$_3$]$_2$}; 30.33-29.60 t {NHCOCH[CH$_2$]$_{13}$CH$_3$]$_2$}; 25.42 t (iGln-CHCH$_2$); 25.42 t (Lys-CHCH$_2$CH$_2$CH$_2$CH$_2$); 23.66 t (Abu-CH$_2$); 22.64 t (iGln-CHCH$_2$CH$_2$); 22.59 t (Lys-CHCH$_2$CH$_2$CH$_2$CH$_2$); 14.29 q {NHCOCH[(CH$_2$)$_{13}$CH$_3$]$_2$}; 10.39 q (Abu-CH$_3$). HR MS, m/z: for C$_{98}$H$_{145}$O$_{18}$N$_7$Na=1731.05383 found 1731.05647 [Fragmentation: C$_{69}$H$_{114}$O$_{13}$N$_6$Na=1257.83361 found 1257.83301; C$_{56}$H$_{65}$O$_{12}$N$_3$Na=994.44605 found 994.44550; C$_{27}$H$_{34}$O$_7$N$_2$Na=521.22582 found 521.22538]

N-[2-O-(2-Acetamido-2-deoxy-β-D-glucopyranosyl-(1→4)-2-acetamido-2,3-dideoxy-D-glucopyranose-3-yl)-glycoloyl]-L-α-aminobutanoyl-D-isoglutaminyl-L-lysine(2-tetradecylhexadecanoyl) (41; norAbu-GMDP-Lys-B30)

Compound 39 was hydrogenolyzed in acetic acid on 5% Pd/C catalyst at room temperature for 24 h. The reaction course was followed by HPLC by using the conditions given in Example 8 (procedure for compound 40). The vessel was flushed with argon, the catalyst was filtered off, washed with acetic acid and the filtrate was lyophilized. Chromatography of the lyophilizate on a silica gel C-18 column in linear gradient of water-methanol (80%→100%) followed by lyophilization of homogenous fractions from acetic acid gave 37% of the compound 41, norAbu-GMDP-Lys-B30. HR MS, m/z: for C$_{63}$H$_{115}$O$_{18}$N$_7$Na=1280.81908 found 1280.81970 [Fragmentation: C$_{55}$H$_{102}$O$_{13}$N$_6$Na=1077.73971 found 1077.73977; C$_{47}$H$_{89}$O$_8$N$_5$N=874.66034 found 874.66021; C$_{16}$H$_{26}$O$_{10}$N$_2$Na=429.14797 found 429.14791]

Example 10

Preparation of Liposomes Containing Adjuvants

Method A—Proliposome Method

The preparation used egg-yolk phosphatidylcholine (EPC, 95%), negatively charged lipid 1-palmytoyl-2-oleoyl-sn-glycero-phosphatidylglycerol (POPG) (Avanti Polar Lipids, USA) and a selected adjuvant in molar ratio of 4:16:1. A proliposome mixture was prepared using a modification of the described method[40,41]. Briefly, the lipids (300 mg of solid grains) were dissolved in pure warm ethanol (240 mg, 50° C.) and cooled to room temperature. A water phase was added according to the pattern lipid:ethanol:water 100:80:200 w/w/w. Tris-HCl (20 mM, pH 7.2) was used as the water phase. Poor water-soluble compounds such as the adjuvant compounds are preferably dissolved in ethanol and then added to phospholipids (adjuvant, 5 mol % of total lipid content). Thorough mixing of the ethanol solution of phospholipids with the water phase was achieved by the use of two high pressure glass syringes linked with short teflon capillary.

The water phase containing compounds to be entrapped was injected quickly from one syringe into the second syringe containing the ethanol solution of phospholipids. This process was repeated rapidly several times to give a homogenous preparation. The opaque viscous mixture was heated to 30° C. (transformation temperature) for 10 minutes in a sterile Eppendorf tube and then allowed to cool to room temperature yielding a proliposome mixture. Lower transformation temperatures were used in this preparation to prevent thermal decomposition of the adjuvant. The proliposome mixture was transferred into a stirred cell and converted into a liposome suspension by continuous dilution with the water phase (total volume of 39 ml) at a defined flow rate and temperature. The two-step dilution was accomplished by continual addition of 3 ml of the water phase at a flow rate of 100 µl/min in the first step and 36 ml of the water phase at 1000 µl/min in the second step.

Method B—Hydration Method

Liposomes (frozen-and-thawed multilamellar vesicles, FTMLV) were prepared from the egg-yolk phosphatidylcholine (EPC, 95%), negatively charged lipid 1-palmytoyl-2-oleoyl-sn-glycero-phosphatidylglycerol (POPG) (Avanti Polar Lipids, USA) and a selected adjuvant in molar ratio of 16:4:1 by the classical method of hydration of lipid film by apyrogenic phosphate buffered saline (PBS)[41]. The lipids and the adjuvant (5 mol % of total lipids) were dissolved in chloroform (300 mg in 6 ml) and deposited onto the wall of a round-bottom flask (250 ml) by removal of the solvent in a rotary evaporator (40° C., 4 h). The dried lipid film was then hydrated with the aqueous phase with continuous mixing on a mechanical reciprocal shaker for 2 h. FTML was obtained by freezing the multilamellar vesicles in liquid nitrogen and thawing them in a 30° C. water bath, repeating the cycle five times. The glassware was treated overnight at 180° C. to remove pyrogens. For application the liposomes were extruded through 0.2 µm isopore filter (Millipore)[42].

The size and zeta-potential (in PBS) of liposomes were determined by dynamic light scattering instrument Zetasizer 3000 (Malvern, Malvern, UK). Negatively charged liposomes prepared by hydration of lipid film or proliposome-liposome method and extrusion through polycarbonate filters had the size of 180 nm (polydispersity<0.1) and zeta-potential of −30.6 mV (PBS, 25° C.).

Metallo-chealting liposomes were prepared in the same way, but metallochalating lipids e.g. DOGS (Avanti Polar Lipids, USA) was added. The percentual content of DOGS (expressed in molar % of total lipid content) is 1-5%. Ni$^{+2}$ or Zn$^{+2}$ form of DOGS is used for binding of recombinant antigens with HISTAG.

Lyophilised liposomes are preferable as a long term storage formulation, and saccharose was used as a cryoprotectant. Liposomes designated for lyophilisation were prepared in saccharose solution (saccharose:lipid molar ratio was 5:1). The liposomal suspension was sterilized by filtration (0.22 µm filter) filled into appropriate vials (generally 1 ml per 5 ml vial), frozen to −70° C. and lyophilized (24 h) in the apparatus LyoVac GT-2 (Finn-Aqua, Finland).

Figure 7:
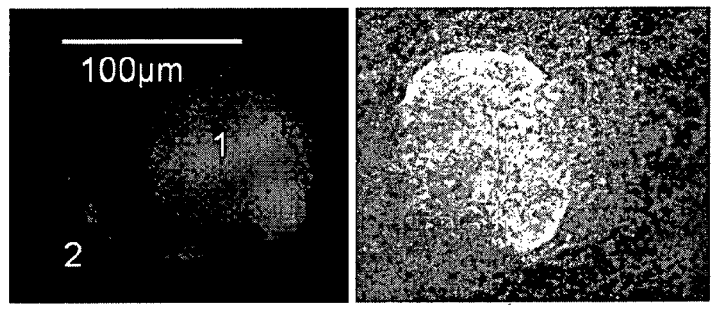
FIG. 7 shows AFM (left) and TEM (right) images of liposome with rHSP90 linked to the surface by metallochelating bond (1: Liposome with embedded muramyl glycopeptide derivatives for directed immune response; 2: (optional) recombinant HSP90 antigen linked via metallochelating interaction)
Figure 8:
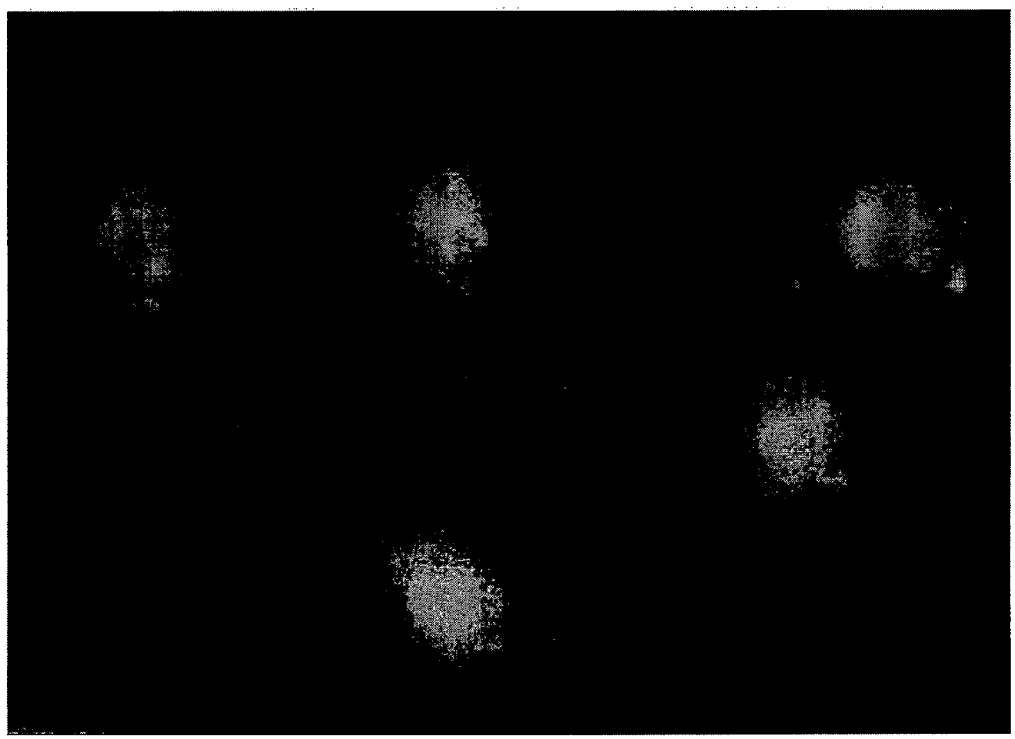
FIG. 8 shows AFM image illustrating that proteoliposomes are of homogeneous size and structure (rHSP90 antigen is linked to the surface by metallochelating bond)

Proteoliposomes can be prepared by coupling recombinant hsp90 antigen (r-hsp90, 6×HISTag) via a metal chelating lipid to liposomes containing muramyl glycopeptide derivatives as adjuvant component. Atomic Force Microscopy and Transmission Electron Microscopy images (FIGS. 7 and 8) show the homogenity in size and structure of the obtained proteoliposome constructs with liposome embedded muramyl glycopeptide derivatives and (optional) recombinant antigen attached to the outside. Some of the muramyl glycopeptide derivatives are likely to be protruding with their hydrophilic part out of the liposome which makes them accessible to cellular recognition and allows for enhanced (targeted) uptake by dendritic cells and macrophages (FIGS. 9 and 10).

The specific uptake of the proteliposome vaccine by antigen presenting cells (APCs) directly responsible for initiating the immune response is a novel feature that allows for targeted immune responses. Firstly, the uptake is enhanced and the surface antigen non-covalently attached to the liposome. This facilitates presentation of the antigen in the context of the APC MHC-I complex which is required for the activation of CD8+ T cells and Th1-type immune responses. Secondly, while all the muramyl glycopeptide derivatives tested were able to elicit strong cellular responses comparable to FCA, some, in particular compound 24, showed weak to non-existent antibody responses which may help (a) in the treatment of cryptic viral infections, where the virus is hidden inside the cell for extended periods of time and (b) a shift of Th2 versus Th1-type responses in atopic conditions.

Use of a metal chelating lipid for the attachment of the antigen to the liposome was used for proof of principle, but any type of linker that allows for anchoring in the liposome membrane and coupling of the antigen post formation of the liposome is permissible. Non-covalent or cleavable linkage is advatagous with respect to antigen processing via MHC-I pathway.

Use of an antigen for co-delivery with liposome embedded muramyl glycopeptide derivatives was used as proof of principle, but any substance or combination of substances with immunomodulatory activity (e.g. CpG oligonucleotides or monophosphoryl lipid A or immunosuppressive drugs) that can alter or modulate the response of APCs can be delivered in a similar fashion.

Example 11

Screening for Pyrogenicity

Method:
The test was conducted in an authorised laboratory, ITEST plus s.r.o., Bilé Vchýnice 10, 533 13 Vápno u Přelouče, Czech Republic, according to guide-lines ČL 2005.

Rabbits (New Zeeland albino, 4-6 kg, 3 animals per group) were used for testing.

Liposomal preparations of muramyl glycopeptide derivatives were administered s.c. (100 nmol/kg). Empty liposomes were used as negative control and the liposomal as well as the free form of muramyl dipeptide (MDP) (25 µg/kg, corresponding to 50.7 nmol/kg) served as positive control. Temperature was measured in 1, 2, 3, 4,6 and 24 hour intervals.

Results:
Empty liposomes were used as negative control; and liposomal as well as free muramyl dipeptide (MDP) (50.7 nmol/kg) served as positive control. B30-norAbu-MDP (MT01, structure on page 5) served as additional control. Temperature was measured in 1, 2, 3, 4, 6 and 24 h intervals. The preparation passed the test if the Sum of ΔTmax remained below 1.1° C. (3 rabbits per group)

TABLE 1

Pyrogenicity

| | | Tested compounds | | | | | | | | |
|---|---|---|---|---|---|---|---|---|---|---|
| | Liposomes | liposomal MDP | free MDP | MT01 | 23 | 24 | 32 | 33 | 40 | 41 |
| +ΔTmax ° C. | 0.2 | 2.7 | 2.9 | 0.5 | 0.7 | 0.7 | 0.5 | 0.4 | 0.6 | 0.8 |

All tested derivatives proved to be non-pyrogenic.

Example 12

Proteoliposomes against Fungal Infection (*Candida Albicans*)

*Candida albicans* occurs naturally in the gut flora of 80% of the human population with no harmful effects. Overgrowth, candidiasis, is a frequent complication of immunocompromised individuals such as HIV-positive patients, transplant patients, cancer patients on chemotherapy or radiation therapy, and a major cause of morbidity and death. In addition, they have become a major concern for hospital-related infections, such as in intensive care units.

Hsp90 is one of the most abundant proteins expressed in cells. It is a member of the heat shock protein family which is upregulated in response to stress. Hsp90 is found in bacteria and all branches of eukarya. The sequence of the hsp90 molecule from *Candida albicans* used in the immunization is sufficiently different from that of mice (and man) to avoid cross-reactions.

Method for 12.1 (*Candida Albicans* hsp90, Basic Evaluation):

Proteoliposomes were prepared by coupling recombinant hsp90 antigen (r-hsp90, 6×HISTag) via a metal chelating lipid to liposomes containing muramyl glycopeptide derivatives as adjuvant component. BALB/c male mice 4 to 5 weeks old (female 20±2 g, 5 animal per group) were immunized by the intradermal route either with 20 µg of free or liposomal r-hsp90 (volume of 60 µl) either with or without L18-norAbu-MDP and boosted 21 days later by the same composition of experimental vaccine. FCA was used as positive control r-hsp90. Liposomal vaccine composition 20 µg of rHSP90 antigen, 5% metallochelating lipid, 5% particular MT analogue, 90% phospolipids.

Blood samples were collected from the tail vein into heparinised capillary PCV tubes. After centrifugation, the upper part of the tube, containing 15 ml blood serum, was cut off, thrown into 500 ml diluting solution and thoroughly shaken. Thus, a basic dilution of 1:33 was obtained. The pre-diluted sera were kept at −20° C. Blood samples were collected before the first immunization, 2 weeks thereafter and subsequently at weekly intervals up to the 4th week after the second immunisation. Specific IgG antibodies in blood serum samples were determined by the standard indirect ELISA procedure. The data obtained were processed statistically using the non-parametric Mann-Whitney U-test.

Production of INF-γ was mesured by standard ELISPOT assay (R&D, USA). Immunised mice were sacrified 4 weeks after booster imunisation and splenocytes were isolated, and stimulated by r-hsp90 (50 µg/ml) and spots were counted.

Method for Experiment 12.2 (*Candida Albicans* hsp90, Antibody Response):

Proteoliposomes with muramyl glycopeptide derivatives were prepared as described above, but the boost was carried out already after 14 days. The liposomal vaccine composition was as for Experiment Set 1: 20 µg of rHSP90 antigen, 5% metallochelating lipid, 5% particular MT analogue, 90% phospolipids.

Controls: Aluminum hydroxide (AlOH) and Freund complete adjuvans (FCA) were used as positive controls. PBS with empty liposomes was used as negative control (control). Humoral response was tested at day 14 after vaccination (post priming) and at day 20 after vaccination (post booster). Antibody titres were wer assayed by ELISA.

Method for Experiment 12.3 (*Candida Albicans* hsp90, Cellular Response):

Proteoliposomes with muramyl glycopeptide derivatives were prepared as described above. Experimental conditions were as for Experiment 12.2.

Cell mediated immune response against rHSP90 antigen formulated in liposomal experimental vaccine was tested at day 20 (6 days after booster). Mice were sacrificed, splenocytes were purified and production of IFN-γ in splenocytes stimulated by rHSP90 was assayed by flow cytometry.

Results:

Co-entrapment of lipophilic derivative L18-norAbu-MDP into proteoliposomes (FIG. 11) increased significantly both the humoral and cellular immune response towards a proteoliposome based experimental vaccine. The intensity of the immune response was comparable to the intensity provoked by FCA administration, which serves as a gold standard for adjuvants (FIGS. 11 and 12).

Adjuvant effects of the muramyl glycopeptide derivatives (compounds 23, 24, 32, 33, 40) were tested for their effects on the induction of antibody (FIG. 13) and cellular responses (FIG. 14). MDP, B30-norAbuMDP, Aluminum hydroxide (AlOH) and Freund complete adjuvans (FCA) were used as positive controls. PBS with empty liposomes was used as negative control ("control").

All tested compounds induced cell-mediated response comparable to aluminium hydroxide or CFA. However, marked differences were observed for the induction of antibody responses, which were strong and comparable to AlOH for compounds 32, 33, 40.

Example 13

Proteoliposomes against Bacterial Infection (*Borrelia burgdorferi*)

*Borrelia* is the causative agent of borreliosis (Lyme disease), a zoonotic, vector-borne disease transmitted primarily by ticks and some by lice, depending on the species.

The outer surface protein A (OspA) is a *Borrelia* immunogenic lipoprotein. A major limitation of the current OspA vaccine for Lyme disease is that it is directed against an antigen expressed predominantly in the tick vector. Another immunoprotective antigen is OspC which is expressed in early infection.

Method for Experiment 13.1 (Antibody Response):

Proteoliposomes with muramyl glycopeptide derivatives were prepared as described above (71% mol EPC, 19% mol POPG, 5% mol DOGS-Ni, 5 mol % MDP or MDP analogues). BALB/c male mice 4 to 5 weeks old (female 20±2 g, 4 animal per group) were immunized by the intradermal route with 20 µg of liposomal OspC (volume of 60 µl) either with or without B30-norAbu-M DP and boosted 21 days later by the same composition of experimental vaccine. Aluminium hydroxide (AlOH) and FCA (Freund complete adjuvans) were used as positive controls. MDP was used as the standard to which the new derivatives were compared.

Method for Experiment 13.2 (Cellular Response):

Proteoliposomes with muramyl glycopeptide derivatives were prepared as described above.

Cell mediated immune response against OspC antigen formulated in liposomal experimental vaccine was tested at day 20 (6 days after booster). Mice were sacrificed, splenocytes were purified and production of IFN-γ in splenocytes stimulated by OspC was assayed by flow cytometry.

Results:

The adjuvant effects of the muramyl glycopeptide derivatives (compounds 23, 24, 32, 33, 40) were tested for their effects on the induction of antibody (FIG. 15) and cellular responses (FIG. 16). MDP, B30-norAbuMDP, Aluminum hydroxide (AlOH) and Freund complete adjuvants (FCA) were used as positive controls. PBS with empty liposomes was used as negative control ("control")

Example 14

Proteoliposomes against Viral Infection (*Porcine Circovirus*)

*Porcine Circovirus* (PCV) is a single stranded DNA virus and the smallest type of virus replicating autonomously in eukaryotic cells. The virus is causes problems on pig rearing farms with the increasing occurrence of PCV associated postweaning multisystemic wasting syndrome (PMWS) which, over time, results in significant depletion of lymphocytes. Post mortem of diseased animals reveals enlarged lymph nodes and abnormal lung tissue.

Method:

Proteoliposomes with muramyl glycopeptide derivatives were prepared as described above with recombinant PCV2 capsid antigen.

Results:

The antibody response raised with the proteoliposome based vaccine did not quite reach that of FCA based vaccines.

In terms of safety, though, proteoliposome based vaccines have a clear advantage over oil-based vaccines, as illustrated by the reduced skin lesion in FIG. 17.

Example 15

Adjuvant Activity for Protein Vaccine against Vacteria (Tetanus)

Method:

BALB/c male mice, 4 to 5 months old, were immunized by a subcutaneous route either with 100 μg of free tetanus toxoid (TaT, crude anatoxin, Sevac, Prague, partially purified by size exclusion chromatography, concentrated and formaldehyde-inactivated) or with 10 μg of liposome-encapsulated TaT per animal. Test compounds (MDP analogues) were used at the dose 100 nmol/per mouse. As a positive control, alum gel (Alugel, Giulini Chem.) containing 3.7% of aluminium at a dose of 25% v/v alum gel per mouse was used. Each mouse received 0.2 ml of antigen preparation subcutaneously. The same dose was administered after three weeks. Blood samples were collected from the tail vein into heparinised capillary PCV tubes. After centrifugation, the upper part of the tube, containing 15 ml blood serum, was cut off, thrown into 500 ml diluting solution and thoroughly shaken. Thus, a basic dilution of 1:33 was obtained. The pre-diluted sera were kept at −20° C. Blood samples were collected before the first immunization, 2 weeks thereafter and subsequently at weekly intervals up to the 4th week after the second immunisation. Specific IgG antibodies in blood serum samples were determined by the standard indirect ELISA procedure. The data obtained were processed statistically using the non-parametric Mann-Whitney's U-test.

Results:

For determining the adjuvant activity of N-L18-norAbu-GMDP (compound 23), fresh liposomes were prepared on the day of administration. The TaT antigen and compound 23 were encapsulated into multilamellar liposomes using the method of lipoid film hydration with PBS containing the components to be encapsulated. The encapsulation rate was almost 100% for the lipophilic compound 23. The encapsulation rate for TaT was 60%.

FIG. 18 shows the dynamics of anti-TaT antibody responses induced in mice with free TaT or TaT encapsulated into liposomes alone or in combination with 100 nmol of free or co-encapsulated compound 23. Individual curves represent the geometric means of ELISA antibody titres for each group. Asterisks indicate significance of differences *($p<0.05$), **($p<0.01$), in comparison with the antibody response to TaT alone As illustrated by FIG. 18, the entrapment of tetanus anatoxin (TaT) into liposomes together with compound 23 proved to be an effective vaccine formulation with respect to humoral response. Free compound 23 mixed with free TaT did not show a significant antibody response in comparison to TaT antigen applied alone.

Compound 23 is an example for lipophilic compounds that can be easily entrapped into lipid structures and hence represents a suitable derivative for preparation of lipid based vaccine formulations, e.g. liposomes, cochleates, and lipid emulsions. Strong adjuvant activity was found for liposomal formulation of tetanus anatoxin antigen co-entrapped with compound 23.

Example 16

Adjuvant activity for DNA Vaccines against Fungi (Ringworm)

Method:

Albionitic female guinea pigs, weighing approximately 350 g (company ANLAB, CZ,: infection free certificate) were kept in quarantine for 14 days before the experiments.

The domain organization of GroEL protein can be found in the art[46]:

1-130 aa corresponds to the equatorial domain 131-191 aa corresponds to the intermediate domain 192-375 aa corresponds to the apical domain 376-408 aa corresponds to an intermediate domain 409-525 corresponds to the equatorial domain pVAX-1 is a commercially available DNA plasmid from Invitrogene.

The treatment schedule was (1) 48 hours prior to infection; "−48 h", (2) 24 hours prior to infection, "−24 h"; (3) At the same time as infection, "0 h"; (4) 24 hours post infection, "+24 h".

The animals were infected by application of a standard dose of inoculum of the strain *Trichophyton mentagrophytes* TM 179 into scarified skin on side. TM 179 is a dermatophyte (Athroderma benhamiae), virulent for both men and animals (isolated and stored at Institute of Immunology, Olomouc). It is characterised by fibrous growth on solid media with rich microconidial sporulation. Prior to the experiment, the strain was passed through guinea pigs and recultivated.

The reaction of the skin was examined and classified at 12, 21 and 28 days after infection. The classification was carried out using a semi-quantitative 0 to +++ method (where U=ulceration) for evaluation of dermal reactions, i.e. pathological lesions. In addition, samples from the skin leasons were taken for cultivation after 8 days, and cultivated for a further 5 days to prove *Trichophyton mentagrophytes* infection.

Results:

Guinea pigs were treated with B30-norAbu-MDP (MT-01) and inoculated with the plasmid as detailed in Table 2 ("electrop."=electroporation).

TABLE 2

DNA Vaccination Schedule (ringworm)

| Group | number of animals | 1st immunisation - Prime | | 2nd immunisation - Boost |
|---|---|---|---|---|
| 1. | 4 | −48 h 200 μg B30-norAbuMDP | 20 μg DNA electrop. | 20 μg DNA electrop. |
| 2. | 4 | −24 h 200 μg B30-norAbuMDP | 20 μg DNA electrop. | 20 μg DNA electrop. |
| 3. | 4 | 0 h 200 μg B30-norAbuMDP | 20 μg DNA electrop. | 20 μg DNA electrop. |
| 4. | 4 | +24 h 200 μg B30-norAbuMDP | 20 μg DNA electrop. | 20 μg DNA electrop. |
| 5. | 4 | Control group | 20 μg DNA electrop. | 20 μg DNA electrop. |
| 6. | 4 | Control group | — | — |

The animals were inoculated by electroporation with 20 μg per animal pVAX-1 plasmid DNA and 200 μg per animal adjuvant compound. This plasmid is encoding for the gene fragment hsp 60 *Trichophyton mentagrophytes* pod under control of the CMV promoter. The plasmid is encoding for 270 amino acids of the Hsp60 sequence that corresponds to the immunogenic part of the equatorial domain. The immunogenic apical domain of Hsp60 *Trichophyton mentagrophytes* (a GroEL analogue) corresponds to human Hsp60, amino acids 134-402. The Hsp60 from *T. mentagrophytes* was described in October 1999 (Acc. No. AAF07213). This portion comprises the immunogenic fragment F3 of hsp60 from Histoplasma capsulatum[45].

The results of the experiments are detailed in Table 3: column 3 of Table 3 demonstrates that all animals were infected. The results were confirmed by cultivation (column 5). Columns 6 and 7 show that the animals in groups 3 and 4 are heading for almost complete recovery (therapeutic vaccination), while animals in groups 1 and 2 are also quite well advanced in recovery (prophylactic vaccination). The animals in group 5 inoculated with plasmid but without B30-norAbu-MDP, showed a weaker recovery.

The observed pathological lesions developed as inflammatory dermal lesions under the clinical picture of dermatophytosis with abundant desquamation and formation of crusts. As illustrated by FIG. 19, animals treated with the therapeutic vaccine show an accelerated healing of lesions.

TABLE 3

DNA Vaccination Results (ringworm)

| | Infection | Day 12 Skin reaction | Day 8 Sampling for cultivation | Day 13 Results of cultivation | Day 21 Skin reaction | Day 28 Skin reaction |
|---|---|---|---|---|---|---|
| group 1 | | | | | | |
| animal no: 1 | | + | | Positive | ++ | 0-+ |
| animal no: 2 | | ++ | | Positive | ++ | + |
| animal no: 3 | | ++-+++ | | Positive | +++ | + |
| animal no: 4 | | ++-+++ | | Positive | +++ | + |
| group 2 | | | | | | |
| animal no: 1 | | +++ | | Positive | ++ | + |
| animal no: 2 | | ++-+++ | | Positive | + | 0 |
| animal no: 3 | | ++ | | Positive | + | 0-+ |
| animal no: 4 | | +++ | | Positive | ++ | + |
| group 3 | | | | | | |
| animal no: 1 | | +++ | | Positive | ++-+++ | +-++ |
| animal no: 2 | | + | | Positive | + | 0-+ |
| animal no: 3 | | + | | Positive | + | 0-+ |
| animal no: 4 | | +-++ | | Positive | + | 0 |
| group 4 | | | | | | |
| animal no: 1 | | +++ | | Positive | ++ | + |
| animal no: 2 | | + | | Positive | 0-+ | 0 |
| animal no: 3 | | + | | Positive | 0-+ | 0 |
| animal no: 4 | | +-++ | | Positive | ++ | + |
| group 5 | | | | | | |
| animal no: 1 | | +++ | | Positive | ++ | + |
| animal no: 2 | | ++-+++ | | Positive | ++-+++ | + |
| animal no: 3 | | +++ | | Positive | +++ | ++ |
| animal no: 4 | | +++ | | Positive | ++ | +-++ |
| group 6 | | | | | | |
| animal no: 1 | | +++U | | Positive | +++ | ++ |
| animal no: 2 | | ++-+++ | | Positive | ++-+++ | +-++ |
| animal no: 3 | | +++U | | Positive | +++ | ++ |
| animal no: 4 | | +++U | | Positive | +++U | ++-+++ |

Example 17

Stimulation of Innate Immunity to Fungal Infection (*Candida albicans*)

Method:

BALB/c female mice 8 weeks old, weighing 18-22 g, were infected i.v. with *C. albicans* strain 2091 (Collection of Microorganisms, Masaryk University, Brno), passaged on mice to increase their infectivity. Adapted *C. albicans* cells were lyophilized and the third passage was applied at a dose of $5 \times 10^5$ organisms per mouse. Tested substances were applied subcutaneously at doses of 10, 50, 100, 200 and 400 nmol in a volume of 0.2 ml PBS at 24 h after i.v. infection (10 animals/group). Control animals were administered only 0.2 ml PBS/mouse. Survival was monitored daily and reported as the percentage of animals surviving 30 days after infection. Survival curves were compared statistically by the log-rank test.

Results:

BALB/c female mice, 8 weeks old, were treated with liposomal and free B30-Nor-abuMDP and infected by *C. albicans*. Survival time and survival rate were prolonged significantly in the group treated with liposomal B30-Nor-abuMDP. No effect was observed in the group treated with free B30-Nor-abuMDP in comparison with the control (PBS). The results, in terms of particle clearing and killing of microbes, suggest stimlulation of a potent non-specific antimicrobial defence system involving cells of the mononuclear phagocyte system. Survival curves are represented in FIG. 20. Liposomal B30-norAbuMDP leads to an increase in survival by a factor of 5 while free (non-liposomal) B30-norAbuMDP had a lesser effect.

Example 18

Stimulation of Innate Immunity to Bacterial Infection (*Salmonella enterica*)

*Salmonella* in poultry is a zoonosis of global importance. Broilers are generally seen as the major reservoir of infection and their short life span of 5-6 weeks, coupled with the relative immaturity of the adaptive immune responsiveness in young birds, suggests that an adaptive response, induced by a live vaccine, will be poorer than that obtained in adult birds and that enhancers of innate immunity, such as muramyl glycopeptide derivatives are the agents of choice.

*Salmonella* infections are attributable to the following three subgroups of the *Salmonella enterica* species:

1. *Salmonella typhi*, the causative agent of typhoid fever. Although typhoid fever is not widespread in industrialized countries, it is very common in under-developed countries, and causes a serious and often fatal disease. The symptoms of typhoid fever include nausea, vomiting and fever. *S. Typhi* can only infect humans, and no other host has been identified. The main source of *S. Typhi* infection is from swallowing infected water. Food may also be contaminated with *S. Typhi*, if it is washed or irrigated with contaminated water.

2. *Salmonella Typhimurium*, until the mid 1980s the most common cause of food poisoning by *Salmonella*. *S. Typhimurium* causes a typhoid-like disease in mice. In humans the disease is less severe and not normally fatal; but it can be fatal in immunocompromized people, as well as in the elderly and the young. The disease is characterized by diarrhea, abdominal cramps, vomiting and nausea, and generally lasts up to 7 days.

3. *Salmonella Enteritidis*, the single most common cause of food poisoning in the United States that has emerged over the last 20 years. *S. Enteritidis* is particularly adept at infecting chicken flocks without causing visible disease, and spreading from hen to hen rapidly. When tens or hundreds of thousands of chickens live together, and are processed together, a *Salmonella* infection can rapidly spread throughout the whole food chain. A compounding factor is that chickens from a single farm may be distributed over many cities, and even states, and hence *Salmonella* infections can be rapidly dispersed through millions of people.

Method for Experiment 18.1 (*Salmonella Typhimurium*):

BALB/c female mice, 8 weeks old, weighing 18-22 g, were infected p.o. with *S. typhimurium* at a dose of $3.1 \times 10^9$ CFU/ml, 100 µl per mouse. Test compounds at doses of 5, 10, 25, 50, 100 and 200 nmol per mouse were applied in., s.c., i.v., or p.o. 3 and 1 days before experimental infection (10 animals per group). Various organs (intestines, liver, spleen, lungs) were examined for the presence of salmonellae on day 30 post infection. Results were expressed as numbers of colony forming units (CFU) of *S. typhimurium* per 1 gram of tissue. Statistically significant differences in numbers of CFU between the individual experimental groups were calculated by one-way analysis of variance.

Method for Experiment 18.2 (*Salmonella Enteritidis*):

Mice (BALB/c, female, 3-4 moths of age, 10 animals (5+5) per group) were stimulated p.o. 72 and 24 hours before infection. Liposomal preparation contained 20 nmol of test compound per dose 1000 µg/kg). Infection was induced by *Salmonella enteritidis* at an LD50 dose (200 µl of bacterial inoculum per p.o. dose). 5 mice of each group were sacrificed at day 6 after infection and *Salmonela Enteritidis* was assayed in the inner organs (spleen, illeum, liver and lungs) by recultivation and the extend of infection was expressed in CFU. At day 12 the rest of survivors was sacrificed and *Salmonella enteritidis* was again assayed in inner organs. The data were expressed in numbers of clear/infected/dead mice in the group. PBS and empty liposomes were used as negative controls. Liposomal muramyl dipeptide was used as the reference immunostimulator.

Results for Experiment 18.1 (*Salmonella Typhimurium*):

Mice treated with liposomal B30-norAbu-MDP were infected with *Salmonella*. It was found that doses in the range 3-50 µg B30-norAbu-MDP per mouse were effective for a significant reduction of the pathogen load, especially in the intestines and spleen (FIGS. 21 and 22, respectively). Both intranasal and oral administration was effective in reducing the pathogen tissue burden and effects could be better still at higher doses.

The extent to which the innate immune response of the host to intestinal pathogens affects colonisation is largely unknown. A number of authors have suggested that the host genetic background plays an important role in determining colonisation characteristics of *Salmonella*. There is also now considerable evidence that defensin production in the small intestine of the mouse plays a major role in conferring resistance to infection at the level of the mucosa[47]. The immune response in the intestines against intracellular pathogens, such as *Salmonella typhimurium* or *Cryptosporidium parvum* is linked to the production of interferon-γ that is initiated by IL-12. This cytokine is produced by activated macrophages and bridges innate and specific immune responses.

Liposomal preparations of B30-norAbu-MDP and L18-norAbu-GMDP were both able to induce immune responses in intestines. Results for LIP-B30-norAbu-MDP are illustrated in Table 4.

TABLE 4

Stimulation of innate immunity against *Salmonella Typhimurium* in mice.

| | *Salmonella typhimurium* | |
|---|---|---|
| Compound | Infection in intestines (CFU) | Infection in spleen (CFU) |
| Untreated Control | 3/6/1* | 2/7/1* |
| LIP-B30-norAbu-MDP | 9/1/0 | 7/3/0 |

*Numbers of animals: clear/infected/dead

Results for Experiments 18.2 (*Salmonella Enteritidis*):

Compounds B30-norAbuMDP, 24, 32, 33 show good protective effects with significantly improved survival rate (0 or 1 case). Some compounds had the lead in reducing infection at an early stage but proved less potent later on, impling different modes of action.

In total, both experiments imply utility of muramyl glycopeptide derivatives in the fight against salmonella infection. Owing to the genetical proximity of the strains involved, there also is a case to be made for utility in the fight against typhus.

TABLE 5

Stimulation of innate immunity against *Salmonella Enteritidis* in mice

| | Day 6 Organs | | | | Day 12 Organs | | | |
|---|---|---|---|---|---|---|---|---|
| Groups | Intest. | Liver | Spleen | Lungs | Intest. | Liver | Spleen | Lungs |
| Control (PBS) | 2/3/0 | 2/3/0 | 3/2/0 | 4/1/0 | 1/0/4 | 1/0/4 | 1/0/4 | 1/0/4 |
| Free Liposomes | 3/2/0 | 2/3/0 | 2/3/0 | 3/2/0 | 1/1/3 | 1/1/3 | 1/1/3 | 1/1/3 |
| 23 | 2/3/0 | 0/5/0 | 0/5/0 | 1/4/0 | 1/2/2 | 1/2/2 | 1/2/2 | 1/2/2 |
| 24 | 4/1/0 | 3/2/0 | 3/2/0 | 4/1/0 | 3/1/1 | 3/1/1 | 3/1/1 | 4/0/1 |
| 32 | 5/0/0 | 3/2/0 | 3/2/0 | 4/1/0 | 2/3/0 | 1/4/0 | 1/4/0 | 4/1/0 |
| 40 | 4/1/0 | 4/1/0 | 5/0/0 | 4/1/0 | 0/2/3 | 1/1/3 | 1/1/3 | 1/1/3 |
| 33 | 5/0/0 | 5/0/0 | 2/3/0 | 5/0/0 | 2/2/1 | 1/3/1 | 1/3/1 | 2/2/1 |
| 41 | 2/3/0 | 2/3/0 | 2/3/0 | 4/1/0 | 1/2/2 | 2/1/2 | 2/1/2 | 2/1/2 |

TABLE 5-continued

Stimulation of innate immunity against *Salmonella Enteritidis* in mice

| | Day 6 Organs | | | | Day 12 Organs | | | |
|---|---|---|---|---|---|---|---|---|
| Groups | Intest. | Liver | Spleen | Lungs | Intest. | Liver | Spleen | Lungs |
| B30-norAbu-MDP | 5/0/0 | 4/1/0 | 4/1/0 | 5/0/0 | 4/0/1 | 4/0/1 | 4/0/1 | 4/0/1 |
| Liposomal MDP | 3/2/0 | 2/3/0 | 2/3/0 | 4/1/0 | 3/1/1 | 3/1/1 | 3/1/1 | 3/1/1 | clear/infected/dead

Example 19

Stimulation of Innate & Adaptive Immunity to Viral Infection (Friend Virus)

Friend leukemia virus (FLV) is a strain of murine leukemia virus that is used in the early stages of the disease as an immunological mouse model of human AIDS. Friend virus induces acute erythroleukemia in adult mice. The disease proceeds through a two-stage progression. The initial stage of the disease is characterized by the polyclonal expansion of infected cells in bone marrow and the spleen. Because of the interaction of the viral envelope glycoprotein, gp55, with the erythropoietin (Epo) receptor, the induction of leukemia by the virus is specific for the erythroid lineage. The later stage is characterized by the acquisition of new mutations, specifically, the mutation of the p53 gene and proviral insertional activation of Spi1, which leads to the emergence of a leukemic clone.

Method:

DBA/2 male mice weighing 18-22 g were inoculated i.v. with 0.2 ml of polycythemia-inducing Friend virus suspension (approximately 50 focus-forming units, ffu). Groups containing from 12 to 15 animals were injected with different doses of the test substances from $10^{-5}$ to $10^{-7}$ mol/0.2 ml PBS per mouse intraperitoneally at day −10 and −3 before the infection. The infected control group was administered only PBS. In the course of the following two months, survival and histology of spleen, thymus, liver, lung, kidney, and lymph nodes (if enlarged) was followed up. Survival curves were compared statistically by the log-rank test.

The course of the infection (at the highest dose of 10 μmol per animal) and tumor progression were monitored by the follow up of splenomegaly, percentages of erythroleukemic cells (quantification of erythroleukemic cells with specific anti-TER119 monoclonal antibody in the spleen by FACS analysis). NK cell activity was tested in an early stage of the infection on day 16.

Experiments according to this method were not carried out with liposomal formulations of the substances. As a result, the applied doses are about 100-1000 times higher as compared to previous Examples.

Survival (Early and Late Phase)

Animals (104) were infected and separated into two treatment groups (52 each; non-treated and treated with compound 23). The percentage numbers of survivors on day 45 (late early phase) are shown in Table 6.

TABLE 6

Stimulation of innate immunity against Friend virus infection

| No. of mice | | % of survivors on day 45 |
|---|---|---|
| 52 | Infected and non-treated | 23 |
| 52 | Infected and treated with compound 23 | 45 |

In a subsequent experiment, DBA/2 mice, weighing 20 g, 10-12 animals per group, were injected intra peritoneally with the compounds 23, 24, 32, 33, 40 and 41 at the 10 μmol dose. Survival of FLV inosculated mice at critical time points for innate immunity (early phase—day 43) and adaptive immune response (late phase—days 55 and 59) are shown in FIG. 23. In the early period, substances 32 and 40 protected all the animals from death. In the later period (adaptive immune response), substance 24 had the strongest effect on preventing death (30% survival). The difference between substance 23 and 24 (L18 vs B30 in the R3 position of norAbuGMDP) in survival of FLV infection is remarkable: compound 23 is better in the early phase (although only slightly better than saline control), compound 24 is drastically better in the late phase. Both these compounds are disaccharides with a lipid anchor in the R3 position: fatty acid (L18) in the case of compound 23 and branched fatty acid (B30) in the case of compound 24. It is compound 24, the compound with the largest survival benefit in FVL, that gave strong Th1-type responses with virtually no Th2-type response (Example 12). However, it also is this compound that has a smaller survival benefit in lethal irradiation experiments (Example 26).

Tumour Expansion (Early Phase)

TER119 is a monoclonal antibody that reacts with mouse erythroid cells from early proerythroblast to mature erythrocyte stages. A characteristic feature of FLV-infection is the proliferation of TER119+erythroleukemic cells (originating in bone marrow) in the spleen that enables to follow the progression of disease by microscopic (number of TER119+ cells, FIG. 24) and macroscopic (splenomegaly, FIG. 25) parameters.

Results (FLV Infection, Day 16):

Compounds 32 and 40 have a dose-dependent, positive effect in the early phase of the infection on reducing clonal expansion of TER-119+ erythroleukaemia cells (FIG. 24). It is these two compounds that ensure 100% survival versus 82% survival for the saline control group in the early phase of the infection (FIG. 23).

Compounds 24 and 41 have a pronounced opposite effect (FIG. 24). This is consistent with a survival rate worse than control (saline) in the early phase of the infection (FIG. 24). However, it is these compounds that ensure long-term survival (FIG. 23). Compound 23 also has a positive effect on clonal expansion of TER-119+ erythroleukaemia cells, but it leads to survival not worse than control at day 43 while its clearly worse at day 55 (FIG. 23).

For virtually all the compounds, including compounds 23, 24 and 41, clonal expansion of TER-119+ erythroleukaemia cells decreases with increasing dose.

Spleen size (FIG. 25) does not correlate well with TER-119+ erythroleukaemia cell clonal expansion data. Compound 24 and 40 show the strongest opposite effects on inducing (compound 24) and reducing (compound 40) clonal expansion, yet the effect on spleen size is small with both compounds leading to a spleen size slightly lower than the control. For both compounds 23 and 41, increased clonal expansion correlates with increased spleen size; and, interestingly, although both compound 24 and 41 lead to considerable clonal expansion, the one with the smallest effect on spleen size (compound 24) is the best compound for long-term survival.

Example 20

Stimulation of NK Cell-Mediated Cytotoxicity

Method for Experiment 21.1 (Mouse):

Ex vivo effects of NK cells of mice (DBA/2) can be tested in 18 hrs $^{51}$Cr-release assay against NK-sensitive YAC1 target cells. In the example, the mice were from Method 8, day 16, and test parameter was the cell-mediated cytotoxicity of spleen mononuclear cells (SMCs) in the presence or absence of test compounds. Cell free supernatants (25 µl) were harvested and the radioactivity detecting the lysed targets measured by beta-counter (Microbeta Trilux, Wallac). Test compounds were added at concentrations of $10^{-4}$ to $10^{-7}$ mol/ml.

Method for Experiment 20.2 (Man):

Ex vivo effects of test compounds on NK cells were evaluated on human peripheral blood mononuclear cells (PBMC). The NK cell cytotoxicity of healthy donors in the presence or absence of test compounds was measured in standard 4 hrs $^{51}$Cr-release assay against NK sensitive K562 cell line in effector (PBMC) to target (K562) ratio 16:1. Test compounds were added at a concentration of $10^{-7}$ mol/ml.

Results for Experiment 20.1 (Mouse):

Testing of compounds 23, 24, 32, 33, 40 and 41 for their capacity to induce cell-mediated cytotoxicity of spleen mononuclear cells (SMCs) is shown in FIG. 26. The mice were inoculated with FLV and blood samples were taken at day 16. The lytic activity of SMC was measured after 18 hours of incubation with NK-sensitive YAC1 target cells as described in Method 9.

Compounds 40 and 32 stimulate NK cell functional activity. These two compounds showed a reduction in TER-119+ erythroleukaemia cell clonal expansion. Comparison of 3.5h and 18h cytotoxicity assays showed stimulatory action over the whole time course for compound 40.

In contrast, compound 24, and partially 33, had an inhibitory effect. Compound 24 was the best compound ensuring LT survival (30% vs 0%).

Results for Experiment 20.2 (Man):

Testing of compounds 23, 24, 32, 33, 40 and 41 for their capacity to induce cell-mediated cytotoxicity of human eriph-eral blood mononuclear cells (PBMCs) is shown in FIGS. 27 and 28. All donors were healthy. 60% of the donor samples showed an induction of NK cell activity. The cytotoxicity of untreated controls (30.5%) was renormalized to 100%.

All the compounds had an effect on stimulating NK cell activity, particularly when focussing on the longer pre-incubation time (18 hours, FIG. 28). Compounds 24, 40, 41, 32 showed a negative dose response, compounds 33 and 23 showed a positive dose response in the range 0.1 µM-100 µM. If the negative dose response was associated with solubility issues, compound 33, the most hydrophobic compound, should show the largest effect. However, the opposite effect was observed.

All compounds showed a lag time to reach full activity which was most pronounced for compounds 24 and 32 which implies some kinetic effect, which probably is larger for liposomal as compared to 'free' (micellar) formulations. The difference between 'free' and liposomal formulations otherwise is small, apart from compound 24 (a disaccharide with branched fatty acid in the R3 position, FIG. 29).

Co-adminsitration of cytokines (IFN-β and IL-2, FIG. 30) has a synergistic effect for all compounds, which is more pronounced for FN-β than for IL-2.

Example 21

Stimulation of Th1-Mediated Cytotoxicity

Method:

Induction of experimental allergic encephalomyelitis (EAE) is a well-established in vivo model for TH1 (cell mediated immunity) response and monitoring of adjuvant activity. White guinea pigs, males weighing 250-300 g (7-13 animals per group) were inoculated into both hind footpads (0.2 ml to each) with an emulsion of 50 µg myelin basic protein (from bovine brain—Sigma) and 1 mg of test compounds in 0.4 ml of Freund's incomplete adjuvant (FIA). Freund's complete adjuvant with 4 mg/ml *Mycobacterium tuberculosis* (FCA) served as a positive control. Clinical symptoms of EAE, i.e. pareses or even death, were followed up to the 21st day after inoculation. Incidence of EAE was calculated as percentage of EAE positive animals.

Results:

Induction of experimental allergic encephalomyelitis (EAE) is a well-established in vivo model for TH1 (cell mediated immunity) response and adjuvant activity. Both hydrophilic NorAbuGMDP and lipophilic compound 23 are superior to MDP and GMDP as Th1 adjuvants. These compounds are adjuvants as good as FCA, which is the gold standard for Th1 adjuvants.

TABLE 7

Increase of Th1 stimulation in norAbu-substituted compounds vs. MDP and GMDP

| Compound | MDP | GMDP | NorAbuGMDP | Compound 23 | FCA |
|---|---|---|---|---|---|
| Positive animals (%) | 58 | 65 | 90 | 86 | 83 |

As illustrated by FIG. 31, guinea pigs were sensitized by bovine myelin basic protein emulsified in Incomplete Freund Adjuvant, supplemented by MDP, GMDP, norAbuGMDP, and compounds 23, 24, 32, 33, 40, 41. Again (compare Example 20), compound 24 showed the strongest effect on Th1 stimulation that was comparable to FCA. Compound 24 also was the best compound that conveyed LT survival in FLV challenged mice.

Compound 33 showed good results in the T-cell response to hsp90 challenge (FIG. 14). The result could be due to solubility, as compound 33 is very hydrophobic.

Example 22

Stimulation of of Bone Marrow (BM) Progenitor Cells

Method:
Determination of Colony stimulating activity (CSA) and co-stimulating activity (CoSA) in serum: Blood was taken at intervals from 5 to 48 h after injection of the test compounds, and the ability of the sera from treated mice to stimulate in vitro growth of colonies from granulocyte-macrophage progenitor cells (GM-CFC) was determined.

CoSA was determined as the ability of tested compounds, sera of treated mice, or conditioned medium from cultures of adherent stromal cells to enhance the number of GM-CFC colonies induced by a sub-optimal concentration of rmIL-3 in the above-described GM-CFC assay. The concentration of rmIL-3 was adjusted to a value which yielded one third of the maximum number of colonies on a dose-dependent curve.

Hematopoietic (HPCs), endothelial (EPCs) and stromal progenitor cells (SPCs) can be expanded in a similar fashion, but at different growth conditions (Pitchford et al., Cell Stem Cell. 2009 Jan. 9; 4(1):62-72.

Results:
As in Example 20, two closely related compounds are at the opposite end of the efficacy spectrum: while in Example 20, a disaccharide with branched fatty acid in the R3 position (compound 24) was better than the corresponding compound with linear fatty acid in this position (compound 23), it is now the monosaccharide with the linear fatty acide in the R2 position (compound 32) that is substantially better than the corresponding compound with branched fatty acid in this position (compound 33, no effect, FIG. 32).

Consistent with the strong effect on GM-CFC proliferation, compound 32 was the best compound for both GM-CFC proliferation and survival in mice primed with compound 24 before irradiation. However, if the compounds are injected 24 hours after sublethal irradiation, the picture again reverts with compounds that have a weaker effect on GM-CFC stimulation in FIG. 32, such as compound 23, 40, and even compound 33, becoming thre strongest performers in promoting GM-CFC proliferation (FIG. 33).

Example 23

Restoration of BM Proliferation in Immunosuppressive Therapy[44]

Method:
CBA/J male mice 8 weeks old, weighing 18-20 g were administered two i.v. doses of 200 nmol test substance per mouse 30 and 6 h prior to oral application of azathioprine (Imuran Wellcome, 5 mg per mouse in a volume of 0.5 ml distilled water). Bone marrow (lavage of femurs) was sampled 66 h after the application of azathioprine. Pooled suspensions of bone-marrow cells from 3 mice were cultivated in RPMI-1640 medium with 5% of fetal bovine serum (both from Sigma) at a concentration of $2\times10^5$ cells/0.2 ml either without mitogen (spontaneous proliferation) or in the presence of T (phytohemagglutinin, PHA Murex, 50 µg/ml; concanavalin A, Con A Sigma, 1, 2.5 or 5 µg/ml) or B (lipopolysaccharide, LPS E. coli O55 Difco, 5 µg/ml) mitogens for 48 h at 37° C. in 5% CO2. Proliferative activity was measured by incorporation of 3H-thymidine (1 µCi/well) and expressed as stimulation index SI=mean cpm cultures with mitogen/mean cpm controls without mitogen. Statistical significance of stimulation was evaluated by the Student's t test.

Results:
Injury to bone marrow following immunosuppression induced by chemotherapy is a common side effect of cancer chemotherapy. Immunosuppression is a characteristic feature of HIV patients, and it is a necessary therapeutic intervention in transplant patients and certain autoimmune diseases. Protection and accelerated restoration of bone-marrow activity is desired to improve outcomes and quality of life in patients receiving such therapy. Table 8 shows the restoration of bone-marrow proliferation in azathioprine-suppressed mice. Both GMDP and norAbu-GMDP proved to be efficient in mediating the restoration of bone marrow injured by azathioprine, a common immunosuppressant drug. The effect of norAbu-GMDP is in good accord with results from model experiments involving lethal and sublethal irradiation of mice (Example 33-35).

TABLE 8

Restoration of BM Proliferation in Immunosuppressive Therapy

| | |
|---|---|
| MDP | + |
| GMDP | ++ |
| norAbu-MDP | + |
| norAbu-GMDP | ++ |

+ = restoration under the level of intact bone-marrow response
++ = restoration above the level of intact bone-marrow response

Example 24

Restoration of BM Proliferation in Radiation Therapy

Method for Administration of test compounds before sublethal irradiation

Institite of Cancer Research (ICR/CD-1) mice (female, age of 3 months, 3-4 per group) were stimulated by s.c. administration of test compounds (volume of 200 µl, 100 nmol per dose) 24 h before sublethal γ-irradiation (6 Gy, $^{60}$Co γray source Chisostat, Chirana Ltd., Czech Republic, at a dose of 0.285 Gy/min.). Mice were sacrificed at day 13 and recovery of GM-CFC in femour was assayed by counting of colonies (CFC) formed after cultivation in medium. Non-irradiated mice were used as control for normal GM-CFC count in femour. PBS and empty liposomes were used as controls for spontaneous recovery. Liposomal MDP was used as reference standard.

The following parameters of hemopoiesis were evaluated:
a) Blood leukocyte counts and bone marrow cellularity. Blood leukocytes (samples of blood drawn from an incision of the tail vein) and nucleated cell elements of the femoral bone marrow (femoral diaphyses flushed with saline) were estimated by means of Coulter Counter (Model ZN, Coulter Electronics).
b) Colony-forming cells in spleen. Endogenous spleen colony-forming units (E-CFUs) were measured on day 9 post the whole-body irradiation with 6.5 Gy (5 mice per group) according to Till and McCulloch.
c) GM-CFC progenitors in bone marrow. Femoral bone marrow cells were obtained from mice by flushing the femour with sterile IMDM medium. Harvested cells were calculated and diluted to $1.5\times10^5$ cells/ml and plated in triplicate in a semisolid environment created by plasma clot (Iscovess modification of Dulbecco's medium, 20% of fetal calf serum, 10% of colony-stimulating factor, 10% of citrate plasma, and $CaCl_2$ 1.5 mg/ml). The cultures were incubated for 7 days at 37° C. in 5% $CO_2$. Colonies of at least 50 cells were scored at 40× magnification.

Statistical significance between individual experimental groups of mice in hemopoietic parameters was calculated by one-way analysis of variance. The Newman-Keuls test for comparison of all pairs of columns and the Dunnett test for comparison of all columns with the control column were used in the analysis.

Method for Administration of Test Compounds after Sub-Lethal Irradiation

The method is exactly as described above except that the test compounds (volume of 200 μl, 100 nmol per dose) were administered 24 h after sublethal γ-irradiation (6 Gy).

Results for Administration of Test Compounds before Sub-Lethal Irradiation

In accordance with method 13, mice were treated with liposomal B30-norAbu-MDP. The numbers of GM-CFC progenitor cells were set as a parameter reflecting the recovery of hemopoiesis[49]. Treatment of mice with liposomal B30-norAbu-MDP induced a significant increase (a doubling of the normal value) of granulocyte-macrophage hemopoietic progenitor cells in bone marrow (FIG. 33). Mice exposed to various doses of γ-radiation (radiation doses of 4.5 to 6.5 Gy) exhibited dose dependant reduction of granulocyte-macrophage hemopoietic progenitor cells in bone marrow (FIG. 33).

FIG. 34 shows a comparison of the induction of GM-CFC progenitor cells caused by liposomal B30-norAbu-MDP versus empty liposome and PBS. The differences in absolute numbers of progenitor cells is a reflection of a seasonal variation in the radio resistance of mice (radiation dose of 6.0 Gy).

Compound 32 had the strongest effect in re-installing GM-CFC progenitor cells to or beyond pre-radiation levels (FIG. 35). Liposomal B30-norAbu-MDP, the reference compound from FIG. 33 and FIG. 34 is shown in column 10.

Results for Administration of Test Compounds after Sub-Lethal Irradiation

Compound 23 and 40 have the strongest effect in re-installing GM-CFC progenitor cells to pre-radiation levels (FIG. 36). Liposomal B30-norAbu-MDP, the reference compound from FIG. 33 and FIG. 34 is shown in column 8.

Compound 40 has one of the best effects in post radiation treatment (FIG. 36), and it has still an acceptable performance in pre radiation priming of the organism (FIG. 35). In contrast, the results for compounds 23 and 32 are almost inverted in these two types of experiments.

Example 25

Survival after (Lethal) Radiation Incident

Method:

Preparations (200 nmol of active substance) were applied to mice (strain ICR, female, 3 months of age, 10 mice per group) by s.c. route 24 h before irradiation (radiation dose of 10 Gy from a $^{60}$Co gamma-ray source at a dose rate of 0.285 Gy/min). PBS and empty liposome served as negative controls, free and liposomal muramyl dipeptide (MDP) served as positive controls.

Results:

Mice were treated with test compounds before receiving lethal irradiation (10 Gy). FIG. 37 indicates an effective and long-lasting activation of nonspecific immunity which is able to oppose the onset of septicemia spreading from injured intestines in the early days post-irradiation. Both the induction of nonspecific immunity and the accelerated restoration of haemopoiesis are responsible for the survival of lethally irradiated mice. Encapsulation of both lipophilic and hydrophilic analogues into liposomes enhances targeting to those intracellular receptors responsible for the induction of effective immune response. Induction of wound healing may support this process.

As for sub-lethal irradiation, applied after priming the mice with the the compounds, compound 32 shows the best performance, followed by a "middle field" of other compounds.

All publications and documents mentioned in the above specification are herein incorporated by reference. Various modifications and variations of the described methods and system of the invention will be apparent to those skilled in the art without departing from the essence of the invention. Although the invention has been described in connection with specific preferred embodiments, it should be understood that the invention as claimed should not be unduly limited to such specific embodiments. Indeed, various modifications of the described modes for carrying out the invention, which are apparent to those skilled in chemistry or related fields, are within the ambit of the following claims.

References

23. Ledvina M., Ježek J., Šaman D., Hřibalová V.: *Collect. Czech. Chem. Commun.* 1998, 63, 590.
24. Ledvina M., Ježek J., Hřibalová V., Turánek J. (IOCB Czech Acad. Sci., Prague): Czech Pat. CZ 296 720, 2006.
25. Farkaš J., Ledvina M., Brokě J., Jeěk J., Zajiček J., Zaoral M.: *Carbohydr. Res.* 1987, 163, 63.
26. Ledvina M., Farkaš J., Zajiček J., Ježek J., Zaoral M.: *Collect. Czech. Chem. Commun.* 1989, 54, 2784.
27. Farkaš J., Ledvina M., Zaoral M., Rotta J., Rýc M. (IOCB Czech Acad. Sci., Prague): Czechoslovak Pat. CZ 250284, 1989.
28. Ledvina M., Šaman D., Ježek J.: *Collect. Czech. Chem. Commun.* 1992, 57, 579.
29. Ledvina M., Zyka D., Ježek J., Trnka T., Šaman D.: *Collect. Czech. Chem. Commun.* 1998, 63, 577.
30. Ledvina M., Ježek J., Saman D., Vaisar T., Hřibalová V.: *Carbohydr. Res.* 1994, 251, 269.
31. Hřibalová V., Vacek A., Toman M., Hořavová P., Ledvina M., Ježek J.: *Peptides 1994. Book of Proc.*, 23rd Eur. Pept. Symp., Braga, Sep. 4-10, 1994 (H. L. S. Maia, Ed.), 847. ESCOM Science Publishers B.V., Leiden 1995.
34. Turánek J., Kašná A., Koudela B., Ledvina M., Miller A. D.: *Parasitology* 2005, 131, 601.
36. Turánek J., Záluská D., Hofer M., Vacek A., Ledvina M., Ježek J.: *Int. J. Immunopharmacol.* 1997, 19, 611.
37. Tamura J., Koike S., Shimadate T.: *J. Carbohydr. Chem.* 1992, 11, 531.
38. Veselý J., Ledvina M., Jindřich J., Šaman D., Trnka T.: *Collect. Czech. Chem. Commun.* 2003, 68, 1264.
39. Jacquinet J., Sinay P.: *J. Org. Chem.* 1977, 42, 720.
40. Turánek J., Záluská D., Neča J.: *Anal. Biochem.* 1997, 249, 131.
41. Turánek J., Kašná A., Zaluská D., Neěa J., in: *Methods in Enzymology*, 365, *Liposomes* (N. Dzunges, Ed.). Page 111. Academic Press Inc, San Diego 2003.
42. Turánek J.: *Anal. Biochem.* 1994, 218, 352.
43. Stařec M., Rosina J., Hřibalová V., Ledvina M., Ježek J.: Modulation of the Frien Virus Course by Stress or Immunomodulating Agents, Abstr., 15th European Immunology Congress (EFIS 2003), Rhodes Island, Greece, Jun. 8-12, 2003, *Immunology Letters* 2003, 87, 163.
44. Pretus H. A., Browder L W., Lucore P., McNamee R. B., Jones E. L., Williams D. L.: *J. Trauma* 2004, 29, 1152.
45. Deepe G. S., Gibbons R., Brunner G. D., Gomez F. J.: *J. Infect. Diseases* 1996, 174, 828.

46. Xu Z. H., Horwich A. L., Sigler P. B.: *Nature* 1997, 388, 741.
47. Wilson C. L., Ouellette A. J., Satchell D. P., Ayabe T., Lopez-Boado Y. S., Stratman J. L., Hultgren S. J., Matrisian L. M., Parks W. C.: *Science* 1999, 286, 113.
48. Odonoghue P. J.: *Int. J. Parasitol.* 1995, 25, 139.
49. Vacek A., Rotkovská D., Bartoničková A.: *Exp. Hematol.* 1990, 18, 234.

The invention claimed is:

1. A compound of Formula I or Formula II

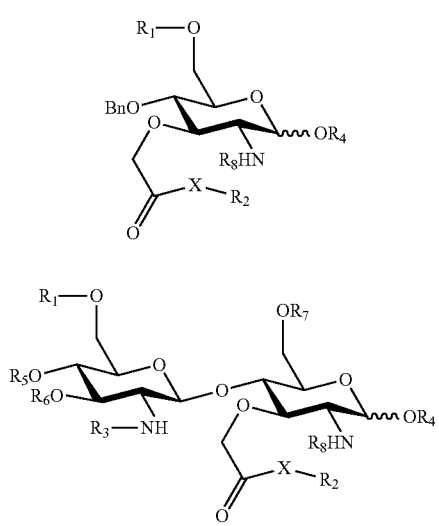

wherein
- $R_1$, $R_4$, $R_5$, $R_6$ and $R_7$ are each independently selected from hydrogen, acetyl, C10-C80 hydrocarbyl, a lipid moiety and a lipid acyl moiety;
- $R_2$ is a hydroxyl, a hydrocarbyl, a lipid moiety, a lipid acyl moiety; or an amino hydrocarbyl group optionally substituted with a hydrocarbyl, a lipid moiety or a lipid acyl moiety;
- $R_3$ and $R_8$ are each independently selected from acetyl, a hydrocarbyl, a lipid moiety and a lipid acyl moiety;
- X is a peptide chain;
- wherein the compound contains a lipid acyl selected from:
  a) the formula $R_{10}$—C(O)— wherein $R_{10}$ is a C10-C80 saturated or unsaturated and branched, cyclic or polycyclic hydrocarbyl group;
  b) a mycolic acid compound of formula VI

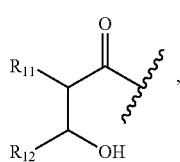

wherein
- $R_{11}$ is a C10 to C30 hydrocarbon group, and
- $R_{12}$ is a C20 to C70 hydrocarbon group optionally bearing one or more carbon-carbon double bonds, cyclopropane rings, keto, hydroxyl, alkoxy, acyloxy, and carboxylic ester groups;

c) cholesteryl hemisuccinyl; or
d) dihydrocholesteryl hemisuccinyl; and
with the proviso that the compound is other than:
(i) a compound of formula I with $R_1$ is 2-tetradecylhexadecanoyl, $R_2$ is —OH, $R_4$ and $R_5$ are hydrogen, $R_8$ is acetyl; and X is -L-Abu-D-isoGln-; and
(ii) a compound of formula II with $R_1$ is 2-tetradecylhexadecanoyl, $R_2$ is —OH; $R_3$ and $R_8$ are acetyl, $R_4$, $R_5$, $R_6$ and $R_7$ are hydrogen; and X is -L-Abu-D-isoGln-.

2. A compound according to claim 1, wherein hydrocarbyl is acyl or alkyl.

3. A compound according to claim 1, wherein
- $R_1$ is hydrogen, acetyl, acyl or alkyl;
- $R_2$ is a hydroxyl, acyl, alkyl; or an amino hydrocarbyl group optionally substituted with an acyl or alkyl;
- $R_3$ is acetyl, acyl or alkyl;
- $R_4$, $R_5$, $R_6$ and $R_7$ are each hydrogen;
- $R_8$ is acetyl; and
- X is a peptide chain.

4. A compound according to claim 1, wherein
- $R_1$ is hydrogen, acetyl or acyl;
- $R_2$ is a hydroxyl, acyl; or an amino hydrocarbyl group substituted with acyl;
- $R_3$ is acetyl or acyl;
- $R_4$, $R_5$, $R_6$ and $R_7$, are each hydrogen; and/or
- $R_8$ is acetyl.

5. A compound according to claim 4, wherein $R_2$ is a substituent of formula V

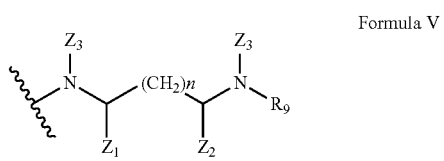

wherein
- $Z_1$ and $Z_2$ are independently hydrogen, a carboxyl group optionally substituted with an alkyl substituent, or a carbamoyl group optionally substituted with one or more alkyl substituents at the nitrogen atom;
- $Z_3$ is hydrogen or a hydrocarbyl group;
- $R_9$ is acyl; and
- n is an integer from 1 to 10.

6. A compound according to claim 1 wherein $R_2$ is an amino group substituted with one or more alkoxycarbonyl groups or with one or more alkyl groups optionally bearing a carboxyl, alkoxycarbonyl, hydroxyl or mercapto functional group.

7. A compound according to claim 1, wherein the lipid acyl is of formula VII:

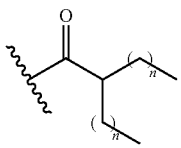

wherein n is 13.

8. A compound according to claim 1, wherein X is a dipeptide comprising one amino acid unit selected independently from L-alanine (Ala) and L-2-aminobutyric acid (Abu) and one amino acid unit selected independently from L- or D- glutamine (Gln), L- or D- asparagine (Asn), L- or D- glutamic acid (Glu) and L- or D- iso-glutamine (isoGln).

9. A compound according to claim 1, wherein X is L-Abu-D-isoGln.

10. A compound according to claim 1 selected from:
(i) the compound of formula I, in which $R_1$ is cholesteryl hemisuccinyl or dihydrocholesteryl hemisuccinyl, $R_2$ is hydroxyl, $R_4$ and $R_5$ are hydrogen, $R_8$ is acetyl and X is L-Abu-D-isoGln;
(ii) the compound of formula I, in which $R_1$ is hydrogen, $R_4$ and $R_5$ are hydrogen,
$R_8$ is acetyl, X is L-Abu-D-isoGln and $R_2$ is

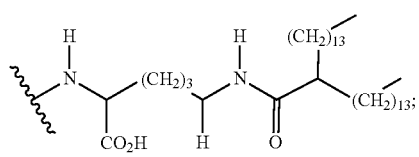

(iii) the compound of formula II, in which $R_1$ is hydrogen, $R_4$, $R_5$, $R_6$ and $R_7$, are each hydrogen, X is L-Abu-D-isoGln, $R_3$ and $R_8$ are acetyl and $R_2$ is

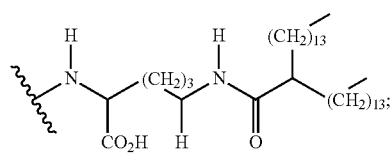

and/or
(iv) the compound of formula II, in which $R_1$ is hydrogen, $R_2$ is hydroxyl, $R_3$ is 2-tetradecylhexadecanoyl, $R_4$, $R_5$, $R_6$ and $R_7$ are each hydrogen, $R_8$ is acetyl and X is L-Abu-D-isoGln.

11. A liposome, proteo-liposome, delivery vehicle or micelle comprising a compound of Formula I or Formula II

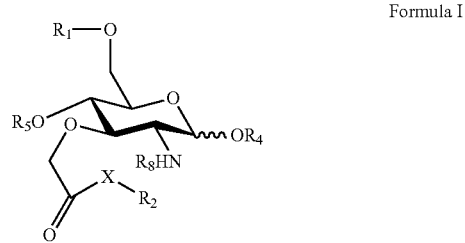

Formula I

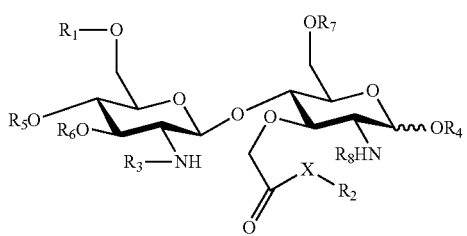

Formula II wherein
$R_1$, $R_4$, $R_5$, $R_6$ and $R_7$ are each independently selected from hydrogen, acetyl, C10-C80 hydrocarbyl, a lipid moiety and a lipid acyl moiety;
$R_2$ is a hydroxyl, a hydrocarbyl, a lipid moiety, a lipid acyl moiety; or an amino hydrocarbyl group optionally substituted with a hydrocarbyl, a lipid moiety or a lipid acyl moiety;
$R_3$ and $R_8$ are each independently selected from acetyl, a hydrocarbyl, a lipid moiety and a lipid acyl moiety;
X is a peptide chain;
wherein at least one C10-C80 hydrocarbyl, lipid moiety or lipid acyl moiety is present.

12. An immune modulator composition comprising:
(i) an antigenic component or precursor or source thereof; and
(ii) an adjuvant comprising a compound of Formula I or Formula II as defined in claim 11.

13. An immune modulator composition according to claim 12 wherein the antigenic component or source or precursor thereof comprises an antigen, or a vector, host cell or a nucleotide sequence capable of expressing an antigenic amino acid sequence in a host cell.

14. An immune modulator composition according to claim 13 wherein the amino acid sequence comprises a heat shock protein or an antigenic or immunogenic fragment thereof that is characteristic for the infection or degenerated cell and that does not cross-react with the host.

15. A liposome, proteo-liposome, delivery vehicle or micelle whose surface comprises or has attached thereto both an adjuvant comprising one or more compounds of Formula I or Formula II as defined in claim 11, and an antigenic component or precursor or source thereof.

16. A combined preparation or composition comprising:
(I) an antigenic component or precursor or source thereof; and
(ii) an adjuvant comprising a compound of Formula I or Formula II as defined in claim 11;
for simultaneous, separate or sequential use for treating and/or preventing a disease or condition, or for therapy, prophylaxis, or for diagnosis.

17. A composition according to claim 16 wherein the antigenic component or source or precursor thereof is encoded by a nucleotide sequence capable of being expressed in a host cell as an antigenic amino acid sequence.

18. Composition according to claim 12, wherein the immune modulator composition further comprises liposomes or a delivery vehicle, which encapsulate (i) the antigenic component and/or (ii) the compound of Formula I or II, either separately or together.

19. Composition according to claim 18 wherein the liposomes comprise a mixture of:
(a) egg-yolk phosphatidylcholine; and
(b) 1-palmitoyl-2-oleoyl-sn-glycero-phosphatidyl glycerol.

20. A pharmaceutical composition or vaccine comprising a compound of Formula I or Formula II as defined in claim 11,
a liposome, delivery vehicle or micelle or composition, and
a pharmaceutically acceptable diluent, carrier, or excipient.

21. A compound of Formula I or Formula II as defined in claim 11, and a liposome, delivery vehicle or micelle or composition; for use in a method of treatment, prophylaxis, therapy and/or diagnosis.

22. A compound of Formula I or Formula II as defined in claim 11, wherein said compound is combined with a liposome, a delivery vehicle, a micelle, or a pharmaceutical composition, for at least one of the following uses:

(a) as an adjuvant, in any form of vaccination, including DNA and other forms of vaccination, for a therapeutic and/or preventive purpose, (b) up-regulation of an antigen-specific Th1, but not of Th2, response;

(c) up-regulation of an antigen-specific mixed Th1 and Th2 response;

(d) induction of non-specific resistance to an infection;

(e) treatment of septic shock;

(f) treatment of a radiation related or caused accident, illness or disorder;

(g) induction of anti-tumour immunity;

(h) co-therapy in cancer chemo- and/or radiation therapy;

(i) treatment of a secondary immunosuppressive state by (i) stimulation of hemopoiesis and/or (ii) stimulation of other bonemarrow derived cells and/or (iii) stimulation of mechanisms of innate immunity;

(j) lymphoma, aplastic anaemia or other anaemic condition;

(k) modulation of an autoimmune state;

(l) cytokine or hematopoiesis induction; and/or (m) treating an indication, disease or disorder resulting from, or associated with, GM-CSF low levels or depletion.

23. A process for the preparation of a compound of Formula I or Formula II as defined in claim 1, comprising a step of converting the allyl group in a compound of Formula Ib or IIb,

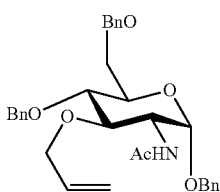

Formula Ib

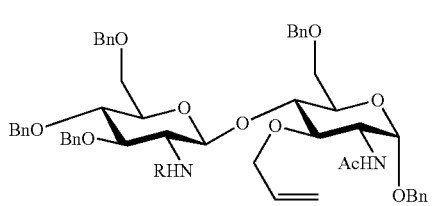

Formula IIb wherein R is acetyl or trichloroethoxycarbonyl (Troc), to a carboxylic acid group, by oxidation, such as by reaction with $RuO_4$ generated in situ from a catalytic amount of $RuCl_3$ with 3 to 5 mol equivalents of $NaIO_4$ at a temperature of 0-5° C.

24. A process for the preparation of a compound of Formula II as defined in claim 1, wherein $R_3$ is an acyl substituent, said process comprising the steps of (i) condensation of a compound of formula IIc with a benzyl ester of peptide chain X,

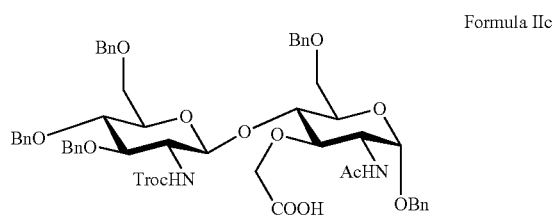

Formula IIc (ii) removal of the Troc protecting group;

(iii) N-acylation of the resulting product with acylchloride derived from the desired fatty acid; and (iv) hydrogenolysis of the benzyl protecting groups.

25. A process for the preparation of a compound of Formula I or Formula II as defined in claim 1, wherein $R_2$ is an amino hydrocarbyl group substituted with acyl, said process comprising the steps of (i) reacting a compound of Formula Id or IId

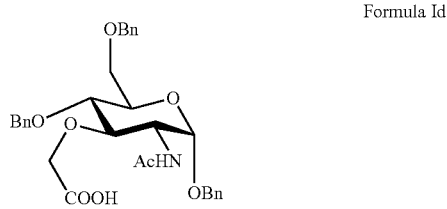

Formula Id

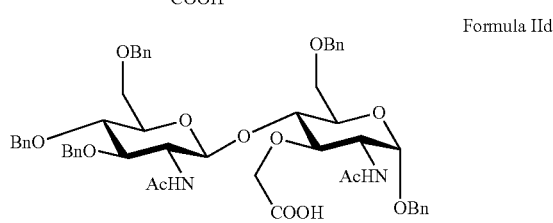

Formula IId with a peptide chain on a solid phase carrier, wherein the peptide chain comprises a ω-amino group in a side chain protected with a 1-(4,4-dimethyl-2,6-dioxocyclohexyliden)-ethyl) group (Dde);

(ii) removing the Dde to provide a carrier-linked glycopeptide synthon with a free ω-amino group;

(iii) N-acylation of the w-amino group with an appropriate lipophilic carboxylic acid;

(iv) cleavage from the solid phase carrier; and (v) hydrogenolysis of the benzyl protecting groups.

26. A compound of formula XII

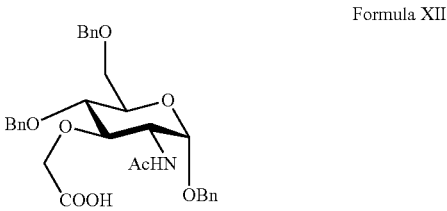

Formula XII

27. A compound of formula XIII

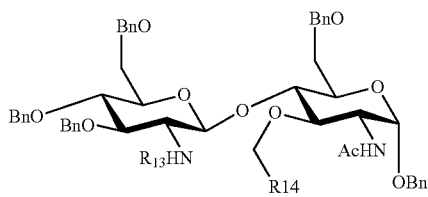

Formula XIII wherein
R$_{13}$ is Troc and R$_{14}$ is —CH=CH$_2$, —COOH, COOCH$_3$ or —CO—X(OBn), wherein X is a peptide chain as defined in claim 1, or R$_{13}$ is a substituent of formula VII

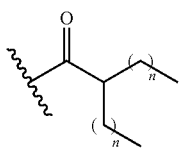

Formula VII wherein n is 13, and R$_{14}$ is —CO—X(OBn), wherein X is a peptide chain as defined in claim 1.

28. A compound of formula XIV

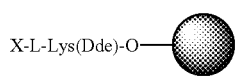

Formula XIV wherein X is a peptide chain as defined in claim 1, and

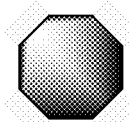

represents a solid phase carrier.

29. A compound of formula XV or XVI

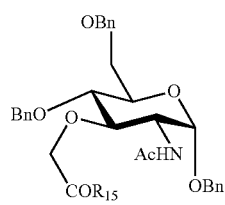

Formula XV

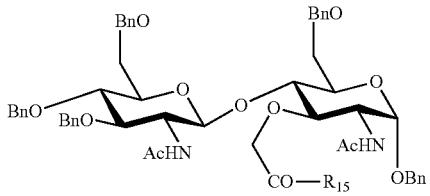

Formula XVI wherein R$_{15}$ is selected from

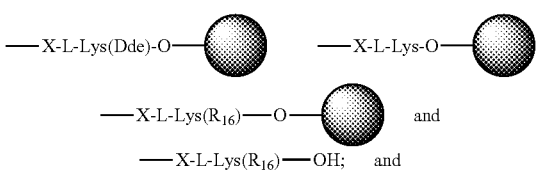

wherein

represents a solid phase carrier;
X is a peptide chain as defined in claims 1; and
R$_{16}$ is

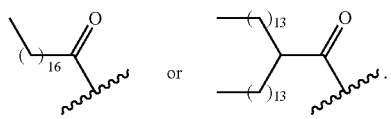

30. A compound of Formula I

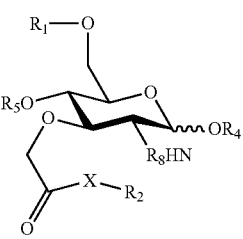

Formula I wherein
R$_1$, R$_4$, and R$_5$ are each independently selected from hydrogen, acetyl, hydrocarbyl, a lipid moiety and a lipid acyl moiety;
R$_2$ is a hydroxyl, a hydrocarbyl, a lipid moiety, a lipid acyl moiety; or an amino hydrocarbyl group optionally substituted with a hydrocarbyl, a lipid moiety or a lipid acyl moiety;
X is a peptide chain;
wherein the compound contains a lipid acyl moiety selected from:
a) the formula R$_{10}$—C(O)— wherein R$_{10}$ is a C10-C80 saturated or unsaturated and branched, cyclic or polycylic hydrocarbyl group; or b) a mycolic acid compound of formula VI

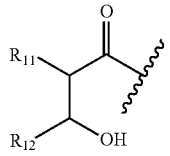

Formula VI wherein
$R_{11}$ is a C10 to C30 hydrocarbon group, and
$R_{12}$ is a C20 to C70 hydrocarbon group optionally bearing one or more carbon-carbon double bonds, cyclopropane rings, keto, hydroxyl, alkoxy, acyloxy, and carboxylic ester groups,
with the proviso that the compound is other than:
(i) a compound of formula I with $R_1$ is 2-tetradecylhexadecanoyl, $R_2$ is —OH, $R_4$ and $R_5$ are hydrogen, $R_8$ is acetyl; and X is -L-Abu-D-isoGln-.

* * * * *